United States Patent [19]

McGuire et al.

[11] Patent Number: 5,549,898

[45] Date of Patent: Aug. 27, 1996

[54] IMMUNOGENIC ANAPLASMA MARGINALE SURFACE ANTIGENS, COMPOSITIONS, AND METHODS OF USE

[76] Inventors: Travis C. McGuire, SW. 920 Crestview; Guy H. Palmer, NW. 335 Dillon, both of Pullman, Wash. 99163; Anthony F. Barbet, 31 SW. 21st Rd., Archer, Fla. 32618; William C. Davis, NW. 300 Yates, Pullman, Wash. 99163

[21] Appl. No.: 228,180

[22] Filed: Apr. 15, 1994

Related U.S. Application Data

[63] Continuation of Ser. No. 79,971, Jun. 18, 1993, abandoned, which is a continuation of Ser. No. 875,554, Apr. 27, 1992, abandoned, which is a continuation of Ser. No. 335,178, Apr. 6, 1989, abandoned, which is a continuation-in-part of Ser. No. 253,143, Oct. 4, 1988, abandoned, Ser. No. 245,855, Sep. 16, 1988, abandoned, and Ser. No. 141,505, Jan. 7, 1988, abandoned, which is a continuation of Ser. No. 761,178, Jul. 3, 1985, abandoned, which is a continuation-in-part of Ser. No. 715,528, Mar. 25, 1985, abandoned.

[51] Int. Cl.$^6$ ............ A61K 39/00; A61K 39/002; A61K 39/005; A61K 39/018
[52] U.S. Cl. .................. 424/269.1; 424/265.1; 424/266.1; 424/270.1
[58] Field of Search .................. 424/93.1, 184.1, 424/190.1, 269.1, 184.1, 265.1, 266.1, 270.1, 269.1

[56] References Cited

PUBLICATIONS

Palmer et al (1984) Immune Sera against Anaplasma Marginale initial bodis neutralizes infectivity for Cattle J & I.

Palmer et al (1985) Immunization with an Isolate–Common Surface Protein Protects Cattle Against Anaplasmosis Science.

Palmer et al Dec. 1985 Presence of Common Antigen including Major Surface Protein Epitopes, between the Cattle (Intraerythrocytic & Techstoges of Anaplasma Marginale.

Barbet et al 1983 Comparison of Proteins Synthesized by two different Isolates of Anaplasma Marginale.

Palmer et al, The Journal of Immunology, 1984 1010–15, Aug. Creceine Jul. 31, 1984).

Palmer, Dissertation Abst Internation, Jun. 1985 vol. 45 No. 7 p. #2069–B (Abstract Only).

Primary Examiner—Hazel F. Sidberry
Attorney, Agent, or Firm—Saliwanchik & Saliwanchik

[57] ABSTRACT

A purified antigenic surface protein of *Anaplasma marginale* has been identified, and is capable of inducing immune responses in ruminants which neutralizes virulent *Anaplasma marginale*. The antigenic surface protein has a molecular weight of about 105,000 daltons, and can be purified by an immunoaffinity chromatography process. The antigen has further utility in diagnostic tests for anaplasmosis. It can be synthesized by polypeptide procedures or by genetic engineering. DNA and amino acid sequences have been developed for the antigen according to this invention. The antigen is useful as a vaccine component for protecting mammals against infection by *Anaplasma marginale* and may be useful for rickettsial organisms other than *Anaplasma marginale*.

2 Claims, 37 Drawing Sheets

FIG. 10A

[ KpnI ]

```
FL  -162  [GGTACC]TGCATTACAACGCAACGCTTGAGTGATGTTGCTTATGGCAGACATTTCCATATACTGTGCAGTATGGTTGTGCTCCC
ID  -162  [GGTACC]TGCATTACAACGCAACGCTTGAGTGATGTTGCTTATGGCAGACATTTCCATATACTGTGCAGTATGGTACGGTGTGCTCCC
WA  -162  [GGTACC]TGCATTACAACGCAACGCTTGAGTGAGTGTTGCTTATTGTGCTTATGGCAGACATTTCCATATACTGTGCAGTATGGTTGTGCTCCC
VA  -162  [GGTACC]TGCATTACAACGCAACGCTTGAGTGAGTGTTGCTTATTGTGCTTATGGCAGACATTTCCATATACTGTGCAGTATGGTTGTGCTCCC
```

A+T-rich            [ -35 ]              [ -10 ]         -1/+1  Untranslated leader

```
FL  -62  CAATTGTTAAAATTAGTATATTAATC[TTGCGA]TTACACGTT-CCGTATGT[TACAAT]CAGGCC/GCCGGTGTGCTGGTTGTGTGGTTGTCCTCT
ID  -62  CAATTGTTAAAATTAGTATATTAATC[TTGCG-T]TACACGTTTCCGTATGT[TACAAT]CAGGCC/GCCGGTGGG-TAGCGTGCTG----------
WA  -62  CAATTGTTAAAATTAGTATATTAATC[TTGCGA]TTACACGTT-CCGTATGT[TACAAT]CAGGCC/GCCGGTGTGTAGCGTGCTGGTTGTGTGGTTGTCCTCT
VA  -62  CAATTGTTAAAATTAGTATATTAATC[TTGCGA]TTACACGTT-CCGTATGT[TACAAT]CAGGCC/GCCGGTGTGTAGCGTGCTGGTTGTGTGGTTGTCCTCT
``` untranslated /f-met

```
FL   39  TTCCCGATGTTGGGTCGTTCGTTTACGTCGCACAAGTTTGTACGCTGTGCCCCTGGCAGTGTATGGGTTTATTTGTTGTTGTGTTGTT(ATG)TCAGCAGA
ID   20  -------------------------CAAGTTTGTACGCTGTGCCCCTGGCAGTGTAGGGTTT----GTTGTTGTGTGTT(ATG)TCAG---A
WA   39  TTCCCGATGTTGGGTCGTTCGTTTACGTCGCACAAGTTTGTACGCTGTGCCCCTGGCAGTGTAGGGTTTATTTGTTGTTGTGTGTT(ATG)TCAGCAGA
VA   39  TTCCCGATGTTGGGTCGTTCGTTTACGTCGCACAAGTTTGTACGCTGTGCCCCTGGCAGTGTAGGGTTTATTTGTTGTTGTGTGTT(ATG)TCAGCAGA
```

/repeat 1

```
FL  139  GTATGTGCCACCCAGTCA/GATGATAGCTCGTCAGCGAGTGGTCAGCAGCAGCAGCAAGAGAGTAGTGTCAGCAGTACATCGTCTCAATTA
ID   80  GTGTGTGTCCCTCCAGCAA/GCTGATAGCTCGTCAGCGAGTGGTCAGCAGCAGCAGCAAGAGAGTAGTGTCATCAGGCCAGTACATCGTCTCAATTA
WA  139  GTATGTGTCCCCCAGCCA/GCTGATAGCTCGTCAGCGAGTGGTCAGCAGCAGCAGCAAGAGAGAGTAGTGTCGTCAAAGATCAGGCCAGTACATCGTCTCAATTA
VA  139  GTATGTGTCACCCAGTCA/GATGATAGCTCGTCAGCGAGTGGTCAGCAGCAGCAGCAAGAGAGAGTAGTGTCGTCAAAGTGA---GGCCAGTACATCGTCTCAATTA
```

/ repeat 2                                                              / repeat 3

```
FL  239  GGA/G---CTGATAGCTCGTCAGCGGGTGGTCAGCAGCGGGTCAGCAGCAAGAGAGAGTAGTGTCATCTCAAAGTGATCAGGCCAGTACATCGTCTCAATTAGG---A/GCTGATAGCT
ID  180  GGA/GGAGCTGATAGCTCGTCAGCGGGTGGTCAGCAGCGGGTCAGCAGCAAGAGAGAGTAGTGTCATCTCAAAGTGA---GGCCAGTACATCGTCTCAATTAGGAGGA/GCTGATAGCT
WA  242  GGA/G---CTGATAGCTCGTCAGCGGGTGGTCAGCAGCGGGTCAGCAGCAAGAGAGAGTAGTGTCATCTCAAAGTGATCAGGCCAGTACATCGTCTCAATTAGG---A/GCTGATAGCT
VA  239  GGA/G---CTGATAGCTCGTCAGCGGGTGGTCAGCAGCGGGTCAGCAGCAAGAGAGAGTAGTGTCATCTCAAAGTGATCAGGCCAGTACATCGTCTCAATTAGG---/-:------
```

FIG. 10B

```
                                                                                          / repeat 4
FL  339  CGTCAGCGGGGTGGTCAGCAGCAAGAGAGTAGTGTGTCATCTCAAAGTGATCAGGCCAGTACATCGTCTCAATTAGG---A/GCTGATAGCTCGTCAGGGGTGG
ID  283  CGTCAGCGAGTGGTCAGCAGCAAGAGAGTAGTGTGTCATCTCAAAGTGA---GGCCAGTACATCGTCTCAATTAGGAGGA/GCTGATAGCTCGTCAGGAGTGG
WA  342  CGTCAGCGGGGTGGTCAGCAGCAAGAGAGTAGTGTGTCATCTCAAAGTGATCAGGCCAGTACATCGTCTCAATTAGG---A/GCTGATAGCTCGTCAGCGGGTGG
VA
                                *                                                               / repeat 5
FL  439  TCAGCAGCAAGAGAGTAGTGTGTCATCTCAAAGTGATCAGGCCAGTACATCGTCTCAATTAGG---A/GCTGATAGCTCGTCAGGGGTGGTCAGCAGCAAGAG
ID  383  TCAGCAGCAAGAGAGTAGTGTGTCATCTCAAAGTGA---GGCCAGTACATCGTCTCAATTAGGAGGA/GCTGATAGCTCGTCAGCGAGTGGTCAGCAGCAAGAG
WA  442  TCAGCAGCAAGAGAGTAGTGTGTCATCTCAAAGTGGTCAGGCCAGTACATCGTCTCAATTAGG---/
VA
                                     *                                              / repeat 6
FL  539  AGTAGTGTGTCATCTCAAAGTGATCAGGCCAGTACATCGTCTCAATTAGG---A/GCTGATAGCTCGTCAGCGGGTGGTCAGCAGCAAGAGAGTAGTGTGTCAT
ID  483  AGTAGTGTGTCATCTCAAAGTGA---GGCCAGTACATCGTCTCAATTAGGAGGA/GCTGATAGCTCGTCAGCGAGTGGTCAGCAGCAAGAGAGTAGTGTGTCAT
WA
VA
                                                            / repeat 7
FL  639  CTCAAAGTGATCAGGCCAGTACATCGTCTCAATTAGGA/GCTGATAGCTCGTCAGCGGGTGGTCAGCAGCAAGAGAGTAGTGTGTCATCTCAAAGTGATCA
ID  583  CTCAAAGTGA---GGCCAGTACATCGTCTCAATTAGG---/
WA
VA
                                                       / repeat 8
FL  739  GGCCAGTACATCGTCTCAATTAGGA/GCTGATAGCTCGTCAGCGGGTGGTCAGCAGCAAGAGAGTAGTGTGTCATCTCAAAGTGATCAGGCCAGTACATCG
ID
WA
VA
         end repeats / unique
FL  839  TCTCAATTAGG/ACTGATTGGGCGGCAAGAGATGCGCTCCAAGGTTGCCGAGTGTTGAGTACATGTTGGCTGCTCCTGCCCTTATTTCTGTAGGGGTCTATG
ID  617  ---------G/ACTGATTGGGCGGCGAGAGAGAGATGCGCTCCAAGGTTGCCGAGTGTTGCCGAGTGTTGAGTACATTTGGCTGCTCCTGCCCTTATCTCTGTAGGGGTCTATG
WA  505  ---------G/ACTGATTGGGCGGCAAGAGATGCGCTCCAAGGTTGCCGAGTGTTGCCGAGTGTTGAGTACATGTTGGCTGCTCCTGCCCTTATCTCTGTAGGGGTCTATG
VA  328  ---------G/ACTGATTGGGCGGCAAGAGATGCGCTCCAAGGTTGCCGAGTGTTGCCGAGTGTTGAGTACATGTTGGCTGCTCCTGCCCTTATTTCTGTAGGGGTCTATG
```

FIG. 10C

```
FL  939  CTGCTCAGGGAGAGATCGCGAGATCGGAGGGTGTGCTCCCCTGCGTGTTGCAGAAGTCGAAGAAGATGGCCTTGTACGCAGCCACTTTCA
ID  706  CTGCTCAGGGAGAGATCGCGAGATCGGAGGGTGTGCTCCCCTGCGTGTTGCAGAAGTCGAAGAAATCGTGAAGATGGCCTTGTACGCAGCCACTTTCA
WA  594  CTGCTCAGGGAGAGATCGCGAGATCGGAGGGTGTGCTCCCCTGCGTGTTGCAGAAGTCGAAGAAATCGTGAGGATGGCCTTGTACGCAGCCACTTTCA
VA  417  CTGCTCAGGGAGAGATCGCGAGATCGGAGGGTGTGCTCCCCTGCGTGTTGCAGAAGTCGAAGAAATCGTGAGGATGGCCTTGTACGCAGCCACTTTCA

FL 1039  TGATAGTGGCCTTTCACTAGGCTCCATACGACTCGTGCTTATGCAGGTTGGGGATAAGTTGGGCTACAAGGTTGAAGATTGGCGAAGGGTACGCCACC
ID  806  TGATAGTGGCCTTTCACTAGGCTCCATACGACTCGTGCTTATGCAGGTTGGGGATAAGTTGGGCTACAAGGTTGAAGATTGGCGAAGGGTACGCCACC
WA  694  TGATAGTGGCCTTTCACTAGGCTCCATACGACTCGTGCTTATGCAGGTTGGGGATAAGTTGGGCTACAAGGTTTGAAGATTGGCGAAGGGTACGCCACC
VA  517  TGATAGTGGCCTTTCACTAGGCTCCATACGACTCGTGCTTATGCAGGTTGGGGATAAGTTGGGCTACAAGGTTTGAAGATTGGCGAAGGGTACGCCACC

FL 1139  TATCTCGGCAAGGCGTTTGCTGACAGGCGTTGGCGCTGGTTGGCGCTGATGTTCAGAGTAGTGGTGCGTGCTGCCAGCCGGCGATCGCAAGCGTTG
ID  906  TATCTCGGCAAGGCGTTTGCTGACAGGCGTTGGCGCTGGTTGGCGCTGATGTTCAGAGTAGTGGTGCGTGCTGCCCTACCGGCCTTGCAGCCGGCGATCGCAAGCGTTG
WA  794  TATCTCGGCAAGGCGTTTGCTGACAGGCGTTGGCGCTGGTTGGCGCTGATGTTCAGAGTAGTGCTCAGATGATGCGCCTGCCAGCCTTGCCAGCCGGCGATCGCAAACGTTG
VA  617  TATCTCGGCAAGGCGTTTGCTGACAGGCGTTGGCGCTGGTTGGCGCTGATGTTCAGAGTAGTGCTCAGATGATGCGCCTGCCAGCCTTGCCAGCCGGCGATCGCAAACGTTG
```

FIG. 10D

```
FL 1239 AGACGTCGTGGTCCCTGCACGGGCGGCCTGGTAAGCAAAGTAGAAAGGGGCGACCTTGAGGCTTTTGTCGACTTCATGTT
ID 1006 AGACGTCGTGGTCCCTGCACGGGCGGCCTGGTAAGCAAAGTAGAAAGGGGCGACCTTGAGGCTTTTGTCGACTTCATGTT
WA 894 AGAAGTCGTGGTCCCTGCACGGCGGCCTGGTACGCAAAGATTTTGACCGTGATACCGAAGTAAAAGGGGCGACCTTGAGGCTTTTGTCGACTTCATGTT
VA 717 AGACGTCGTGGTCCCTGCACGGGCGGCCTGGTAAGCAAAGATTTTGACCGTGATACCAAAGTAGAAAGGGGCGACCTTGAGGCTTTTGTCGACTTCATGTT
                                                          *

FL 1339 TGGCGGTGTGTCGTCGTACAATGATGGGAACGCGTCGCGGGCTAGGAGCGTCTGCGGGCTATTGGAAACGCTTGCCGGGCACGTCACTTGGTATATCGTACAATCAG
ID 1106 TGGCGGTGTGTCGTCGTACGATGATGGGAACGCGTCGCGGGCTAGGAGCGTCTGCGGGCTATTGGAAACGCTTGCCGGGCACGTCACTTGGTATATCGTACAATCAG
WA 994 TGGCGGTGTGTCGTCGTACGATGATGGGAACGCGCGTCGCGGGCTAGGAGCGTCTGCGGGCTATTGGAAACGCTTGCCGGGCACGTCACTTGGTATATCGTACAATCAG
VA 817 TGGCGGTGTGTCGTCGTACAATGATGGGAACGCGTCGCGGGCTAGGAGCGTCTGCGGGCTATTGGAAACGCTTGCCGGGCACGTCACTTGGTATATCGTACAATCAG
                                        *

FL 1439 CTGGATAAGCTTGATGCTGACACTTTGTATAGTGTCGTATCGTTTAGTGCCGGTTCCGCAATAGACAGAGGTGCCGACCTGCAGCATGAGGCTGCGACCCGTCAGCTAGTAGCCGTTCCGTCAACTGT
ID 1206 CTGGATAAGCTTGATGCTGACACTTTGTATAGTGTCGTATCGTTTAGTGCCGCTTCCGCAATAGACAGAGGTGCCGACCTGCAGCATGAGGCTGCGACCCGTCAGCTAGTAGCCGTTCCGTCAACTGT
WA 1094 CTGGATAAGCTTGATGCTGACACTTTGTATAGTGTCGTATCGTTTAGTGCCGGTTCCGCAATAGACAGAGGTGCCGACCTGCAGCATGAGGCTGCGACCCGTCAGCTAGTAGCCGTTCCGTCAACTGT
VA 917 CTGGATAAGCTTGATGCTGACACTTTGTATAGTGTCGTATCGTTTAGTGCCGGTTCCGCAATAGACAGAGGTGCCGACCTGCAGCATGAGGCTGCGACCCGTCAGCTAGTAGCCGTTCCGTCAACTGT
                                                                                        *

FL 1539 GTGTGATGATGTTTGGTGGTGCTCCTGCGGGGCAAGAGAAAACTGCCGAACCTGCCGAACCTGCCAGGCGTGCGTAAGCGTGCTGCGAAGCCTTCGGACACT
ID 1306 GTGTGATGATGTTTGGTGGTGCTCCTGCGGGGCAAGAGAAAACTGCCGAACCTGCCAGGCGTGCGTAAGCGTGCTGCGAAGCCTTCGGACACT
WA 1194 GTGTGATGATGTTTGGTGGTGCTCCTGCGGGGCAAGAGAAAACTGCCGAACCTGCCAGGCGTGCGTAAGCGTGCTGCGAAGCCTTCGGACACT
VA 1017 GTGTGATGATGTTTGGTGGTGCTCCTGCGGGGCAAGAGAAAACTGCCGAACCTGCCAGGCGTGCGTAAGCGTGCTGCGAAGCCTTCGGACACT
                                                                                        *

FL 1639 GCATGGTAAGGTCGTTGATGCAGTTGACCGTGACCTGCAAGCTGCAAAAGAAGGCGGCTCAGCAGGCCTATGCAAGCAAGAAGGCGGCTGGCCGGCTTGACCGGCGTTTGCTTGTCTATCACGGCTTATCGGGCCGTGTTGAACCTAGGCTTATAGGGCGTCCGGTCCGCTGA
ID 1406 GCATGGTAAGGTCGTTGATGCAGTTGACCGTGACCTGCAAGCTGCAAAAGAAGGCGGCTCAGCAGGCCTATGCAAGCAAGAAGGCGGCTGGCCGGCTTGACCGGCGTTTGCTTGTCTATCACGGCTTATCGGGCCGTGTTGAACCTAGGCTTATAGGGCGTCCGGTCCGCTGA
WA 1294 GCATGGTAAGGTCGTTGATGCAGTTGACCGTGACCTGCAAGCTGCAAAAGAAGGCGGCTCAGCAGGCCTATGCAAGCAAGAAGGCGGCTGGCCGGCTTGACCGGCGTTTGCTTGTCTATCACGGCTTATCGGGCCGTGTTGAACCTAGGCTTATAGGGCGTCCGGTCCGCTGA
VA 1117 GCATGGTAAGGTCGTTGATGCAGTTGACCGTGACCTGCAAGCTGCAAAAGAAGGCGGCTCAGCAGGCCTATGCAAGCAAGAAGGCGGCTGGCCGGCTTGACCGGCGTTTGCTTGTCTATCACGGCTTATCGGGCCGTGTTGAACCTAGGCTTATAGGGCGTCCGGTCCGCTGA
                                                                                                *

FL 1739 ACTACACAGCTTGTTGTTAGCTATCGTTGCTATCACGGCTATCGGGCCGTGTTGAACCTAGGCTTATAGGGCGTCCGGTCCGCTGA
ID 1506 ACTACACAGCTTGTTGTTAGCTATCGTTGCTATCACGGCTATCGGGCCGTGTTGAACCTAGGCTTATAGGGCGTCCGGTCCGCTGA
WA 1394 ACTACACAGCTTGTTGTTAGCTATCGTTGCTATCACGGCTATCGGGCCGTGTTGAACCTAGGCTTATAGGGCGTCCGGTCCGCTGA
VA 1217 ACTACACAGCTTGTTGTTAGCTATCGTTGCTATCACGGCTATCGGGCCGTGTTGAACCTAGGCTTATAGGGCGTCCGGTCCGCTGA
```

FIG. 10E

```
FL 1839 TTTGGGGCTGCCTGGCACTAGTAGCACTGCTGCTGCCATTACTTGGTATGGCTGTGTGCATACGGCAGTGAGTGCTTCGAGTCAAAAGAAGGCTGCCGGTGGTGC
ID 1606 TTTGGGGCTGCCTGGCACTAGTAGCACTGCTGCTGCCATTACTTGGTATGGCTGTGTGCATACGGCAGTGAGTGCTTCGAGTCAAAAGAAGGCTGCCGGTGGTGC
WA 1494 TTTGGGGCTGCCTGGCACTAGTAGCACTGCTGCTGCCATTACTTGGTATGGCTGTGTGCATACGGCAGTGAGTGCTTCGAGTCAAAGAAGAAGGCTGCCGGTGGTGC
VA 1317 TTTGGGGCTGCCTGGCACTAGTAGCACTGCTGCTGCCATTACTTGGTATGGCTGTGTGCATACGGCAGTGAGTGCTTCGAGTCAAAGAAGAAGGCTGCCGGTGGTGC

FL 1939 GCAACGGGTTGCTGCTCAGGAGAGGTCTAGGAGAATTGTCCCGTGCGAGACAGGAAGATCAGCAGAAGTTGCATGTTCCCGCGATACTGACCGGGTTGAGC
ID 1706 GCAACGGGTTGCTGCTCAGGAGAGGTCTAGGAGAATTGTCCCGTGCGAGACAGGAAGATCAGCAGAAGTTGCATGTTCCCGCGATACTGACCGGGTTGAGC
WA 1594 GCAACGGGTTGCTGCTCAGGAGAGGTCTAGGAGAATTGTCCCGTGCGAGACAGGAAGATCAGCAGAAGTTGCATGTTCCCGCGATACTGACCGGGTTGAGC
VA 1417 GCAACGGGTTGCTGCTCAGGAGAGGTCTAGGAGAATTGTCCCGTGCGAGACAGGAAGATCAGCAGAAGTTGCATGTTCCCGCGATACTGACCGGGTTGAGC

FL 2039 GTGCTTGTGTTATTGCTGCCGTCGTGCCTTGTGTATTGCTGCCTTGTTGTTGACGCGAGGCGGGACGTGGCAGGGCAGCATATGTTTCCTAGCCGACTCGTACGGCTCGTACC
ID 1806 GTGCTTGTGTTATTGCTGCCGTCGTGCCTTGTGTATTGCTGCCTTGTTGTTGACGCGAGGCGGGACGTGGCAGGGCAGCATATGTTTCCTAGCCGACTCGTACGGCTCGTACC
WA 1694 GTGCTTGTGTTATTGCTGCCGTCGTGCCTTGTGTATTGCTGCCTTGTTGTTGACGCGAGGCGGGACGTGGCAGGGCAGCATATGTTTCCTAGCCGACTCGTACGGCTCGTACC
VA 1517 GTGCTTGTGTTATTGCTGCCGTCGTGCCTTGTGTATTGCTGCCTTGTTGTTGACGCGAGGCGGGACGTGGCAGGGCAGCATATGTTTCCTAGCCGACTCGTACGGCTCGTACC

FL 2139 TTGCGATCAGTGCCGCTGTTGTAATGCAACACGTGACCAATCGTTGGCAGAAGAGTGTGATAGCAAGTGTGCTACAGCTCGTACAGCTCGTACAGCTCGTACAGCTCAAGCTGTACC
ID 1906 TTGCGATCAGTGCCGCTGTTGTAATGCAACACGTGACCAATCGTTGGCAGAAGAGTGTGATAGCAAGTGTGCTACAGCTCGTACAGCTCGTACAGCTCGTACAGCTCAAGCTGTACC
WA 1794 TTGCGATCAGTGCCGCTGTTGTAATGCAACACGTGACCAATCGTTGGCAGAAGAGTGTGATAGCAAGTGTGCTACAGCTCGTACAGCTCGTACAGCTCGTACAGCTCAAGCTGTACC
VA 1617 TTGCGATCAGTGCCGCTGTTGTAATGCAACACGTGACCAATCGTTGGCAGAAGAGTGTGATAGCAAGTGTGCTACAGCTCGTACAGCTCGTACAGCTCGTACAGCTCAAGCTGTACC

FL 2239 CGGTGGCCAGCAGCGCGTACCGAGGGCGTTGTTAGCGGTGGGCGTGGTGTTCCCGAAGAAGGCCAAGAAGGCGGGCGTTGTTCCCGAACTTCCGTGCCGTCAGCCGAG
ID 2006 CGGTGGCCAGCAGCGCGTACCGAGGGCGTTGTTAGCGGTGGGCGTGGTGTTCCCGAAGAAGGCCAAGAAGGCGGGCGTTGTTCCCGAACTTCCGTGCCGTCAGCCGGG
WA 1894 CGGTGGCCAGCAGCGCGTACCGAGGGCGTTGTTAGCGGTGGGCGTGGTGTTCCCGAAGAAGGCCAAGAAGGCGGGCGTTGTTCCCGAACTTCCGTGCCGTCAGCCGGG
VA 1717 CGGTGGCCAGCAGCGCGTACCGAGGGCGTTGTTAGCGGTGGGCGTGGTGTTCCCGAAGAAGGCCAAGAAGGCGGGCGTTGTTCCCGAACTTCCGTGCCGTCAGCCGAG
                                                                                                    (stop)
                                                                                                      *
FL 2339 TCTGGGCCGTACCTCCTGCTACCTTATGGTTAGTGTGGATCCACAACTTGTTGCTACTTTGGGAGCAGGTGTGGCAGCAGGTGGGCGG(TAA)AGCCCGC
ID 2106 TCTGGGTCCGTACCTCCTGCTACCTTATGCGTTAGTCAGTGATGTGGATCCACACAACTTGTTGCTACTTTGGGAGCAGGTGTGGCAGCAGGTGCGGCGG(TAA)AGCTTGT
WA 1994 TCTGGGGCCGTACCTCCTGCTACCTCCTGCTACCATTAGTGGTTAGTGGATCCACACACAACTTGTTGCTACTTTGGGAGCAGGTGTGGCAGCAGGTGGGCGG(TAA)AGCCCGC
VA 1817 TCTGGGGCCGTACCTCCTGCTACCTCCTGCTACCATTAGTGGTTAGTGGATCCACACACAACTTGTTGCTACTTTGGGAGCAGGTGTGGCAGCAGGTGGGCGG(TAA)AGCCCGC
```

FIG. 10F

```
FL 2439 TTTATAGCTTGGGTTTTG-CTTCATAGGTGGCGATTGGGCGCTGTTGAGGAGTGGCATGAACGGGCGGTTGGGTTGCTGCAACGTCCCGGTAG
ID 2206 -----AGCCCGGTTTTGGGTTTTG-CTTCATAGGTTGGCGATTGGGCCTGTTGAGGGGTGGATAGTTG-CATGAACGGGGCGGTTGAGTTGCTGCAACGTCCCGGAG
WA 2094 TTTATAGCTTGGGTTTTG-CTTCATAGGTGGCGATTGGGCGCTGTTGAGGAGTGGATAGTTGGCATGAACGGGCGGTTGGGTTGCTGCAACGTCCCGGTAG
VA 1917 TTTATAGCTTGGGTTTTG-CTTCATAGGTGGGCGATTGGGCCTGTTGAGGAGTGGATAGTTGGCATGAACGGGCGGTTGGGTTGCTGCAACGTCCCGGTAG
                      *                                              *                        *                        *

FL 2539 GCAAGAGTTTCCGGTCTTTGATAGAGTC
ID 2301 GCAA-A-TTTCCGGTCTTTGATAGCCGTC
WA 2194 GCAAGAGTTTCCGGTCTTTGATAGAGTC
VA 2017 GCAAGAGTTTCCGGTCTTTGATAGAGTC
             *
```

FIG. 11B

```
   -35                           -10           Start              Allele
TTGCGATTACACGTTCCGTATGTTACAATCAGGCCGC...                          FL, VA, WA
TTGCGTTACACGITTCCGTATGTTACAATCAGGCCGC...                          ID
TTGacATnnnnnnnnnnnnnnnnTAtAATnnnnnCat...                          E. coli
```

FIG. 12A

```
            unique /repeat 1                                           /repeat 2                                       /repeat 3
FL    1  MSAEYVPTQS/DDSSSASGQQQESSVSSQS-EASTSSQLG-/ADSSSAGGQQQESSVSSQSDQASTSSQLG-/ADSSSAGGQQQESSVSSQSDQAS
VA    1  MSAEYVSTQS/DDSSSASGQQQESSVSSQS-EASTSSQLG-/ADSSSAGGQQQESSVSSQSDQASTSSQLG-/ADSSSAGGQQQESSVSSQSDQAS
WA    1  MSAEYVSPQP/ADSSSAGGQQQESSVSSQSDQASTSSQLG-/ADSSSAGGQQQESSVSSQSDQASTSSQLG-/ADSSSAGGQQQESSVSSQSDQAS
ID    1  MS-ECVSLQQ/ADSSSASGQQQESSVSSQS-EASTSSQLGG/ADSSSASGQQQESSVSSQS-EASTSSQLGG/ADSSSASGQQQESSVSSQS-EAS
                                                                                                       *
                             /repeat 4                                    /repeat 5                                  /repeat 6
FL   91  TSSQLG-/ADSSSAGGQQQESSVSSQSDQASTSSQLG-/ADSSSAGGQQQESSVSSQSDQASTSSQLG-/ADSSSAGGQQQESSVSSQSDQASTSS
VA    -  -------/------------------------------/------------------------------/----------------------------
WA   92  TSSQLG-/ADSSSAGGQQQESSVSSQSDQASTSGQAS-/------------------------------/----------------------------
ID   90  TSSQLGG/ADSSSASGQQQESSVSSQS-EASTSSQLGG/ADSSSASGQQQESSVSSQS-EASTSSQLGG/ADSSSASGQQQESSVSSQS-EASTSS
                                                                                                       *
                             /repeat 7                              /repeat 8                              /unique
FL  181  QLG-/ADSSSAGGQQQESSVSSQSDQASTSSQLG-/ADSSSAGGQQQESSVSSQSDQASTSSQLG-/TDWRQEMRSKVASVEYMLAARALISVGVY
VA    -  ----/------------------------------/------------------------------/----TDWRQEMRSKVASVEYMLAARALISVGVY
WA    -  ----/------------------------------/------------------------------/----TDWRQEMRSKVASVEYMLAARALISVGVY
ID  180  QLG-/----------------------------- /------------------------------/----TDWRREMRSKVASVEYILAARALISVGVY
                                                                                                       *

FL  271  AAQGEIARSRGCAPLRVAEVEEIVKDGLVRSHFHDSGLSLGSIRLVLMQVGDKLGLQGLKIGEGYATYLAQAFADSVVAADVQSSGACS
VA   97  AAQGEIARSRGCAPLRVAEVEEIVKDGLVRSHFHDSGLSLGSIRLVLMQVGDKLGLQGLKIGEGYATYLAQAFADSVVAADVQSSGACS
WA  156  AAQGEIARSRGCAPLRVAEVEEIVRDGLVRSHFHDSGLSLGSIRLVLMQVGDKLGLQGLKIGEGYATYLAQAFADSVVAADAQSSDACP
ID  212  AAQGEIARSRGCAPLRVAEVEEIVRDGLVRSHFHDSGLSLGSIRLVLMQVGDKLGLQGLKIGEGYATYLAQAFADSVVAADVQSSGACP
                                  *                                                                    *

FL  361  ASLDSAIANVETSWSLHGGLVSKGFDRDTKVERGDLEAFVDFMFGGVSYNDGNASAARSVLETLAGHVDALGISYNQLDKLDADTLYSVV
VA  187  ASLDSAIANVETSWSLHGGLVSKGFDRDTKVERGDLEAFVDFMFGGVSYNDGNASAARSVLETLAGHVDALGISYNQLDKLDADTLYSVV
WA  246  ASLDSAIANVEKSWSLHGGLVSKGFDRDTEVKRGDLEAFVDFMFGGVSYDDGNASAARSVLETLAGHVDALGISYNQLDKLDADTLYSVV
ID  302  TGLDSAIASVETSWSLHGGLVRKDFDRDTKVERGDLEAFVDFMFGGVSYDDGNASAARSVLETLAGHVDALGISYNQLDRLDADTLYSVV
        **     *      *        *     *    *                 *                            *
```

FIG. 12B

```
FL 451 SFSAGSAIDRGAVSDAADKFRVMMFGGAPAGQEKTAEPEHEAATPSASSVPSTVHGKVVDAVDRAKEAAKQAYAGVRKRYVAKPSDTTTQ
VA 277 SFSAGSAIDRGAVSDAADKFRVMMFGGAPAGQEKTAEPEHEAATPSASSVPSTVHGKVVDAVDRAKEAAKQAYAGVRKRYVAKPSDTTTQ
WA 336 SFSAGYAIDRGAVSDAADKFRVMMFGGAPAGQEKTAEPEHEAATPSASSVPSTVHGKVVDAVDRAKEAAKQAYAGVRKRYVAKPSDTTTQ
ID  392 SFSAASAIDRGAVSDAADKFRVMMFGGAPAGQEKTAEPEHEAATPSASSVLSTVHGKVVDAVDRAKEAAQQAYAGVRKRYVAKPSDTTTQ
                **                                               *

FL 541 LVVAITALLITAFAICACLEPRLIGASGPLIWGCLALVALLPLLGMAVHTAVSASSQKKAAGGAQRVAAQERSRELSRARQEDQQKLHVP
VA 367 LVVAITALLITAFAICACLEPRLIGASGPLIWGCLALVALLPLLGMAVHTAVSASSQKKAAGGAQRVAAQERSRELSRARQEDQQKLHVP
WA 426 LVVAITALLITAFAICACLEPRLIGASGPLIWGCLALVALLPLLGMAVHTAVSASSQKKAAGGAQRVAAQERSRELSRARQEDQQKLHVP
ID  482 LVVAITALLITAFAICACLEPRLIGASGPLIWGCLALVALLPLLGMAVHTAVSASSQKKAAGGAQRVAAQERSRELSRARQEDQQKLHVP
                                                                         *

FL 631 AILTGLSVLVFIAAVVACIAVDARRGTWQGSICFLAAFVLFAISAAVVMATRDQSLAEECDSKCATARTAQAVPGGQQQPRATEGVVSGG
VA 457 AILTGLSVLVFIAAVVACIAVDARRGTWQGSICFLAAFVLFAISAAVVMATRDQSLAEECDSKCATARTAQAVPGGQQQPRATEGVVSGG
WA 516 AILTGLSVLVFIAAVVACIAVDARRGTWQGSICFLAAFVLFAISAAVVMATRDQSLAEECDSKCATARTAQAVPGGQQQPRATEGVVSGG
ID  572 AILTGLSVLVFIAAVVACIAVDARRGTWQGSICFLAAFVLFAISAAVVMATRDQSLAEECDSKCATARTAQAVPGGQQQPRATEGVVSGG

FL 721 GQEGGAGVPGTSVPSAESGAVPPATIMVSVDPQLVATLGAGVAQAAA-
VA 547 GQEGGAGVPGTSVPSAESGAVPPATIMVSVDPQLVATLGAGVAQAAA-
WA 606 GQEGGAGVPGTSAPSAGSGAVPPATIMVSVDPQLVATLGAGVAQAAA-
ID  662 GQEGGAGVPGTSVPSAGSGSVPPATVMVSVDPQLVATLGAGAAQAAA-
                      *    *  *         *            *
```

FIG. 13

```
                                      Number in allele
Form    Sequence                      FL  VA  WA  ID
A:  DDSSSASGQQQESSVSSQS-[EASTSS]QLG-   1   1   0   0
B:  ADSSSAGGQQQESSVSSQSD[QASTSS]QLG-   7   1   3   0
C:  ADSSSAGGQQQESSVSSQSG[QASTSS]QLG-   0   0   1   0
D:  ADSSSASGQQQESSVSSQS-[EASTSS]QLGG   0   0   0   5
E:  ADSSSASGQQQESSVSSQS-[EASTSS]QLG-   0   0   0   1
```

FIG. 14

```
                                            Reactivity
N-terminus                                  w/ mAb 22B1
DSSSAGGQQQESSVSSQSD[QASTSS]QLGA                 +
     SAGGQQQESSVSSQSD[QASTSS]QLGADSSSA          +
                    [QASTSS]QLGADSSSA           +
                SQSD[QASTSS]                    +
                 SQS-[EASTSS]Q                  +
        QESSVSSQSD                              −
        QQESSV                                  −
                    [QASTSS]                    +
                    [EASTSS]                    +
                    [ ASTSS]                    −
                    [  STSS]                    −
                    [QASTS ]                    −
                    [QAST  ]                    −
```

FIG. 15A

```
          10        20        30        40        50        60
           *         *         *         *         *         *
GAGCTCGGGCCCCGTTCTGCGCACGCGTCTGTGGACCTTGCTGCGGGGCGGGTGCTCTGT
^^^ ^^^^^ ^    ^^^ ^ ^ ^    ^         ^               ^   ^ ^

AluI    ApaI      HhaI  BbvI    AvaII    Fnu4HI           Bsp1286
AvaI    BanII     HinPI ThaI    Sau96I                    HgiAI
 BanII  Bsp1286   MluI                               MnlI
 Bsp1286 HgaI   MstI
 SstIHaeIII
 HgiAINlaIV
    NlaIV
   Sau96I 70        80        90       100       110       120
           *         *         *         *         *         *
GAGGCGAAAATCGCCGGACAGCCGAAAATTTGGTGAAATAAAGCAATGCCGGGTGGCATG
          ^              ^ ^                    ^  ^^         ^

HpaII         EcoRI'           HphI HpaII        NlaIII
                       EcoRI*                NciI
                                             ScrFI 130       140       150       160       170       180
           *         *         *         *         *         *
TTAAGAGCGCCTAACCGGTTATCAAGACATTGTTAAGTAGGTAGGTGCGATGACAGAAGA
    ^ ^^    ^

HaeIIHpaII
    HhaI
HinPI 190       200       210       220       230       240
           *         *         *         *         *         *
CGACAAGCAACAACAACAGAATCAAAGCGATGTAGTACAAGCCATCTCGGCCGTATTCCA
       ^          ^^             ^         ^^ ^

MboII      HinfI         RsaI       BglI
```

FIG. 15B

```
                Tth111I                                    HaeIII
                                                           XmaIII
      250       260       270       280       290       300
       *         *         *         *         *         *
GCGCAAGAGTGCAGAGCTGCAGCGGCTGAATGACTTCATAAAAGGCGCTGATGGTACACT
^ ^             ^^  ^^  ^            ^^         ^ ^^      ^ ^
BbvI         AluIFnu4HI      BbvI             HaeII    FokI
HhaI         Fnu4HIFnu4HI    XmnI             HhaI    RsaI
HinPI              PstI                       HinPI 310       320       330       340       350       360
       *         *         *         *         *         *
CAAGAACGTCCATCCCCACATGAAGTCACTGGAAGCGCTTTCTAAGCAACTATCAGAAAA
                  ^              ^  ^^   ^
                NlaIII         HhaI DdeI
                               HaeII
                               HinPI 370       380       390       400       410       420
       *         *         *         *         *         *
GATTGCAGCTGAGGCAGCAGCGAAGGCAGATGCTAAATACGAGAGCGTGGGACTACGTGC
^   ^  ^^      ^  ^^^      ^    ^                          ^
MnlI AluI    BbvI      BbvI                              BbvI
     DdeI    Fnu4HI    BbvI
     Fnu4HI  Fnu4HI
     PvuII   SfaNI 430       440       450       460       470       480
       *         *         *         *         *         *
TAAAGCAGCTGCAGCATTAGGTAATCTCGGGCGGCTTGTCGCCCGTGGTAAACTCAAGAG
^   ^^   ^^    ^      ^  ^      ^                        ^ ^
AluI  PstIBbvI     AvaI  Fnu4HI                       SfaNIAluI
Fnu4HIFnu4HI       BbvI
    Fnu4HI
    PvuII 490       500       510       520       530       540
       *         *         *         *         *         *
CTCAGATGCACCCAAGGACCTTGACCAGAGCATTGACGCACTACCGTTCATGGATGAAGC
^^            ^                              ^          ^
BanII       AvaII                          HgaI       NlaIII
Bsp1286     Sau96I
DdeI
HgiAI
SstI 550       560       570       580       590       600
```

FIG. 15C

```
        *         *         *         *         *         *
ACCTGACACTGGTGAGAAGATTGAAGTACCAGCGGGTGAGGAGCAAGAATTTGGCAAGGC
 ^                  ^    ^^ ^                    ^ ^         ^
FokI              HphI MboII                  EcoRI'       Fnu4HI
                       MnlI                   EcoRI*
                       RsaI                   HphI 610       620       630       640       650       660
        *         *         *         *         *         *
AGCAGCTTGGGGTCTAGCAGGCTTCAAGCGTACAGTGGATGAAAGCCTGGAGATGTTAGA
 ^ ^      ^    ^              ^                ^ ^ ^       ^
AluI   BbvI                 RsaI             BstNI       MnlI
Fnu4HI    BbvI                               EcoRII
                                             FokI
                                             ScrFI 670       680       690       700       710       720
        *         *         *         *         *         *
CCGAGGCATGCACATGCTCGCGGAAGGCCAGGCACAGATATCACAGGGGATTGACGCCAA
      ^   ^     ^     ^ ^           ^              ^
   NlaIIINlaIII      BstNI       EcoRV          AhaII
      SphI      ThaI EcoRII                     HgiDI
                     HaeIII
                     ScrFI 730       740       750       760       770       780
        *         *         *         *         *         *
GGATACTGCACTAGTTAGGGAAGGTCTGGAAACATCTAGACTTGGTGCAGGGTTATGTCG
 ^                            ^
HgaI                        XbaI 790       800       810       820       830       840
        *         *         *         *         *         *
CAATGGCTTGGTAGAGGCCTCCTACGGCGTTGGTTATGCCAATGAGACCATGGGCAAGTA
    ^          ^         ^                        ^ ^
  MnlI       HaeIII     MnlI                    NcoI
             StuI                                  NlaIII 850       860       870       880       890       900
        *         *         *         *         *         *
TGCCGGCAAGGGTCTAGACAAGTGTAAAAACAAACTCGACAATGCATGCCACAAGTGGAG
 ^^       ^                               ^       ^ ^
HpaII   XbaI                           TaqI    NlaIII
NaeI                                           NsiI
                                               SphI 910       920       930       940       950       960
        *         *         *         *         *         *
```

FIG. 15D

```
CAAGGCTCTCGAAGAGATTGAAAGCCTGCGCACAGCAATCGACGCGAAGGCAGAACAGCA
     ^             ^    ^^^         ^       ^         ^
    TaqI         MboII  HhaI      TaqI    ThaI      HgaI
                       HinPI
                       MstI 970        980        990       1000       1010       1020
         *          *          *          *          *          *
AGTTGAAGGTGAAGCATGGTCTCCTGAAGGGGTCAGTGCTAACACATTCTACAAAGGACT
                  ^ ^
                  HphI
                  NlaIII 1030       1040       1050       1060       1070       1080
         *          *          *          *          *          *
GCATAAAATTGGCACCGCAATTGCAGTAGCAGCTCAAGCTACCTGGGAAGGCTTGGCTAT
 ^       ^ ^     ^              ^ ^     ^ ^   ^
 BanI    EcoRI*              AluI    AluI BstNI
 EcoRI*  NlaIV               Fnu4HI     BbvI
                                      EcoRII
                                      ScrFI 1090       1100       1110       1120       1130       1140
         *          *          *          *          *          *
GACCGGTAAGTTCATGGGTGCTGTAGCTAAACTAGCTGGTGCAGTATCCATGTGCGTTGC
 ^              ^         ^          ^                  ^      ^
 HpaII          NlaIII    AluI       AluI             NlaIII   Fnu4HI 1150       1160       1170       1180       1190       1200
         *          *          *          *          *          *
AGCATACACCGCAGCTATCGTGGGTATGGCCGGCAGCTACACCTGCGACGCTGCTGCTGAC
  ^^ ^           ^      ^^   ^ ^^    ^      ^          ^  ^ ^
   AluI         BbvI    HaeIIIAluIBbvI BbvI          Fnu4HI
  BbvI                  Fnu4HIBbvI                   Fnu4HI
  Fnu4HI                   Fnu4HI                    HgaI 1210       1220       1230       1240       1250       1260
         *          *          *          *          *          *
AGCTATGGACAATCAATCCGTAAACAATGCCGTAGTTAAAGTCAGTGAGTACCTTCACAG
  ^                                                ^
  AluI                                            RsaI 1270       1280       1290       1300       1310       1320
         *          *          *          *          *          *
TAACGTAGAACAAGCAACTAAAGACCTCATGGCTTCAGAGTTTGCCATGATGACATTTGG
              ^       ^  ^                       ^
             Tth111I  MnlI                     NlaIII
                     NlaIII
```

FIG. 15E

```
         1330      1340      1350      1360      1370      1380
          *         *         *         *         *         *
    TGGCATCATGACGTGTGCCAAGCTTATGAAGGGCTCCTTCGCAGCAATCAATCAGAAGTT
       ^ ^         ^ ^              ^^      ^          ^
       NlaIII      AluI             BanII  Fnu4HI      BbvI
         SfaNI    HindIII           Bsp1286
                                    NlaIV 1390      1400      1410      1420      1430      1440
          *         *         *         *         *         *
    TGAAGAAATCAACGCCACCCTCACACGGGAGGCCACAGACATCGCTCAAGGGGTCAAGGA
              ^         ^            ^  ^
              MboII    MnlI         HaeIII 1450      1460      1470      1480      1490      1500
          *         *         *         *         *         *
    GACTTACCAGTCTATTGGCGATGCATTTGGCAATGCATTCAAGTCTGTTGGCGATGCATT
         ^  ^           ^              ^       ^                ^
         BstXI         NsiI           NsiI    SfaNI             NsiI
         BstXI
       SfaNI 1510      1520      1530      1540      1550      1560
          *         *         *         *         *         *
    CAAGTCTATTGGCGATGCATTCAAGTCAGCTAATGATGGCATAGCTAAGTGGACAGCAGC
     ^                ^           ^             ^^          ^ ^
     SfaNI           NsiI        AluI          AluI         AluI
                                              DdeI         Fnu4HI 1570      1580      1590      1600      1610      1620
          *         *         *         *         *         *
    TCTAGCAGGTTATGCGTCAGTTGAACAGCTAGAAGAAGCAAAGGAAGCAGACAGGGTACA
     ^  ^                      ^               ^              ^
     HgaI BbvI                 AluI           MboII           RsaI 1630      1640      1650      1660      1670      1680
          *         *         *         *         *         *
    GGCTGAGCAGCGAGCTGAAGCACAAGCAATGACCGAGCGTGTGGCAGGGGAGCGTGCAGC
     ^    ^      ^   ^                 ^                    ^ ^
     DdeI Fnu4HIAluI BbvI              Tth111II             BbvI
                                                            Fnu4HI 1690      1700      1710      1720      1730      1740
          *         *         *         *         *         *
```

FIG. 15F

```
AACAGTTGCTGCAGGGACTGAAACCATTAAGACCATCGTCAGCGATATGCGGAATGAGCT
  ^^ ^                                                    ^
  BbvI PstI                                               AluI
  Fnu4HI 1750      1760      1770      1780      1790      1800
     *         *         *         *         *         *
TGCTAAAGGGCATGAACAGCTTCAGCTCGTCATCACCGATATGTGTAATGAGCTTGCACA
          ^   ^^        ^                           ^
          AluI AluI                                 AluI
          NlaIII HphI
          XmnI 1810      1820      1830      1840      1850      1860
     *         *         *         *         *         *
AATAGGTGCATTCTCCCAAGCAGAGCGCGATGCACTTGTAAGTCCTTCACGCCTAAACC
     ^      ^ ^    ^                  ^
         SfaNI   HhaITth111II        XmnI
                 HinPI
                 ThaI 1870      1880      1890      1900      1910      1920
     *         *         *         *         *         *
TCCTGCTAGGACAACCAAGGAGCTTATCTCACATATGCATTCGGGCCTAGAATCCGTGAT
 ^            ^           ^       ^   ^ ^      ^ ^
 MnlI         AluI        NdeI    NsiI HaeIII  EcoRI'
                                       Sau96I  HinfI 1930      1940      1950      1960      1970      1980
     *         *         *         *·        *         *
GTTCCGTATGGCACGTAGTCTTGGGATCATGAGCAAAGCTAGTATAGAGGCAAACTCGCA
         ^ ^      ^        ^^
         DpnI NlaIII AluI
         MboI       MnlI
         Sau3A 1990      2000      2010      2020      2030      2040
     *         *         *         *         *         *
GGACAATAGTGTAGAGGTGGCAGAGATCAGCCCAGAAACGCAGAACATGAGCGACGCTAT
 ^               ^ ^                                ^
 MnlI            DpnI                               NlaIII
                 MboI
                 Sau3A 2050      2060      2070      2080      2090      2100
     *         *         *         *         *         *
ACCTGTAGAAGAAGCCCAAATTGTCGAAACTGCCTTACTTGCAGCAGTAAATGACACTAG
 ^            ^ ^  ^                       ^              ^
```

FIG. 15G

```
        HgaI              EcoRI*TaqI              Fnu4HI      BbvI
                          MboII 2110          2120        2130        2140        2150        2160
         *             *           *           *           *           *
        TAAGGACGACCAAGCAATTGTTACTGACCTTATAAACGCTACAATAGAGGTGTGCACAGA
             ^             ^             ^                     ^

EcoRI*       Tth111II       MnlI                 Bsp1286
                                                              HgiAI 2170        2180        2190        2200        2210        2220
         *           *           *           *           *           *
        GCAGACTAATACACTTGCGGGGCATACTGCCGAGGTCCAAGCAGGGCTGGAAGCTGCGGG
                             ^           ^     ^               ^^^
                             MnlI     AvaII  BbvI            AluI
                                      Sau96I                 Fnu4HI
                                                             Tth111II 2230        2240        2250        2260        2270        2280
         *           *           *           *           *           *
        TATTAGATTCGACGATGCACAGGGACTACAAGAAGCTACCCCTGAAGCCAAGGGCGTGGA
         ^ ^^ ^                           ^                   ^
        EcoRI'                          AluI                BstXI
        HinfI                                               BstXI
        SfaNITaqI 2290        2300        2310        2320        2330        2340
         *           *           *           *           *           *
        AGGCATTAATCAAGAGGAACTCGAGCAGGCAGCTGAAGGTCTTGCTGCTGCTGTAAATGA
            ^            ^^       ^^^ ^        ^    ^   ^   ^
        MnlI         AvaI       AluI         BbvIFnu4HIMnlI
                     TaqI       BbvI                  Fnu4HI
                     XhoI        BbvI
                                Fnu4HI
                                PvuII 2350        2360        2370        2380        2390        2400
         *           *           *           *           *           *
        GGCTTCTGCAGATGGAAGATGCAGTCCCTCAATCAGCAGGAGACCCAGATTGCACAGGG
            ^^                   ^         ^
            PstI               MboII     MnlI
            SfaNI 2410        2420        2430        2440        2450        2460
         *           *           *           *           *           *
        AGAACAGCAGCAACAGCAGTCTTCTGGTTGGTCTAGGTAAACCGCTACCCTACCTTTAAC
           ^    ^     ^
        Fnu4HI   BbvI
```

FIG. 15H

```
        MboII 2470        2480        2490        2500        2510        2520
          *           *           *           *           *           *
    TGACACGGTGTAGATATGTCATGTAGAAGGAGCTCTGCCCCAATCAGGACGAAGTCCTTC
                          ^         ^ ^                  ^     ^
                        NlaIII    AluI                Tth111I
                                  BanII                 XmnI
                                  Bsp1286
                                  HgiAI
                                  SstI 2530        2540        2550        2560        2570        2580
          *           *           *           *           *           *
    ACAGGGAGCACAGCGCATCGTTGCTACCACAAATCGGGGGGTGCAAACCGCACTTCTTGC
      ^   ^ ^           ^                                 ^
    Bsp1286        SfaNI                                BbvI
    HgiAIHhaI
    HinPI 2590        2600        2610        2620        2630        2640
          *           *           *           *           *           *
    .AGAACCGCTGCAGTTGCCGTGCATTCAGCAAGAAGGGAGTATTGGTTTGCCGCCCGCCTC
         ^   ^                                                ^
       Fnu4HI                                              Fnu4HI
         PstI 2650        2660        2670        2680        2690        2700
          *           *           *           *           *           *
    GGTGAGTGGGTAGATGCGTTCCTTGCCAGTGTTGATGATGTCAATTGTAGCATTGCGCCA
      ^  ^     ^                                    ^        ^ ^
      MnlI  HphI                                EcoRI*     HhaI
    SfaNI                                                  HinPI 2710        2720        2730        2740
          *           *           *           *
    TCTGCGCATATTCGGCTTTTCGTTCGACGTTCAGAGGGTTGTTAAC
     ^^^              ^ ^              ^
     HhaI            MnlI            HincII
     HinPI           TaqI            HpaI
     MstI
```

FIG. 16A

```
              10         20         30         40         50.        60
               *          *          *          *          *          *
         G AGC TCG GGC CCC GTT CTG CGC ACG CGT CTG TGG ACC TTG CTG CGG GGC TGC TCT GTG 70         80         90        100        110        120
               *          *          *          *          *          *
         AGG CGA AAA TCG CCG GAC AGC CGA AAA TTT GGT GAA ATA AAG CAA TGC CGG GTG GCA TGT 130        140        150        160        170        180
               *          *          *          *          *          *
         TAA GAG CGC CTA ACC GGT TAT CAA GAC ATT GTT AAG TAG GTA GGT GCG ATG ACA GAA GAC
                                                                     Met Thr Glu Asp 190        200        210        220        230        240
               *          *          *          *          *          *
         GAC AAG CAA CAA CAG AAT CAA AGC GAT GTA GTA CAA GCC ATC TCG GCC GTA TTC CAG
         Asp Lys Gln Gln Gln Asn Gln Ser Asp Val Val Gln Ala Ile Ser Ala Val Phe Gln 250        260        270        280        290        300
               *          *          *          *          *          *
         CGC AAG AGT GCA GAG CTG CAG GGG CTG AAT GAC TTC ATA AAA GGC GCT GAT GGT ACA CTC
         Arg Lys Ser Ala Glu Leu Gln Arg Leu Asn Asp Phe Ile Lys Gly Ala Asp Gly Thr Leu 310        320        330        340        350        360
               *          *          *          *          *          *
         AAG AAC GTC CAT CCC CAC ATG AAG TCA CTG GAA GCG CTT TCT AAG CAA CTA TCA GAA AAG
         Lys Asn Val His Pro His Met Lys Ser Leu Glu Ala Leu Ser Lys Gln Leu Ser Glu Lys
```

FIG. 16B

```
        370         380         390         400         410         420
         *           *           *           *           *           *
ATT GCA GCT GAG GCA GCA GCG AAG GCA GAT GCT AAA TAC GAG AGC GTG GGA CTA CGT GCT
Ile Ala Ala Glu Ala Ala Ala Lys Ala Asp Ala Lys Tyr Glu Ser Val Gly Leu Arg Ala 430         440         450         460         470         480
         *           *           *           *           *           *
AAA GCA GCT GCA GCA TTA GGT AAT CTC GAC CAG CTT GTC GCC CGT GGT AAA CTC AAG AGC
Lys Ala Ala Ala Ala Leu Gly Asn Leu Asp Gln Leu Val Ala Arg Gly Lys Leu Lys Ser 490         500         510         520         530         540
         *           *           *           *           *           *
TCA GAT GCA CCC AAG GAC CTT GAC CAG AGC ATT GAC GCA CTA CCG TTC ATG GAT GAA GCA
Ser Asp Ala Pro Lys Asp Leu Asp Gln Ser Ile Asp Ala Leu Pro Phe Met Asp Glu Ala 550         560         570         580         590         600
         *           *           *           *           *           *
CCT GAC ACT GGT GAG AAG ATT GAA GTA CCA GCG GGT GAG GAG CAA GAA TTT GGC AAG GCA
Pro Asp Thr Gly Glu Lys Ile Glu Val Pro Ala Gly Glu Glu Gln Glu Phe Gly Lys Ala 610         620         630         640         650         660
         *           *           *           *           *           *
GCA GCT TGG GGT CTA GCA GGC TTC AAG CGT ACA GTG GAT GAA AGC CTG GAG ATG TTA GAC
Ala Ala Trp Gly Leu Ala Gly Phe Lys Arg Thr Val Asp Glu Ser Leu Glu Met Leu Asp 670         680         690         700         710         720
         *           *           *           *           *           *
CGA GGC ATG CAC ATG CTC GCG GAA GGC CAG GCA CAG ATA TCA CAG GGG ATT GAC GCC AAG
Arg Gly Met His Met Leu Ala Glu Gly Gln Ala Gln Ile Ser Gln Gly Ile Asp Ala Lys 730         740         750         760         770         780
         *           *           *           *           *           *
GAT ACT GCA CTA GTT AGG GAA GGT CTG GAA ACA TCT AGA CTT GGT GCA GGG TTA TGT CGC
Asp Thr Ala Leu Val Arg Glu Gly Leu Glu Thr Ser Arg Leu Gly Ala Gly Leu Cys Arg
```

FIG. 16C

```
     790          800          810          820          830          840
      *            *            *            *            *            *
AAT GGC TTG GTA GAG GCC TCC TAC GGC GTT GGT TAT GCC AAT GAG ACC ATG GGC AAG TAT
Asn Gly Leu Val Glu Ala Ser Tyr Gly Val Gly Tyr Ala Asn Glu Thr Met Gly Lys Tyr 850          860          870          880          890          900
      *            *            *            *            *            *
GCC AAG GGT CTA GAC AAG TGT AAA AAC AAA CTC GAC AAT GCA TGC CAC AAG TGG AGC
Ala Gly Lys Gly Leu Asp Lys Cys Lys Asn Lys Leu Asp Asn Ala Cys His Lys Trp Ser 910          920          930          940          950          960
      *            *            *            *            *            *
AAG GCT CTC GAA GAG ATT GAA AGC CTG CGC ACA GCA ATC GAC GCG AAG GCA GAA CAG CAA
Lys Ala Leu Glu Glu Ile Glu Ser Leu Arg Thr Ala Ile Asp Ala Lys Ala Glu Gln Gln 970          980          990         1000         1010         1020
      *            *            *            *            *            *
GTT GAA GGT GAA GCA TGG TCT CCT GAA GGG GTC AGT GCT AAC ACA TTC TAC AAA GGA CTG
Val Glu Gly Glu Ala Trp Ser Pro Glu Gly Val Ser Ala Asn Thr Phe Tyr Lys Gly Leu 1030         1040         1050         1060         1070         1080
      *            *            *            *            *            *
CAT AAA ATT GGC ACC GCA ATT GCA GCA GCT ACC CAA GCT ACC TGG GAA GGC TTG GCT ATG
His Lys Ile Gly Thr Ala Ile Ala Ala Ala Thr Gln Ala Thr Trp Glu Gly Leu Ala Met 1090         1100         1110         1120         1130         1140
      *            *            *            *            *            *
ACC GGT AAG TTC ATG GGT GCT GTA GCT AAA CTA GCT CTT AAA GCT GGT GCA TCC ATG TGC GTT GCA
Thr Gly Lys Phe Met Gly Ala Val Ala Lys Leu Ala Gly Ala Val Ser Met Cys Val Ala 1150         1160         1170         1180         1190         1200
      *            *            *            *            *            *
GCA TAC ACC GCA GCT ATC GTG GGT ATG GCC GCA GCT ACA CCT GCG ACG CTG CTG ACA
Ala Tyr Thr Ala Ala Ile Val Gly Met Ala Ala Ala Thr Pro Ala Thr Leu Leu Thr
```

FIG. 16D

```
         1210       1220       1230       1240       1250       1260
           *          *          *          *          *          *
GCT ATG GAC AAT CAA TCC GTA AAC AAT GCC GTA GTT AAA GTC AGT GAG TAC CTT CAC AGT
Ala Met Asp Asn Gln Ser Val Asn Asn Ala Val Val Lys Val Ser Glu Tyr Leu His Ser 1270       1280       1290       1300       1310       1320
           *          *          *          *          *          *
AAC GTA GAA CAA GCA ACT AAA GAC CTC ATG GCT TCA GAG TTT GCC ATG ATG ACA TTT GGT
Asn Val Glu Gln Ala Thr Lys Asp Leu Met Ala Ser Glu Phe Ala Met Met Thr Phe Gly 1330       1340       1350       1360       1370       1380
           *          *          *          *          *          *
GGC ATC ATG ACG TGT GCC AAG CTT ATG AAG GGC TCC TTC GCA GCA ATC AAT CAG AAG TTT
Gly Ile Met Thr Cys Ala Lys Leu Met Lys Gly Ser Phe Ala Ala Ile Asn Gln Lys Phe 1390       1400       1410       1420       1430       1440
           *          *          *          *          *          *
GAA ATC AAC GCC ACC CTC ACA CGG GAG GCC ACA GAC ATC GCT CAA GGG GTC AAG GAG
Glu Glu Ile Asn Ala Thr Leu Thr Arg Glu Ala Thr Asp Ile Ala Gln Gly Val Lys Glu 1450       1460       1470       1480       1490       1500
           *          *          *          *          *          *
ACT TAC CAG TCT ATT GGC GAT GCA TTT GGC AAT GCA TTC AAG TCT GTT GGC GAT GCA TTC
Thr Tyr Gln Ser Ile Gly Asp Ala Phe Gly Asn Ala Phe Lys Ser Val Gly Asp Ala Phe 1510       1520       1530       1540       1550       1560
           *          *          *          *          *          *
AAG TCT ATT GGC GAT GCA TTC AAG TCA GCT AAT GAT GGC ATA GCT AAG TGG ACA GCA GCT
Lys Ser Ile Gly Asp Ala Phe Lys Ser Ala Asn Asp Gly Ile Ala Lys Trp Thr Ala Ala 1570       1580       1590       1600       1610       1620
           *          *          *          *          *          *
CTA GCA GGT TAT GCG TCA GTT GAA CAG GTA GAA CAG AAG GAA GCA GAC AGG GTA CAG
Leu Ala Gly Tyr Ala Ser Val Glu Gln Leu Glu Glu Ala Lys Glu Ala Asp Arg Val Gln
```

FIG. 16E

```
              1630        1640        1650        1660        1670        1680
                *           *           *           *           *           *
         GCT GAG CAG CGA GCT GAA GCA CAA GCA ATG ACC GAG CGT GTG GCA GGG GAG CCT GCA GCA
         Ala Glu Gln Arg Ala Glu Ala Gln Ala Met Thr Glu Arg Val Ala Gly Glu Arg Ala Ala 1690        1700        1710        1720        1730        1740
                *           *           *           *           *           *
         ACA GTT GCT GCA GGG ACT GAA ACC ATT AAG ACC ATC GTC AGC GAT ATG CGG AAT GAG CTT
         Thr Val Ala Ala Gly Thr Glu Thr Ile Lys Thr Ile Val Ser Asp Met Arg Asn Glu Leu 1750        1760        1770        1780        1790        1800
                *           *           *           *           *           *
         GCT AAA GGG CAT GAA CAG CTT CAG CTC ATC ACC GAT ATG TGT AAT GAG CTT GCA CAA
         Ala Lys Gly His Glu Gln Leu Gln Leu Ile Thr Asp Met Cys Asn Glu Leu Ala Gln 1810        1820        1830        1840        1850        1860
                *           *           *           *           *           *
         ATA GGT GCA TTC TCC CAA GCA CGC GAT GCA CTT GTG AAG TCC TTC ACG CCT AAA CCT
         Ile Gly Ala Phe Ser Gln Ala Arg Asp Ala Leu Val Lys Ser Phe Thr Pro Lys Pro 1870        1880        1890        1900        1910        1920
                *           *           *           *           *           *
         CCT GCT AGG ACA ACC AAG GAG CTT ATC ATG TCA CAT ATG TCG GGC CTA GAA TCC GTG ATG
         Pro Ala Arg Thr Thr Lys Glu Leu Ile Met Ser His Met Ser Gly Leu Glu Ser Val Met 1930        1940        1950        1960        1970        1980
                *           *           *           *           *           *
         TTC CGT ATG GCA CGT AGT CTT GGG ATC ATG AGC AAA GCT AGT ATA GAG GCA AAC TCG CAG
         Phe Arg Met Ala Arg Ser Leu Gly Ile Met Ser Lys Ala Ser Ile Glu Ala Asn Ser Gln 1990        2000        2010        2020        2030        2040
                *           *           *           *           *           *
         GAC AAT AGT GTA GAG GTG GCA GAG ATC AGC CCA GAA ACG CAG AAC ATG AGC GAC GCT ATA
         Asp Asn Ser Val Glu Val Ala Glu Ile Ser Pro Glu Thr Gln Asn Met Ser Asp Ala Ile
```

FIG. 16F

```
         2050            2060            2070            2080            2090            2100
          *               *               *               *               *               *
CCT GTA GAA GAA GCC CAA ATT GTC GAA ACT GCC TTA CTT GCA GCA GTA AAT GAC ACT AGT
Pro Val Glu Glu Ala Gln Ile Val Glu Thr Ala Leu Leu Ala Ala Val Asn Asp Thr Ser 2110            2120            2130            2140            2150            2160
          *               *               *               *               *               *
AAG GAC GAC CAA GCA ATT GTT ACT GAC CTT ATA AAC GCT ACA ATA GAG GTG TGC ACA GAG
Lys Asp Asp Gln Ala Ile Val Thr Asp Leu Ile Asn Ala Thr Ile Glu Val Cys Thr Glu 2170            2180            2190            2200            2210            2220
          *               *               *               *               *               *
CAG ACT AAT ACA CTT GCG GGG CAT ACT GCC GAG GTC CAA GCA GGG CTG GAA GCT GCG GGT
Gln Thr Asn Thr Leu Ala Gly His Thr Ala Glu Val Gln Ala Gly Leu Glu Ala Ala Gly 2230            2240            2250            2260            2270            2280
          *               *               *               *               *               *
ATT AGA TTC GAC GAT GCA CAG GGA CTA CAA GAA GCT ACC CCT GAA GCC AAG GGC GTG GAA
Ile Arg Phe Asp Asp Ala Gln Gly Leu Gln Glu Ala Thr Pro Glu Ala Lys Gly Val Glu 2290            2300            2310            2320            2330            2340
          *               *               *               *               *               *
GGC ATT AAT CAA GAG GAA CTC GAG CAG CAG GCA GCT GGT CTT GCT GCT GTA AAT GAG
Gly Ile Asn Gln Glu Glu Leu Glu Gln Gln Ala Ala Gly Leu Ala Ala Val Asn Glu 2350            2360            2370            2380            2390            2400
          *               *               *               *               *               *
GCT TCT GCA GAT GGG AAG ATG CAG TCC CTC AAT CAG CAG GAG ACC CAG ATT GCA CAG GGA
Ala Ser Ala Asp Gly Lys Met Gln Ser Leu Asn Gln Gln Glu Thr Gln Ile Ala Gln Gly 2410            2420            2430            2440            2450            2460
          *               *               *               *               *               *
GAA CAG CAG CAA CAG CAG TCT TCT GGT TGG TCT AGG TAA ACC GCT ACC CCT TTA ACT
Glu Gln Gln Gln Gln Gln Ser Ser Gly Trp Ser Arg ---
```

FIG. 16G

```
              2470        2480        2490        2500        2510        2520
               *           *           *           *           *           *
     GAC ACG GTG TAG ATA TGT CAT GTA GAA GGA GCT CTG CCC CAA TCA GGA AGT CCT TCA 2530        2540        2550        2560        2570        2580
               *           *           *           *           *           *
     CAG GGA GCA CAG CGC ATC GTT GCT ACC ACA AAT CGG GGT GTG CAA ACC GCA CTT CTT GCA 2590        2600        2610        2620        2630        2640
               *           *           *           *           *           *
     GAA CCG CTG CAG TTG CCG TGC ATT CAG CAA GAA GGG AGT ATT GGT TTG CCG CCC GCC TCG 2650        2660        2670        2680        2690        2700
               *           *           *           *           *           *
     GTG AGT GGG TAG ATG CGT TCC TTG CCA GTG TTG ATG ATG TCA ATT GTA GCA TTG CGC CAT 2710        2720        2730        2740
               *           *           *           *
     CTG CGC ATA TTC GGC TTT TCG TTC GAC GTT CAG AGG GTT GTT AAC
```

FIG. 16H

| Codon | AA | Count | % | Codon | AA | Count | % | Codon | AA | Count | % | Codon | AA | Count | % |
|---|---|---|---|---|---|---|---|---|---|---|---|---|---|---|---|
| TTT | Phe | 5 | .7% | TCT | Ser | 10 | 1.3% | TAT | Tyr | 3 | .4% | TGT | Cys | 4 | .5% |
| TTC | Phe | 14 | 1.9% | TCC | Ser | 8 | 1.1% | TAC | Tyr | 6 | .8% | TGC | Cys | 3 | .4% |
| TTA | Leu | 4 | .5% | TCA | Ser | 8 | 1.1% | TAA | --- | 1 | --- | TGA | --- | 0 | --- |
| TTG | Leu | 2 | .3% | TCG | Ser | 3 | .4% | TAG | --- | 0 | --- | TGG | Trp | 6 | .8% |
| CTT | Leu | 16 | 2.1% | CCT | Pro | 8 | 1.1% | CAT | His | 6 | .8% | CGT | Arg | 7 | .9% |
| CTC | Leu | 11 | 1.5% | CCC | Pro | 2 | .3% | CAC | His | 4 | .5% | CGC | Arg | 4 | .5% |
| CTA | Leu | 11 | 1.5% | CCA | Pro | 2 | .3% | CAA | Gln | 21 | 2.8% | CGA | Arg | 2 | .3% |
| CTG | Leu | 11 | 1.5% | CCG | Pro | 1 | .1% | CAG | Gln | 29 | 3.8% | CGG | Arg | 4 | .5% |
| ATT | Ile | 15 | 2.0% | ACT | Thr | 10 | 1.3% | AAT | Asn | 19 | 2.5% | AGT | Ser | 8 | 1.1% |
| ATC | Ile | 12 | 1.6% | ACC | Thr | 13 | 1.7% | AAC | Asn | 9 | 1.2% | AGC | Ser | 11 | 1.5% |
| ATA | Ile | 8 | 1.1% | ACA | Thr | 17 | 2.2% | AAA | Lys | 14 | 1.9% | AGA | Arg | 2 | .3% |
| ATG | Met | 26 | 3.4% | ACG | Thr | 4 | .5% | AAG | Lys | 35 | 4.6% | AGG | Arg | 4 | .5% |
| GTT | Val | 9 | 1.2% | GCT | Ala | 37 | 4.9% | GAT | Asp | 16 | 2.1% | GGT | Gly | 21 | 2.8% |
| GTC | Val | 9 | 1.2% | GCC | Ala | 17 | 2.2% | GAC | Asp | 23 | 3.0% | GGC | Gly | 21 | 2.8% |
| GTA | Val | 16 | 2.1% | GCA | Ala | 61 | 8.1% | GAA | Glu | 39 | 5.2% | GGA | Gly | 4 | .5% |
| GTG | Val | 9 | 1.2% | GCG | Ala | 9 | 1.2% | GAG | Glu | 31 | 4.1% | GGG | Gly | 12 | 1.6% |

IMMUNOGENIC ANAPLASMA MARGINALE SURFACE ANTIGENS, COMPOSITIONS, AND METHODS OF USE

CROSS REFERENCES TO RELATED APPLICATIONS

This application is a continuation of application Ser. No. 08/079,971, filed Jun. 18, 1993, now abandoned, which is a continuation of application Ser. No. 07/875,554, filed Apr. 27, 1992, now abandoned, which is a continuation of application Ser. No. 07/335,178, filed Apr. 6, 1989, now abandoned, which is a continuation-in-part of application Ser. No. 253,143, filed Oct. 4, 1988. This is also a continuation-in-part of application Ser. No. 141,505, filed Jan. 7, 1988; which was a continuation of application Ser. No. 761,178, filed Jul. 31, 1985 (now abandoned); which in turn was a continuation-in-part of application Ser. No. 715,528, filed Mar. 25, 1985 (now abandoned). This is further a continuation-in-part of application Ser. No. 245,855, filed Sep. 16, 1988, abandoned.

FIELD OF THE INVENTION

The present invention primarily relates to antigenic polypeptides and proteins, related vaccines and methods useful to induce an immune response which is protective to reduce the severity or prevent infection by rickettsial parasites of the order Rickettsiales, family Rickettsia, more particularly rickettsiae (or rickettsias) of the genus Anaplasma, even more particularly rickettsias of the species *Anaplasma marginale*.

BACKGROUND OF THE INVENTION

Rickettsiae are very small parasitic microorganisms (approximately 0.2 micron) which are of the taxonomical order Rickettsiales, family Rickettsia. Rickettsial diseases caused by these parasites have been very significant throughout history to both humans and animals. Human deaths caused by outbreaks of epidemic typhus and scrub typhus number in the millions. Epidemic typhus is caused by the rickettsia *Rickettsia prowazeki*. Scrub typhus is caused by the rickettsia *Rickettsia tsutsugamushi* which is still endemic in many rural areas of Southeast Asia and Japan. Rocky Mountain spotted fever, caused by *Rickettsia rickettsii*, is widespread in the eastern United States and is a risk in many other parts of the country.

Animal diseases caused by rickettsiae include Rocky Mountain spotted fever and canine ehrlichiosis, caused by *Ehrlichia canis*, both of which afflict dogs. Rickettsial diseases of horses include equine ehrlichiosis, caused by *Ehrlichia equis*, and Potomac fever, caused by *Ehrlichia risticii*. Serious losses occur to cattle from the rickettsia *Anaplasma marginale*. Some animal rickettsial diseases are communicable to humans, for example, Q-fever, canine ehrlichiosis and Potomac fever. Despite the widespread significance of rickettsial diseases, little has been known about the molecular biology of the rickettsiae.

Anaplasmosis is an arthropod borne hemoparasitic disease of cattle and other ruminants caused by *Anaplasma marginale*. Anaplasmosis occurs worldwide and severely constrains livestock production in tropical and subtropical regions. This rickettsia is transmitted by ticks, biting flies, and blood contaminated fomites to susceptible animals, where it infects red blood cells (erythrocytes). *Anaplasma marginale* occurs in the red blood cells as an intraerythrocytic initial body, which is a single *Anaplasma marginale* organism in a mature infective stage of the microbe's life cycle. The infective initial bodies reproduce by binary fission within the erythrocytes to form two to eight initial bodies which are subsequently released to infect additional erythrocytes.

During acute infection the level of these parasites increases geometrically and severe extravascular anemia occurs. Marked weight loss, abortion, and death can occur during the acute crisis caused by this parasitic infection and the resultant parasitemia. Animals that recover from the acute infection remain persistently infected and are a reservoir for transmission to susceptible animals.

Current immunoprophylaxis for anaplasmosis includes premunization with a less virulent *Anaplasma marginale* isolate or *Anaplasma centrale*, a less virulent anaplasma species. Premunization is typically followed by tetracycline treatment to control severe infection in some animals. Another immunoprophylatic approach is vaccination with a vaccine containing killed whole *Anaplasma marginale* organisms and host erythrocyte stroma. Premunition is successful in controlling severe clinical disease when cattle are challenged with a virulent isolate. However, clinical disease including weight loss, abortion and occasionally death may result from premunizing inoculum. This inoculum may also transmit other hemoparasites, such as Babesia, Theileria, and Trypanosoma, and viruses, such as leukemia virus, to the animal being treated. Challenge of cattle immunized with the killed *Anaplasma marginale*-erythrocyte stroma vaccine results in mild clinical disease and persistent infection. In addition, the presence of erythrocyte stroma in the vaccine has been shown to induce anti-erythrocyte antibodies which can be transferred through a cow's colostrum to a nursing calf thus causing the autoimmune disease neonatal isoerythrolysis.

Accordingly, there remains a strong need for improved immunization techniques effective against these and other rickettsial diseases. There also remains a continuing need for relatively simple diagnostic tests for detecting carriers of rickettsial parasites.

BRIEF DESCRIPTION OF THE DRAWINGS

Drawings showing Figs. which relate to preferred embodiments of this invention are included herewith, and are briefly described as set forth below.

FIGS. 10A–10F, 1–2 is a sequence diagram showing DNA nucleotide sequences for the Florida, Virginia, Idaho and Washington isolates of *Anaplasma marginale*, including the genes which code for the expression of the MSP-1a or Am105U protein.

FIG. 11B is a sequence diagram showing portions of the DNA nucleotide sequences shown in FIG. 10 for the promoter regions of the four geographical isolates of *Anaplasma marginale* and E. coli.

FIGS. 12A and 12B are sequence diagrams showing amino acid sequences for the MSP-1a (Am105U) proteins expressed by the four different geographical isolates of *Anaplasma marginale*.

FIG. 13 is a sequence diagram comparing portions of the amino acid sequences shown in FIG. 12. The sequences shown in FIG. 13 indicate repeat patterns of five different types labeled A–E. The number of times that a particular repeat pattern is included in the protein is indicated in the chart shown at the right of FIG. 13.

FIG. 14 shows a number of synthesized polypeptide sequences and whether such sequences in vitro reacted with monoclonal antibody $22B_1$.

FIGS. 15A–15H, 1–8 is a restriction enzyme map showing the cut sites for a number of restriction enzymes upon the DNA nucleotide sequence containing the gene coding for the expression of the *Anaplasma marginale* protein Am105L for the Florida isolate.

FIGS. 16A–16H, 1–5 is a sequence diagram showing the DNA nucleotide sequence for the gene coding for the expression of the *Anaplasma marginale* protein Am105L. Also shown is the corresponding amino acid sequence of protein Am105L of the Florida isolate.

SUMMARY OF THE INVENTION

Figure 1A:
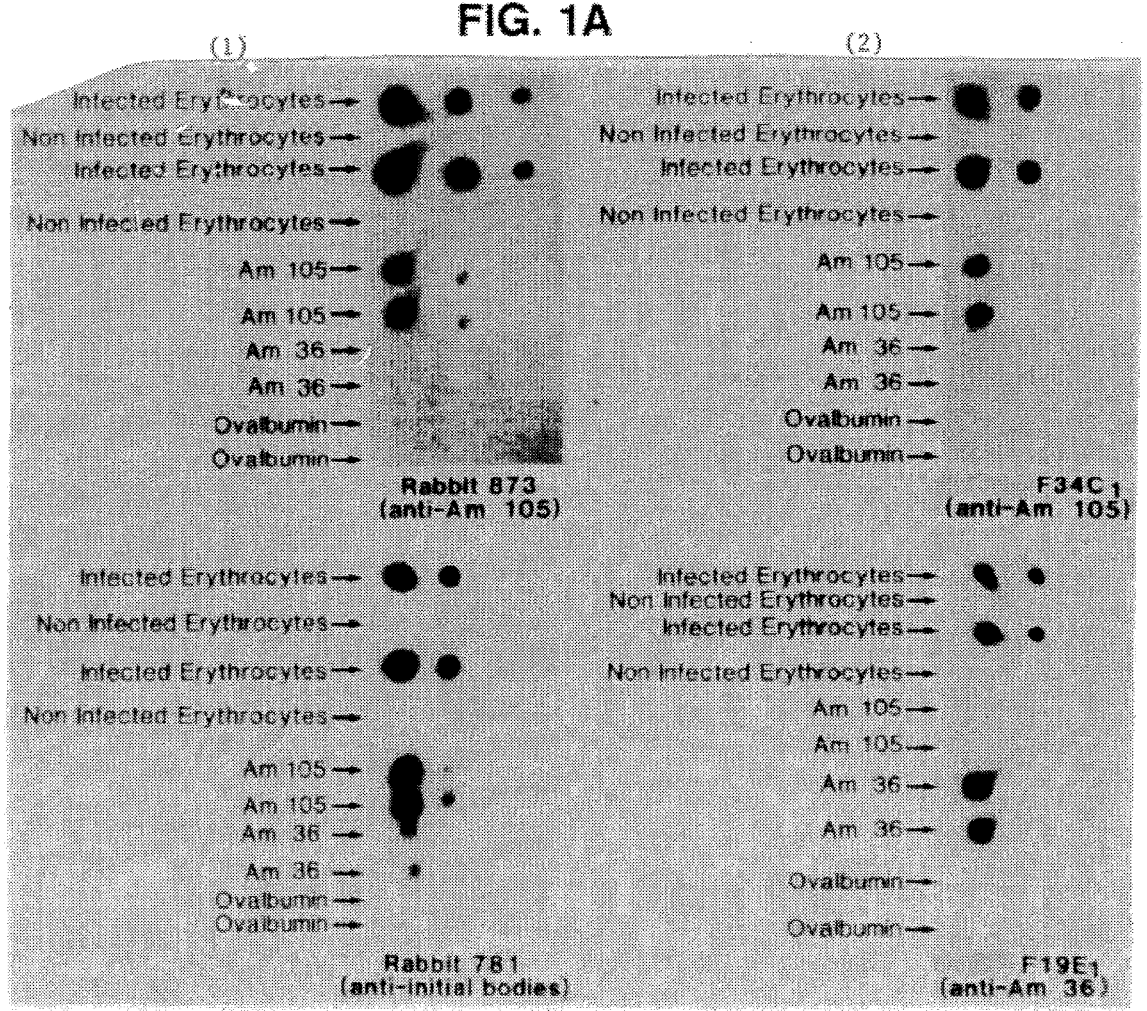
FIG. 1A is a reproduction of four radiographs (1)–(4) showing the detection of native *Anaplasma marginale* proteins on nitrocellulose using four different types of antibody or antiserum.

The present invention seeks to overcome some of the limitations of the prior art by providing improved antigens and immunogens for detecting and immunizing relative to rickettsial parasites, in particular *Anaplasma marginale*. The invention includes suitable purified antigens which are bound by serum antibodies, and which are in at least some cases immunogenic to reduce the severity or prevent infection by *Anaplasma marginale* and other rickettsial organisms having epitopes of the same or sufficiently similar nature. The invention also includes certain monoclonal antibodies which can selectively bind antigenic components of rickettsias such as *Anaplasma marginale*, and provide detection and other valuable screening and diagnostic uses.

Selected native proteins can be isolated from *Anaplasma marginale* organizisms and purified or treated to produce one or more purified immunogenic polypeptides or proteins. The invention includes the discovery that at least one native antigen having surface-exposed epitopes is common to numerous geographical isolates of *Anaplasma marginale* in forms which share conserved polypeptide sequences. This protein complex has been identified and purified, and is alternatively referred to a major surface protein 1 (MSP-1) and Am105. The two component proteins of this complex are referred to as Am105U and Am105L. In at least one of the geographically distinct isolates of *Anaplasma marginale* these complexed proteins have electrophoretic mobilities which correspond to approximate molecular weights of about 105,000 daltons. In other isolates the electrophoretic mobilities and apparent molecular weights of these two complexed proteins vary, particularly with respect to one of the two complexed proteins.

Other antigenic proteins have been identified from *Anaplasma marginale* organisms and are characterized by electrophoretic mobilities which correspond to apparent molecular weights of about 86,000 daltons (Am86); 61,000 daltons (Am61); 36,000 daltons (Am36); and 15,000 daltons (Am15). Still other antigenic proteins as identified herein are also of use in this invention.

In addition to the native proteins isolated and purified from *Anaplasma marginale*, the antigens and immunogens according to this invention can comprise active agents formed of one or more such proteins, polypeptide fragments of such proteins, or one or more immunologically similar proteins or polypeptides produced by polypeptide synthesis or genetic engineering.

Several forms of novel antigens of this invention have been produced by recombinant DNA techniques coding for the expression of recombinant antigens which have demonstrated immunogenic effect. Amino acid sequences have been identified which characterize at least some of the effective antigens and immunogens of this invention.

Antigenic proteins of the invention are in part purified by removing or isolating *Anaplasma marginale* initial bodies from cellular components of the infected erythrocytes. The significantly purified initial bodies are thereafter disrupted, such as by using a suitable detergent or by other means. Desired antigens can be purified from the disrupted *Anaplasma marginale* organisms, such as by passing the disrupted initial bodies over antibodies which selectively bind the desired antigens. Such can be accomplished by passing an aqueous mixture containing the disrupted initial bodies over or through an insoluble matrix, such as an affinity chromatography column. The insoluble matrix has monoclonal antibodies specific to the desired antigenic protein or peptide which recognize one or more epitopes thereon to adsorb it onto the insoluble matrix. The adsorbed antigens are further purified by washing the non-adsorbed materials of the aqueous initial body mixture through the affinity chromatography column to leave the adsorbed antigens bound to the matrix. The adsorbed antigens are recovered from the matrix to provide purified antigens according to this invention.

The novel monoclonal antibodies preferably used to prepare the purified antigens, are advantageously prepared by vaccinating or otherwise inoculating mice with the appropriate rickettsial parasites, such as by injecting the mice with bovine erythrocytes infected with *Anaplasma marginale*. Lymphocytes are taken from the spleen of the infected mice. The lymphocytes from the mice are fused with immortal cells, such as myeloma cells, to produce hybridoma cells which are cloned to develop hybridoma cell lines. Some of the hybridoma cell lines produce monoclonal antibodies which will selectively bind to the desired antigens. The collection of hybridoma cell lines are then screened using a novel approach to identify the hybridomas of interest.

The screening of the hybridomas can advantageously initially include procedures for detecting the hybridomas which produce antibodies which bind to *Anaplasma marginale*. This is advantageously accomplished by indirect immunofluorescence on smears of *Anaplasma marginale*-infected blood. The hybridomas are then further screened to determine those which produce monoclonal antibodies against specific *Anaplasma marginale* proteins, such as by immunoprecipitation of selected proteins of *Anaplasma marginale* by the cell line supernatants containing the monoclonal antibodies. In particular are selected those hybridomas producing antibodies which selectively bind *Anaplasma marginale* proteins having surface-exposed epitopes, more particularly epitopes also bound by immune serum of an animal previously infected by the parasites.

Additional amounts of the desired monoclonal antibodies are advantageously produced by collection of ascitic fluid from mice inoculated with the selected hybridoma cell lines. Such a monoclonal antibody collected from murine ascitic fluid is appropriately purified, such as by precipitation, dialysis and chromatography. The purified monoclonal antibody is then coupled to an insoluble matrix such as Sepharose to prepare an immunoaffinity matrix. Partially purified disrupted rickettsial organisms, such as *Anaplasma marginale* initial bodies, are then passed through the immunoaffinity matrix and the desired antigenic protein is selectively adsorbed onto the matrix. The purified protein which has adsorbed onto the matrix is then appropriately removed or otherwise recovered from the matrix to provide significant amounts of the desired antigen in a sufficiently purified form to serve effectively in the indicated uses for this invention.

The degree of purity of the proteins achieved in accordance with the present invention is dependent upon the method of production used. The purity of native proteins and polypeptides derived therefrom is significantly higher than the purity of the antigen in its natural state. As an example, in its natural state Am105 is believed to be present in an amount of about 0.1 to 1% of the total protein present in the initial bodies. In its natural state, many other impurities such as about 200 other proteins, carbohydrates, red cells, glycoproteins, and nucleic acid are present. However, the Am105 can be purified to significantly higher levels of purity using the methods taught herein. Purity levels of approximately 10% by weight or higher are believed operable. Purity levels of 20% by weight or higher are more preferred. Still more preferred are purity levels of 50% by weight or higher. The purification techniques taught herein are capable of producing purity of at least 90 weight percent, preferably at least 95 weight percent and most preferably at least 98 weight percent. The purified Am105 has a molecular weight of about 105,000 daltons as measured by electrophoretic mobility analysis but significantly less when molecular weight is determined by DNA and amino acid sequence information as presented herein. Other antigens according to this invention are expected to also show significant differences between molecular weight measured by electrophoretic mobility versus sequenced information. Nonetheless the electrophoretic mobility information provides a valid means for identifying and isolating the antigens according to this invention.

One of the demonstrated immunogenic antigens of this invention, Am105 (Florida isolate), is reactive with monoclonal antibodies produced by hybridomas cell lines ANA 15D2 and ANA 22B1. Deposits of cell lines ANA 15D2 and ANA 22B1 have been made in the American Type Culture Collection of 12301 Parklawn Drive, Rockville, Md. 20852, United States of America, under ATCC Nos. HB9046 and HB9047, respectively. The deposits of these cell lines were made in accordance with the terms of the Budaoesr Treaty in Mar. 19, 1986.

The immunoaffinity purified antigens of this invention such as Am105, and the recombinant or artificially synthesized peptides as taught herein are most preferably substantially free of contaminating glycoproteins, carbohydrates, red cells, and nucleic acids.

Active fragments or subunits of the identified antigenic polypeptides of this invention may be effective in inducing immunity to *Anaplasma marginale* or other rickettsial organisms. Effectiveness of at least some of the antigens has been demonstrated in cattle. The size of the active fragment(s) may be as small as six to twenty or possibly six to ten amino acids.

The antigens according to this invention can be produced by immunoaffinity chromatography as described above and elsewhere herein, or using artificial methods of polypeptide synthesis, or using genetic engineering with expression of the desired peptide(s) or protein(s). Various methods for producing polypeptides by artificial synthesis are known in the art and will not be described herein because of the well-known effectiveness of such methods in generating polypeptides with a known amino acid sequence. Reference can be made to commercial services and many scientific writings for examples of one of many suitable techniques for such synthesis. Since such techniques require knowledge of the desired amino acid sequence(s) of the polypeptide sought, the novel teachings contained herein will enable a variety of different synthetic antigens and immunogens to be produced for use in this invention.

The invention further includes certain novel genetically engineered DNA and RNA sequences and microorganisms incorporating such sequences which have been produced for the purposes of analyzing and expressing the novel antigens according to this invention. Such recombinant microorganisms were advantageously produced by creating a pseudo-random genomic library of recombinant bacteria, such as *E. coli*, which incorporate novel recombinant DNA plasmids. The recombinant plasmids incorporate DNA fragments from the genome of an appropriate rickettsial parasite, such as *Anaplasma marginale*. The recombinant DNA plasmids were created by cleaving plasmid DNA with a suitable restriction enzyme. Similarly, *Anaplasma marginale* DNA is cleaved with suitable restriction enzymes to produce a large number of various *Anaplasma marginale* DNA fragments. The DNA strands from the plasmids and *Anaplasma marginale* were mixed to join fragments of each and then ligated to form recombinant plasmid vectors. The recombinant plasmid vectors were implanted into suitable hosts, *E. coli*, and cloned to produce a collection of recombinant bacterial cell lines. The resulting recombinant cell lines were screened for the expression of desired antigens, such as by using selected monoclonal antibodies against the parasites, as described above and elsewhere herein. Alternatively, viruses such as vaccinia virus can be used to produce recombinant viral vectors bearing nucleic acid sequences coding for the expression of the desired antigens. Recombinant RNA can alternatively, be produced to code for the expression of the desired antigens.

Recombinant bacterial cell lines were developed which express antigenic recombinant proteins which mimic the surface-exposed native proteins contained in the protein complex alternatively called MSP-1 and Am105. The invention also includes the discovery that the native proteins contained in this complex are polymorphic between different geographical isolates of *Anaplasma marginale* varying in size and amino acid sequences. Recombinant plasmids containing *Anaplasma marginale* DNA were analyzed to determine the DNA sequences associated with the expression of these related polymorphic proteins. The antigens expressed by these four geographical isolates were also analyzed to determine the amino acid sequences. The antigens were found to have a hypervariable domain of variable numbers of tandemly repeated sequences at the N end of the polypeptide. The tandem repeats consisted of polypeptides of 28 or 29 amino acids. The number of repeats varied between 2 and 8 within the group of 4 different isolates analyzed. However, all of the tandem repeats in the four isolates were found to possess conserved amino acid sequences. Monoclonal antibodies which bind to surface-exposed epitopes of *Anaplasma marginale* and are effective at neutralizing the infectivity of such organisms also bind to at least some of the conserved epitopes contained in the tandem repeat regions of the proteins.

Novel recombinant cell lines have been developed which express proteins including the tandem repeat polypeptide sequences. Such novel recombinant-produced proteins containing the conserved polypeptide sequences have been demonstrated to cause an immune response in cattle which is effective to reduce the severity or prevent acute infection by *Anaplasma marginale*. Other antigens bound by selected monoclonal antibodies which are reactive with *Anaplasma marginale*, particularly those reactive with epitopes shown to cause neutralization of the infectivity of the parasites, are also within the scope of this invention.

The immunogenic antigens according to this invention can be used in vaccines to bring about an immune response effective to reduce the severity or prevent infection by rickettsial organisms. Such antigens should be present in a single dose of the vaccine in an amount of approximately 1–1000 micrograms, preferably 5–400 micrograms, and most preferably 10–200 micrograms. A single injectable dose will usually have a volume of about 1–2 milliliters. Therefore the concentration of purified surface antigen in an injectable vaccine composition will usually be in the range of from about 1 to about 500 micrograms/milliliter and preferably about 5 to about 200 micrograms/milliliter and most preferably 10–500 micrograms/milliliter. The antigens can advantageously be dissolved or otherwise administered with an adjuvant, such as Freund's complete and/or incomplete adjuvants.

The vaccine, in addition to containing the purified antigens and optionally an adjuvant, may also contain any other suitable is pharmaceutically acceptable carrier or diluent. The pharmaceutically acceptable carrier or diluent is a compound, composition or solvent which is preferably a non-toxic sterile liquid useful for administration of the active antigens or in some cases otherwise increasing the effectiveness of the inoculation treatments.

In order to immunize ruminants, preferably young animals are inoculated with a vaccine comprising the purified antigens and any desired adjuvants and diluents. The antigens can be purified from the parasites, produced as expressed polypeptides or proteins from recombinant cells, or produced by artificial polypeptide synthesis. Such purified antigens are preferably added to a suitable pharmaceutically acceptable carrier or diluent, and any desired adjuvant(s). Preferably, the animals are successively inoculated with a single dose as defined above at one to six week intervals, preferably two to four week intervals about two to eight times, preferably three to five times. The purified protein(s) or polypeptide(s) should be present in the vaccine in an amount(s) effective to induce an immune response in the animals being treated. Such immune response is preferably sufficient to protect the vaccinated animals so that if subsequently challenged with virulent rickettsias, such as *Anaplasma marginale*, the degree of acute infection is substantially reduced or even prevented. Injection will usually be performed intramuscularly (i.m.) or subcutaneously (s.c.).

The purified recombinant, synthesized, or native polypeptides and proteins defined herein also are useful in diagnostic tests to determine whether an animal is infected by an applicable rickettsial parasite, such as *Anaplasma marginale*. Conversely, such diagnostic tests may also incorporate one or more of the monoclonal antibodies specific to infection by such organisms. The diagnostic tests are advantageously immunoassays, such as one or more types of enzyme linked immunosorbent assays, such as for serologic diagnosis of anaplasmosis. Alternatively, the assays can be radioimmunoassays or others utilizing the selective binding of the purified antigens to antibodies raised in an infected animal, or monoclonal antibodies which specifically bind antigens associated with the particular parasitic organisms of interest. When samples from subject animals are tested using such antigens and/or antibodies, results distinguishing infected and non-infected animals are obtainable.

The discovered DNA sequence information can be used to create novel nucleic acid sequences which are useful as a nucleic acid probe which can be labelled and used to detect for the presence of hybridizing DNA or RNA, to provide a diagnostic test of great sensitivity.

DETAILED DESCRIPTION OF THE INVENTION

The detailed description of this invention is broken into subparts to aid in the understanding of the large amount of complex material contained herein.

PART I—MONOCLONAL ANTIBODIES AND IMMUNOAFFINITY

PURIFIED ANTIGENS

Preparation of Monoclonal Antibodies to *Anaplasma marginale*

The source of antigen, mouse immunization protocol, myeloma cell lines used, culture media and conditions, and cell fusion and cloning are described in Davis et al, Development of monoclonal antibodies to *Anaplasma marginale* and preliminary studies on their application. Proc. Seventh National Anaplasmosis Conf. Oct. 21–23, 1981, Mississippi State University Press. The procedure can be summarized as follows.

Animals—Young Hereford and Holstein cattle were used. Animals to be infected with *Anaplasma marginale* were splenectomized. Two inbred strains of mice, BALB/c and B10.A(3r), were used as a source of cells to make hybridomas. These and additional strains, B10.A, B10.A(5R) and B10.A(2R), were used as a source of thymocytes for co-culture as feeder cells with hybridoma cells.

Preparation of *Anaplasma marginale*-infected erythrocytes

Splenectomized cattle were infected with an Idaho isolate of A. Marginal as described in Davis, W. C. et al, Infect. Immun. 22:597–602 (1978). For tissue culture studies, blood was collected in heparin every two to four days after infection. Blood smears were made and stained with Wright's-Giemsa stain and examined for anaplasma bodies. When parasitemia reached 20–50%, blood was collected, centrifuged, freed of ∠the buffy coat and then frozen in 30% dimethylsulfoxide (DMSO) for later use. Additional blood smears were prepared and frozen at −70° C. until used to detect monoclonal antibodies.

Preparation of antigen and immunization—Two types of preparations were used as a source of antigen. In the first, frozen cells (50% packed cell volume) with a parasitemic of 30% were thawed and then immediately lysed with Tris (0.01M) ammonium chloride (0.87%) solution (pH 7.2). The lysate was centrifuged at 800 rpm for minutes; the pellet was washed 3 times in Hanks Balanced Salt Solution (HBSS) and resuspended in 10 ml of HBSS. Six mice [B10.A(3R)] were injected intraperitoneally (i.p.) with 1 ml of lysate. Three days before the spleens were taken for cell fusion, the mice were given an intravenous booster injection of 0.2 ml of lysate. The second preparation, a lysate of infected erythrocytes, was purified on a Renografin density gradient (25–55%) as described in Davis, N. C. et al, Infec. Immun. 22:597–602 (1978). The bands containing anaplasma bodies and contaminating erythrocyte stroma were collected and washed, as described above, then resuspended in 10 ml of HBSS. Five BALB/c mice were injected intraperitoneally with 1 ml for primary immunization and intravenously with 0.2 ml for booster immunization as described. All mice were immunized at least three weeks before receiving a booster injection.

Myeloma cell lines used to produce hybridomas—Several HAT (hypoxanthine, aminopterin and thymidine)-sensitive, tissue-culture-adapted mouse myeloma cell lines were used as fusion partners in the production of antibody producing hybridomas. NS1, a cell line that produces, but does not secrete K light chains, Oi et al, V.T., In Selected Methods in Cellular Immunology (Eds.) B. B. Mishell and S. M. Shiigi, W. H. Freeman and Co., pp. 351–372 (1980) and SP2/O-Ag14, a cell line derived from a Nsl-BALB/c hybrid that synthesizes neither light or heavy chains, Schulman, M. et al, Nature, 276:279 (1978) were obtained from the Salk Institute. X63-Ag8.653, another cell line that does not produce light or heavy chains, Kearney, J. F. et al, J. Immunol123:1548–1550 (1979) was provided by M. Lostrum from the Fred Hutchinson Cancer Research Center, Seattle, Wash.

Culture media and culture conditions—Dulbecco's Modified Eagle Medium (DMEM), containing 13% fetal calf serum (FCS), $5\times10^{-5}$M 2-mercaptoethanol (2ME), penicillin (100 units/ml) and streptomycin (100 g/ml), was the primary culture medium for maintaining the myeloma cell lines and the new hybridoma cell lines. Glutamine (2 mM) was added when the medium was used 14 days after preparation. Fusion and transfer media were prepared by adding HAT and HT (hypoxanthine and thymidine), respectively, according to the method of Littlefield, Monoclonal Antibodies-Hybridomas: A New Dimension of Biological Analysis (Eds.) Kennett, R. H. et al, Plenum Press, pp. 363–416 (1981). RPMI-1640 containing 15% FCS and penicillin/streptomycin was used to culture anaplasma infected erythrocytes, Davis W. C. et al, Infect. Immun. 22:597–602 (1978). All cultures were maintained in a 5% $CO_2$ gas-air mixture at 37° C.

Cell fusion and cloning—Methods for fusing spleen and myeloma cells were similar to those described by Oi et al, supra. Myeloma cells were maintained in log phase of growth in T75 flasks by removing excess cells and feeding every 3 to 4 days. The day before fusing, cells were collected, washed by centrifugation and plated in T75 flasks at $1\times10^7$ cells per flask. On the day of use, cells were collected, centrifuged and resuspended in DMEM without FCS. Mice are immunized by injecting disrupted bovine erythrocytes which contain *Anaplasma marginale* initial bodies. Spleen cells were obtained from the freshly-killed, immunized mice by injecting the spleen with DMEM, gently tearing it apart with tweezers and then pressing it through a 100 mesh screen into a 50 ml test tube. Following removal of particulate debris, the cells were centrifuged into a pellet and the medium removed. Contaminating mouse erythrocytes were selectively lysed by brief exposure to distilled water (2 ml) and the spleen cells were then quickly diluted in DMEM. Thymocytes to be used as feeder were collected as above (but without water lysis) and suspended in DMEM-FCS-HAT at $1\times10^7$ cells per ml. Myeloma cells and spleen cells were counted, then mixed either at a ratio of 5 or 2.5 spleen cells to 1 myeloma cell. Usually, $10^8$ spleen cells were mixed with 2 or $4\times10^7$ myeloma cells. The cell mixture was sedimented and the supernatant removed. One ml of a 50% solution of polyethylene glycol (PEG 1540, Baker Chemical Co.) was then placed over the cell pellet and slowly mixed with the cells so as to form a slurry of small (1 $mm^3$) clumps of cells. Following 3 minutes of mixing, the cells were slowly diluted by adding 10 ml DMEM in 10 minutes and 20 ml over the next 5 minutes. The resultant mixture of fused cells was centrifuged into a pellet and the cells were resuspended in DMEM-FCS-HAT. Thymocytes were then added to give a mixture containing $10^8$ spleen cells, tumor cells and $1\times10^9$ thymocytes. Cells were distributed in ten 96-well culture plates and placed in the incubator. One half the tissue culture medium was replaced every 3 to 4 days. When clones of hybridomas were 300–1000 cells in size (usually by 12–18 days), the supernatants were collected and tested by indirect immunofluorescence on smears of infected erythrocytes. Cells from positive wells were identified and transferred to 24-well (2ml) culture plates. Three to $5\times10^6$ thymocytes were added as feeder cells to support growth. At 14 days or when the cultures needed to be thinned, the medium was replaced with DMEM-FCS-HT. The cells were maintained in static cultures (1 week in DMEM-FCS-HT then on DMEM-FCS) for two weeks by removing excess cells and feeding every 2–4 days, depending on the rate of replication of individual clones. At this time, a duplicate plate was prepared and allowed to overgrow. The supernatants from this plate were tested for antibody activity. All cell lines identified as antibody producers by this procedure were then taken from the master plate and expanded into 6 well plates (5 ml capacity in each well) as single cultures, 3 wells per cell line. Cells were collected twice and frozen (3–$10\times10^6$ cells in 10% DMSO) in liquid nitrogen. The remaining cells were allowed to proliferate and die. The supernatants were then collected (approximately 15 ml) and frozen for subsequent analysis.

When cell lines producing antibody of immediate interest were identified, they were taken from the freezer, thawed and cloned by limiting dilution immediately or following 24-hrs. culture. Usually, hybridoma cells were plated in 2 to 6 96-well plates, 3 cells per well in the presence of $10^6$ thymocytes. Wells containing single colonies were identified microscopically and supernatants were collected and tested for antibody activity. Cells from positive wells were transferred as above to 24-well plates and then to 6-well plates for colony expansion and preservation. Four to 6 cloned lines were preserved for each line.

In preliminary studies several methods of preparing hybridomas were compared to determine the optimal conditions for use of monoclonal antibody technology in the study of *Anaplasma marginale*. The results obtained revealed that SP2/O-ag 14 and X63-Ag8.653 myeloma cells were the most useful fusion partners because of their growth characteristics, the efficiency of outgrowth of hybridomas, and their inability to secrete light or heavy chains. The fusion ratios found to be the most effective were 5 to 1 for SP2/O-Ag14 and 2.5 to 1 for X63-Ag8.653. Under the culture conditions employed, it was essential to have 2-ME in the culture medium and thymocytes as feeder cells. When these measures were disregarded, outgrowth of the hybridomas was unpredictable; however, when the measures described were taken, 600 to 1000 hybrids were obtained per fusion.

The use of erythrocyte-contaminated preparations of *Anaplasma marginale* as antigen presented no problems. Both the crude lysate and renografin-purified preparations were highly immunogenic. The majority of the hybrids detected in primary culture produced antibody to *Anaplasma marginale*. More anti-erythrocyte antibody producing hybrids were seen when the lysate was used as a source of antigen, however.

When a sufficient number of hybridomas were collected and preserved, they were tested by immunodiffusion to determine the class of antibody being produced. In addition, they were tested by indirect immunofluorescence on smears of infected erythrocytes to determine their patterns of binding to *Anaplasma marginale* or erythrocytes, on cultures of infected monocytes grown in short term culture and on acetone-fixed sections of tissue taken from infected cattle.

Selection of Cell Lines Producing Anti-Am105 Monoclonal Antibodies

The hybridoma cell supernatants are initially screened for anti-*Anaplasma marginale* antibody by indirect immunofluorescence on acetone-fixed smears of *Anaplasma marginale* infected blood. The positive (antibody producing) cell lines are then further screened for specific production of anti-Am105 antibodies using immunoprecipitation of either [$^{35}$S] methionine radiolabeled or [$^{125}$I] surface radiolabeled *Anaplasma marginale*. The exact procedure for this, which is a slight modification of the procedure reported by Palmer, G. H. et al, J. Immunology, 133:1010 (1984), is as follows.

The immunoprecipitation of surface-radioiodinated initial bodies and erythrocyte stroma was performed by using a modification of the technique described by Shapiro, S. Z. et al, J. Immunol. Methods, 13:153 (1976). The initial bodies or erythrocytes were disrupted with 1% (v/v) Nonidet P-40 and 0.1% (w/v) SDS at 4° C. for 30 min, centrifuged at 135,000×G for 60 min, passed through a 0.2 m filter (Millipore Corp., Bedford, Mass.), and sonicated for 15 sec at 50 W. Two hundred thousand trichloroacetic acid precipitable cpm were added to 50 1 hybridoma supernatant followed by 10 microliters rabbit anti-mouse immunoglobulin in siliconized tubes and were incubated at 4° C. for 30 min. One hundred microliters of 10% (v/v) protein A-bearing *Staphylococcus aureus* (Calbiochem-Behring Corp., La Jolla, Calif.) were added to each tube, incubated for 30 min at 4° C., and washed six times with Ten buffer (20 mM Tris-HCl, 5 mM EDTA, 0.1M NaCl, 15 mM NAN$_3$, pH 7.6) containing 0.1% Nonidet P-40, and for the first four washes 2M NaCl, by using centrifugation at 1250×G. The precipitated label was eluted by boiling the staphylococci-bound complexes for 3 min in 50 1 SDS-PAGE buffer and centrifuging at 1000×G.

The immunoprecipitates (2000 to 10,000 cpm) and the radioiodinated initial bodies and erythrocytes (200,000 cpm) were electrophoresed on 7.5 to 17.5% (w/v) gradient polyacrylamide gels. The gels were fixed in glass-distilled water-:methanol:acetic acid (6:4:1), were dried, and were exposed to Kodak X-Omat AR film (Eastman-Kodak, Rochester, N.Y.) at room temperature for 48 hr to identify the radioiodinated initial body and erythrocyte polypeptides, and at −70° C. by using Cronex Quanta III intensifying screens (DuPont, Wilmington, Del.) for 72 hr to identify the immunoprecipitates. $^{14}$C-Labeled proteins used for m.w. comparison (Amersham, Arlington Heights, Ill.) consisted of myosin, 200,000 m.w.; phosphorylase b, 92,500; bovine serum albumin, 69,000; ovalbumin, 46,000; carbonic anhydrase, 30,000; and lysozyme, 14,300. If the hybridoma supernatant contained monoclonal antibodies to Am105, a band on the X-ray film (autoradiograph) is observed at molecular weight of about 105,000.

Two cell lines (ANA 15D2 and ANA 22B1) were identified that produced anti-Am105 antibodies. The cell lines were double cloned and the supernatants concentrated to 0.1 mg immunoglobulin/ml following determination of isotype (both were IgG3). The concentrated supernatants were used for all further testing. The immunoprecipitation of $^{125}$I-Am105 was repeated with the double cloned hybridoma supernatants. The evidence that Am105 is an initial body protein and not of erythrocyte origin includes unreactivity of ANA 15D2, ANA 22B1, or rabbit anti-Am105 antibodies (all positive on initial bodies in infected erythrocytes) with uninfected erythrocytes or infected erythrocyte membranes using immunofluorescence, and failure of these antibodies to immunoprecipitate $^{125}$I radiolabeled erythrocyte ghosts. Additionally, ANA 15D2 AND ANA 22B1 immunoprecipitate Am105 metabolically radiolabeled in vitro during short term erythrocyte culture. It has been demonstrated that during short term cultures $^{35}$S incorporation occurs exclusively in initial bodies. Am105 is immunoprecipitated as a doublet band seen most clearly with $^{35}$S labelled Am105 or silver stained Am105. The doublet is consistently present and has been found to be indicative of a complex of two *Anaplasma marginale* proteins having surface-exposed epitopes. The two proteins as a complex are herein sometimes referred to as Major Surface Protein 1 (MSP-1) as well as the term Am105. The two proteins which make up the doublet are herein referred to as Am105U and Am105L. The protein Am105U is also sometimes referred to as MSP-1a with the Am105L sometimes referred to as MSP-1b. The proteins forming the complex have electrophoretic mobilities which are very nearly the same. Additional testing has indicated that Am105U has electrophoretic mobility corresponding to molecular weight of approximately 105 kilodaltons. Some measurements have indicated the electrophoretic mobility of Am105L is more nearly 100 kilodaltons. These mobilities are associated with the proteins of the MSP-1 or Am105 complex for the Florida geographical isolate of *Anaplasma marginale*. As further described below the corresponding proteins for other geographical isolates of *Anaplasma marginale* show a high degree of polymorphism in the proteins which make of the MSP-1 complex. Accordingly, the electrophoretic mobilities of the proteins forming this complex vary. However, the antigenic nature of these different isolates is similar as will be explained hereinafter.

Monoclonal antibodies can in general be prepared against other antigenic surface proteins of *Anaplasma marginale* using procedures the same as or similar to those described above. To date hybridoma cells producing monoclonal antibodies have been created against additional antigenic surface proteins of *Anaplasma marginale*.

TABLE 1

| Antigen | Monoclonal Antibody and Cell Type |
|---|---|
| Am105 (complex) | ANA 15D2(15D2), ANA 22B1(22B1) |
| Am105 (complex) | F34C1 |
| Am86 | AMG75C2 |
| Am36 | F19E1, ANAO-58A2 |

Testing for Neutralization of *Anaplasma marginale* by Monoclonal Antibodies

In order to test for initial body neutralization using the two anti-Am105 monoclonal antibodies, $10^{10}$ initial bodies were incubated with pooled ANA 15D2 and ANA 22B1 ascitic fluid, and the mixture was injected into splenectomized calves. Although complete neutralization was not observed, a significant prolongation of the prepatent period occurred (Table 2). The experiment was repeated with the assumption that the prolonged prepatent period observed with $10^{10}$ initial bodies indicated partial neutralization and that complete neutralization would likely occur at a lower infective dose. In the second experiment complete neutralization of initial body infectivity occurred using $10^7$ initial bodies and partial neutralization as judged by prolonged prepatent periods occurred using $10^8$, $10^9$, and $10^{10}$ initial bodies.

The mechanism of neutralization by the anti-Am105 monoclonal antibodies is unknown at present. Certainly monoclonal antibodies directed against an initial body determinant necessary for erythrocyte receptor binding would neutralize infectivity. ANA 15D2 and ANA 22B1 may recognize the same or overlapping determinants as they reciprocally inhibit binding of each other to $^{125}$I-Am105 in a competition radioimmunoassay. Other modes of neutralization include agglutination and when possible across murine-bovine species lines, interaction with bovine effector cells and complement-fixation with initial body lysis.

The effective use of Am105 as a protective immunogen to prevent bovine anaplasmosis would require that the determinants recognized by the neutralizing monoclonal antibodies be common to all isolates in a given region. Both similarities and differences in protein and antigenic composition among various isolates of *Anaplasma marginale* have been demonstrated. Six isolates from widely geographically separated areas of the U.S. (Florida; Okanogan, Washington; South Idaho; North Texas; Clarkston, Washington; Virginia) have been examined for the presence of determinants recognized by ANA 15D2 and ANA 22B1 using indirect immunofluorescence on acetone fixed blood smears. The determinants were present on 100% of the initial bodies (as determined by comparison with Wright's stained initial bodies in an adjacent section of the smear) in all six isolates. Additionally, the determinants were present at all stages of a primary, acute infection from 1% parasitemia through peak parasitemia with hemolytic crisis. The presence of thee determinants now identified as protective antigens on multiple isolates and their presence at all stages of infection fulfill important criteria for use of Am105 or its fragments as a vaccine. Am105 and Am105 polypeptides containing determinants recognized by the neutralizing monoclonal antibodies have been tested as effective immunoprophylaxis for bovine anaplasmosis.

Partial neutralization of infectivity of $10^{10}$ *Anaplasma marginale* initial bodies by monoclonal antibodies (ANA 15D2/22B1)

BALB/c×B10A (3r) mice were injected intraperitoneally (i.p.) with 1.0 ml Pristane and one week later with 2–3×10$^6$ double cloned hybridoma cells suspected of producing anti-Am105 antibodies. Ten days after injection with the hybridoma cells, ascitic fluid was withdrawn from the mice, centrifuged to pellet debris, and passed over a glass wool column. The indirect fluorescent antibody (IFA) titer is determined. A strong titer would be 1:16,000. $10^{10}$ initial bodies are purified from *Anaplasma marginale* (Florida isolate) infected erythrocytes as described in Palmer, G. H. et al, J. Immunology, 1331010 (1984) and resuspended in 2.5 ml RPMI 1640 (2 mM L-Glutamine, 25 mM HEPES). The initial bodies are added to 2.5 ml of ascitic fluid. The initial body-ascitic fluid suspension is briefly vortexed, incubated for 45 min. at room temperature, and injected into the left semitendinosus muscle of each cal. Daily blood samples are collected for 75 days post-inoculation (DPI) to determine packed cell volume (PCV) and parasitemia (1000 is erythrocytes counted). Probability values (p) are calculated using the pooled t-test; p values of less than 0.05 are considered significant. NS, not significant. ND, significance not determined. The results of a test using two cell lines designated ANA 15D2 and ANA 22B1 which produce monoclonal antibodies to Am105 and a cell line TRYP 1E1 which produced monoclonal antibodies against *Trypanosoma brucei* are reported in Table 2.

TABLE 2

| Parameter | ANA 15D2/22B1 | TRYP 1E1 | Significance |
|---|---|---|---|
| No. infected/challenged | 6/6 | 4/4 | |
| Mean DPI* to 1% parasitemia (range) | 31 (29–37) | 24 (23–25) | $p \leq 0.01$ |
| Mean peak parasitemia (%) (range) | 51 (30–58) | 71 (69–71) | $p \leq 0.01$ |
| Mean low PCV* (range) | 15 (13–17) | 11 (10–11) | NS |
| No. dead/challenged | 0/6 | 3/4 | ND |

*DPI means days post inoculation.
*PCV means packed cell volume.

These results indicate that by using $10^{10}$ initial bodies partial neutralization was observed as judged by a significant prolongation of the prepatent period.

Neutralization of infectivity of graded numbers of initial bodies by monoclonal antibodies (ANA 15D2/22B1)

The experiment was repeated with the hypothesis that the prolonged prepatent period observed with $10^{10}$ initial bodies indicated a partial neutralization and that complete neutralization would likely occur at a lower infective dose.

The protocol used was similar to that described in Part a. A constant amount of ascitic fluid was inoculated with either $10^{10}$, $10^9$, $10^8$, or $10^7$ purified *Anaplasma marginale* (Florida) isolate initial bodies, injected into calves, and infection monitored as previously described. The results are reported in Table 3.

TABLE 3

| Parameter | No. of Initial Bodies | ANA 15D2 22B1 | TRYP 1E1 | Significance |
|---|---|---|---|---|
| No. infected/ challenged | $10^{10}$ | 3/4 | 3/3 | ND |
| | $10^9$ | 4/4 | 3/3 | ND |
| | $10^8$ | 4/4 | 3/3 | ND |
| | $10^7$ | 0/4 | 3/3 | ND |
| Mean DPI to 1% parasitemia (range) | $10^{10}$ | 33 (32–33) | 26 (25–28) | $p \leqq 0.01$ |
| | $10^9$ | 35 (33–39) | 28 (27–29) | $p \leqq 0.01$ |
| | $10^8$ | 37 (36–38) | 30 (26–32) | $p \leqq 0.01$ |
| | $10^7$ | neg @ 75 | 34 (34–36) | ND |

These results indicate that complete neutralization of infectivity occurred using $10^7$ initial bodies and partial neutralization, as judged by prolonged prepatent periods, occurred using $10^8$, $10^9$ and $10^{10}$ initial bodies.

Purification of Monoclonal Antibodies

The steps for purifying the monoclonal antibodies to couple to the immunoadsorbent column are:

1. BALB/c×B10 A (3r mice were injected intraperitoneally with 1.0 ml Pristane (Aldrich Chemical Co., Milwaukee, Wis.) and one week later with 2–3×$10^6$ double cloned hybridoma cells. Ten days later, ascitic fluid with withdrawn from the mice, centrifuged at 1,675×G to pellet insoluble debris and passed over a glass wool column.
2. A 50% (V/v $NH_4SO_4$ precipitation is conducted on the wool column effluent and following resuspension in 0.032 M Tris is dialyzed for 24 hrs. against 0.032M Tris. This dialyzed sample is chromatographed on a DE-52 cellulose column and eluted using a 0–0.2 M NaCl continuous gradient in 0.032M Tris. The eluted fractions are titered using indirect immunofluorescence on acetone-fixed smears of *Anaplasma marginale* infected blood. The purity of the antibody is determined using sodium dodecyl sulfate-polyacrylamide gel electrophoresis (SDS-PAGE) with detection of protein using Coomassie Blue staining.

Preparation of the Monoclonal Immunoaffinity Chromatography Column

The purified monoclonal antibody, ANA 15D2 (pure by Coomassie Blue staining on SDS-PAGE) is dialized against 0.1M $NaHCO_3$, 0.5M NaCl pH 8.3. The dialized protein is coupled to CNBr-activated Sepharose 4B (Pharmacia Fine Chemicals, Piscataway, N.J.) at 10 mg protein/ml settled Sepharose 4B overnight at 4° C. by rotation. The coupled immunoaffinity matrix (ANA 15D2-Seph 4B) is poured into an Econo Column 11.5 ml column Bio-Rad Lab., Richmond, Calif.) and stored at 4° C. until use.

Source of the *Anaplasma marginale* Initial Bodies

*Anaplasma marginale* has never been successfully grown in long-term in vitro culture. The source of *Anaplasma marginale* therefore is blood of infected, splenectomized calves. The calves are inoculated with $10^{10}$ initial bodies intramuscularly and then checked daily for evidence of parasitemia using Wright's stained blood smears. When the percentage of infected erythrocytes reaches 40–95%, 4–7 liters of blood are collected into 4 units/ml heparin sulfate. The erythrocytes are washed 3× with phosphate buffered saline, pH 7.2 and then resuspended 1:1 in 31.2% dimethylsulfoxide in phosphate buffered saline. This suspension is frozen in liquid nitrogen and constitutes the *Anaplasma marginale* initial body source.

Disruption and Treatment of *Anaplasma marginale* Initial Bodies

The *Anaplasma marginale* infected erythrocytes ($10^{12}$ will yield approx. 1.0 mg pure Am105) are thawed from liquid nitrogen at 37° C. and washed 5× in phosphate buffered saline using centrifugation at 27,000×G. The sediment is resuspended in 35 ml phosphate buffered saline, disrupted by 2 min. of sonication at 50 watts (127×4 mm titanium probe, Braun-sonic 1510, Braun Instruments, San Francisco, Calif.) and then washed two times at 1650×G for 15 min. The purified initial bodies are disrupted in 5 ml 50 mM Tris-HCl (pH 8.0, 1.0% Nonidet P40, 0.1% sodium dodecyl sulfate, 5 mM EDTA, 5 mM iodoacetamide, 1 mM phenlmethylsulfonylfluoride, 0.1 mM tosyl-L-lysyl chloromethane) and applied to the ANA 15D-Sepharose 4B monoclonal immunoaffinity column.

Column Chromatography

The ANA 15D2-Sepharose 4B monoclonal immunoaffinity column is washed with 100×column volume with TEN buffer (20 mM Tris-HCl, 5 mM EDTA, 0.1M NaCl, 25 mM $NAN_3$, pH 7.6) 1% NP-40, 0.1% SDS and then approximately $10^{12}$ disrupted initial bodies are loaded onto the column at a rate of 25 ml/hr. The unbound proteins are washed out using 100×column volume TEN with 1.0% NP-40 and 0.1% SDS and then any remaining unbound proteins and the NP-40, SDS (nondialyzable detergents) are removed by 100×column volumes TEN without detergent. The specifically bound Am105 is eluted using 50 mM Tris pH 8.0 with 0.5% deoxycholate and 2M KSCN.

Recovery of Purified Surface Antigen

The eluted protein (Am105) is dialyzed against phosphate buffered saline to remove the KSCN and deoxycholate. Am105 is quantitated using a modified Lowry protein assay and frozen at −70° C. until use.

Preparation of Vaccine

Am105 is thawed and suspended in Freund's incomplete adjuvant to produce a vaccine in which purified antigen, such as Am105, is present in an amount of 10, 25 or 100 micrograms/milliliter.

Immunization Studies

Groups comprised of 5 Holstein calves, weighing approximately 100 kg, were immunized 4 times with 100 g of either ovalbumin emulsified in Freund's complete adjuvant (group 1), Am105 emulsified is in Freund's incomplete adjuvant (group 2), or Am36 emulsified in Freund's incomplete adjuvant (group 3). The immunizations were conducted on day 1, day 17, day 35 and day 59. Group 4, which consisted of 4 calves, was not immunized. The antibody response of the 4 groups to Am105 was determined using a radioimmunoassay based on $^{125}$I-Am105.

The calves were challenged on day 83 with $10^8$ purified Florida isolate A. marginale initial bodies. The calves were monitored for infection by daily clinical examination, determination of hematocrit, and examination of Wright's stained blood smears for presence of parasites. The results are presented in Table 4.

TABLE 4

|  | Group 1 | Group 2 | Group 3 | Group 4 |
|---|---|---|---|---|
| Titer to Am105 | $10^2$ | $10^4$ | $10^2$ | 0 |
| No. infected/No. challenged | 5/5 | 3/5 | 3/5 | 4/4 |
| x days to infection | 33 | 39(p\<.01)[a] | 38 | 29 |
| x peak parasitemia | 5.4 | <.01(p\<.01) | 1.5 | 4.2 |
| x low PCV[b] | 24.4 | 31(p\<.01) | 28 | 23 |

[a]Significance: p values were calculated by the pooled t-test. Probability values of less than 0.05 were considered significant.
[b]PCV = packed cell volume.

The significant elongation of the prepatent period (days until infection was detected), significant reduction in parasitemia, significant difference in PCV, and complete protection in 2 of 5 Am105 vaccinates relative to calves immunized ovalbumin indicates that Am105 is capable of inducing significant protection against challenge with *Anaplasma marginale*.

General Discussion

The major *Anaplasma marginale* initial body surface proteins and protein complexes identified to date (Am105 complex, Am105U, Am105L, Am86, Am61, Am36, Am31, Am15) each have a surface exposed epitope on the initial body. Evidence for the surface nature of Am105, Am86, Am61, Am36, Am31, and Am15 proteins was obtained by radioiodination of the proteins on intact initial bodies using a membrane impermeant radiolabeling technique (lactoperoxidase) (Palmer, G. H., McGuire T. C.: J. Immunol 133:1010–1015, 1984). *Anaplasma marginale* initial bodies were purified from parasitized erythrocytes by using ultrasonic disruption and differential centrifugation. The initial bodies were intact as determined by electron microscopy, were not agglutinated by anti-bovine erythrocyte sera and were infective. The initial body proteins surface radioiodinated using lactoperoxidase included Am220, Am105 complex, Am105U, Am105L, Am86, Am61, Am56, Am42, Am36, Am31 and Am25. Of these Am105, Am105U, Am105L, Am86, Am61, Am36 and Am31 are precipitated by neutralizing antibody. The latter group of proteins are major surface proteins and one or more of these proteins alone or in combination might be incorporated in a vaccine or diagnostic test. In fact, the data presented in Table 4 shows that either purified Am105 or Am36 will induce protective immunity against virulent *Anaplasma marginale* challenge in calves. That purified proteins will work as vaccines indicates that similar results might be achieved with synthetic peptides of 6 amino acids or more mimicking the antigenic structure of the biologically active epitopes, with antigens expressed in heterologous bacteria containing the genes coding for the biologically active epitopes of the surface proteins or with one or more antigens expressed in virus vectors containing the genes coding for biologically active epitopes of the surface proteins.

The major *Anaplasma marginale* initial body surface proteins (Am105, Am105U, Am105L, Am86, Am61, Am36 and Am31) bear epitopes recognized by neutralizing antibody. Antiserum prepared by immunization of rabbits with purified *Anaplasma marginale* initial bodies completely neutralized the infectivity of $10^{10}$ purified initial bodies for splenectomized cattle. Using the technique of immunoprecipitation these proteins were recognized by the neutralizing antibody, demonstrating their potential roles, either individually or in combination, in inducing neutralizing antibody and therefore their use as an improved vaccine for cattle. The recognition of these surface proteins was consistent regardless of the isolate (Florida, Washington-O, Virginia) of used to immunize the rabbits to prepare the antiserum.

It has been shown that Am105, Am105U, Am105L and Am36 each bear an epitope common among *Anaplasma marginale* isolates tested (Florida, Washington-O, Washington-C, Virginia N. Texas, S. Idaho, Kansas, Oklahoma, Kapiti (Kenya), and Israel-round and Israel-tails) and to *Anaplasma centrale* (a less virulent species) that are capable of inducing neutralizing antibody. The purification of Am105 or Am36 by monoclonal antibody immunoaffinity chromatography and the demonstration of its ability to induce protection in cattle immunized with the protein clearly shows their importance, either alone or in combination with other surface proteins, as an improved vaccine against anaplasmosis.

The Am105, Am105U, Am105L or Am36 epitopes are completely protease sensitive and do not bear any carbohydrate residues and as such can be easily mimicked by short (minimum 6 amino acids) synthetic peptides or by polypeptides expressed in a foreign bacterium or virus containing the gene coding for the epitopes. The availability of monoclonal antibody makes both the synthetic peptide and the gene cloning procedures alternative approaches to vaccine development as is explained more fully below.

The surface proteins Am105, Am105U, Am105L, Am86, Am61, Am36, Am31, Am13 identified to date are specifically recognized by serum taken from cattle over a period of 30 days to 255 days post-infection. This recognition is consistent regardless of the isolate used to infect the cattle (Florida, Virginia, N. Texas). This specific recognition is required for selection of *Anaplasma marginale* proteins to be used individually or in combination as the antigen in an improved serologic assay to diagnose anaplasmosis in cattle. These supporting data point to use of these proteins for diagnosing anaplasmosis. The isolation and incorporation of these proteins into a serologic assay for diagnosis is a straightforward technical procedure. The findings to date also indicate potential use of a synthetic peptide of 6 amino acids or more or a polypeptide expressed in a vector organism as immunologically equivalent agents for diagnostic purposes.

Am105 and Am36, isolated by monoclonal immunoaffinity chromatography and coated into wells of a microtiter plate at 5 to 100 ng/well, have been tested as the basis of an Enzyme Linked Immunosorbent Assay (ELISA) for serologic diagnosis of anaplasmosis. Each assay has been found capable of differentiating non-infected from *Anaplasma marginale* or *Anaplasma centrale* infected cattle at periods from 30–255 days post-infection and was accurate regardless of the isolate used to infect the cattle (Florida, N. Texas, Virginia, Washington-O, Washington-C, Idaho, Kenya, Israel-round, Israel-tailed). The present serologic assay is based on the isolated whole Am105 or Am36. These findings, however, imply the potential use of an immunologically similar synthetic peptide of six amino acids or more or a polypeptide expressed in a vector organism.

Proteins of 105,000 daltons (Am105), 86,000 daltons (Am86), 61,000 daltons (Am61), 31,000 daltons (Am31) and 15,000 daltons (Am15), all identified as surface proteins, are strongly antigenic as evidenced by antibody in *Anaplasma marginale*-infected cattle. In addition, dilutions of the post-infection sera have high titers to Am86 and Am15 throughout infection, indicating a preferential response. Use of Am86 alone or in combination with Am105, Am61, Am31, or Am15 as an antigen in a diagnostic test is implied from these findings. The present stage of this research also points to potential use of an immunologically similar synthetic peptide of six amino acids or more, or a polypeptide expressed in a vector organism which has epitopes recognized by post-infection sera as antigens in diagnostic tests for anaplasmosis.

PART II—SIZE POLYMORPHISMS IN DIFFERENT GEOGRAPHICAL ISOLATES OF *Anaplasma marginale*

Additional research has indicated that there are significant size polymorphisms in the two proteins forming the MSP-1 protein complex between different geographical isolates of *Anaplasma marginale*. Table 5 below shows the range of sizes for the corresponding component proteins Am105U and Am105L for the geographical isolates of *Anaplasma marginale* for Florida (F), southern Idaho (I), northern Texas (T), Virginia (V), and Clarkston, Washington (W). These molecular weight estimates were made by electrophoretic mobility analysis using polyacrylamide electrophoresis as explained by Oberle et al., Infection and Immunity, Vol. 56, No. 6 (1988) which is hereby incorporated hereinto by reference.

TABLE 5

| Major Complex Component | Apparent Molecular Mass (kDa) in Isolate[a] | | | | |
|---|---|---|---|---|---|
| | F | I | T | V | W |
| AmF105 | 105 | 98 | 97 | 100 | 100 |
| AmF100 | 100 | 95 | 89 | 70 | 86 |
| Recognized by 22B$_1$ | 105 | 95 | 89 | 70 | 86 |
| Recognized by R911 | 100 | 98 | 97 | 100 | 100 |

[a]Isolates: F, Florida; I, Southern Idaho; T, Northern Texas; V, Virginia; W, Clarkson, Washington.

PART III—RECOMBINANT Am105L

In this part we demonstrate that Am105 consists of a complex of two noncovalently linked polypeptides of similar molecular weight. To determine whether these two polypeptides, termed Am105U and Am105L, are products of separate genes, and to examine the structural and antigenic relationships between the polypeptides, we cloned and expressed genes coding for Am105L epitopes in *Escherichia coli*. In this report, we identify Am105U and Am105L as separate gene products, each bearing surface-exposed epitopes. Cloning and expression of Am105L will allow determination of its efficacy as a single, non-complexed immunogen.

Preparation of Antisera

Mouse monoclonal antibodies were prepared as described before (14, 17) and designated as follows: $1E_1$ and $24A_1$, control antibodies to a surface glycoprotein of Trypanosoma brucei; $F19E_1$ an antibody that immunoprecipitates Am36 (19); $15D_2$ and $22B_1$, antibodies that immunoprecipitate Am105 and neutralize infectivity of *Anaplasma marginale* in vitro (17); and $F34C_1$, an antibody that immunoprecipitates Am105.

Antisera to Am105 (17), to isolated *Anaplasma marginale* initial bodies (19), and to *E. coli* containing pBR322 or pAM25 plasmid DNA were made in rabbits. Rabbits were immunized four times with lysed bacteria ($2 \times 10^9$ organisms in complete Freund adjuvant for the first immunization, and $10^{10}$ organisms in incomplete adjuvant for the other three). Titers were evaluated by an enzyme-linked immunosorbent assay (ELISA), radioimmunoassay (3), or immunoprecipitation of [$^{35}$S]methionine-labeled extracts of *Anaplasma marginale* (2). These rabbit antisera are designated as follows: R612, a control antibody prepared against a surface glycoprotein of T. brucei; R781, an antibody prepared against isolated initial bodies of *Anaplasma marginale*; R873 and R874, antibodies prepared against Am105 isolated by immunoaffinity chromatography on monoclonal antibody-Sepharose 4B (17) purified Am105 consists of Am105U and Am105L); R907, an antibody prepared against *E. coli*(pBR322); and R911, an antibody prepared against *E. coli*(pAM25).

Antigen detection on nitrocellulose filters—Proteins of *Anaplasma marginale* or recombinant *E. coli* were bound to nitrocellulose filters and detected by reaction with specific antisera and $^{125}$I-labeled protein A as described by Young and Davis (26), with two modifications: (i) after chloroform lysis, filters were fixed in 10% acetic acid-25% isopropanol; and (ii) 1% hemoglobin was added to buffers instead of bovine serum albumin to block nonspecific binding of $^{125}$I-labeled protein A to the filters.

ELISA—ELISAs were as described by Ellens and Gielkens (6), using Am105 attached to plates at 50 ng per well. The enzyme label was horseradish peroxidase-protein A, and the substrate was recrystallized 5-aminosalicylic acid. Am105 was isolated from *Anaplasma marginale* by immunoaffinity chromatography on monoclonal antibody $15D_2$-Sepharose 4B (17) and consisted of Am105U and Am105L. Sera against Am105 and against *E. coli* containing pBR322 or pAM25 were prepared in rabbits.

Immunoprecipitation

*Anaplasma marginale* organisms were radiolabeled by metabolic incorporation of [$^{35}$S]methionine during short-term in vitro culture (2) or by surface radioiodination, using lactoperoxidase (19). *E. coli* organisms were also labeled with $^{35}$S during exponential growth in 1-ml cultures containing 250 Ci of [$^{35}$S]methionine and 35 g of ampicillin per ml. After removal of the unincorporated radiolabel, organisms were solubilized by sonication at 4° C. in a lysis buffer consisting of 50 mM Tris hydrochloride (pH 8.0), 5 mM EDTA, 5 mM iodoacetamide, 1 mM phenylmethylsulfonyl fluoride, 0.1 mM N-tosyl-L-lysine chloromethyl ketone, 0.1% (wt/vol) sodium dodecyl sulfate (SDS), and 1% (vol/vol) Nonidet P-40. The solubilized extract was centrifuges at 130,000×g for 1 h at 4° C. and passed through a 0.2-m-pore-size filter (Centrex; Schleicher & Schuell, Inc.) before being used for immunoprecipitation with rabbit or mouse antibodies and protein A-bearing *Staphylococcus aureus* (Calbiochem)(9, 17, 23). The precipitated radiolabel was eluted and analyzed on 7.5 to 17.5% polyacrylamide-SDS gels, 7.5% polyacrylamide gels containing 4M urea, or 5% polyacrylamide gels containing 4M. $^{14}$C-labeled standard proteins were as follows (molecular weight): myosin (200,000), phosphorylase b (92,500), bovine serum albumin (69,000), ovalbumin (46,000), carbonic anhydrase (30,000), and lysozyme (14,300).

For the experiment described below (see FIG. 5) immunoprecipitated recombinant Am105, Am105U, and Am105L protein bands were cut out from dried 7.5% polyacrylamide-4M urea gels and then separately rehydrated and electroeluted into a mixture of 50 mM Tris hydrochloride pH 8.0) 0.1% (wt/vol) SDS, and 1% (vol/vol) Nonidet P-40. Polyacrylamide was removed by centrifugation, and the $^{35}$S-labeled proteins were immunoprecipitated again from electroelution buffer.

Peptide Mapping

Immunoprecipitated, $^{35}$S-labeled proteins were cut out from dried polyacrylamide gels and compared for sequence homology by peptide mapping as described before (5). Radiolabeled peptides produced by limited proteolysis with *S. aureus* V8 protease were separated on 15% polyacrylamide-SDS gels and detected by fluorography (4).

Isolation of *Anaplasma marginale* DNA

Bovine blood, infected with *Anaplasma marginale* at >50% erythrocytic parasitemia, was washed four times with phosphate-buffered saline. At each wash an upper layer containing leukocytes and erythrocytes was removed. The remaining erythrocytes were then frozen in phosphate-buffered saline at a packed cell volume of 50%. A 100-ml volume of the erythrocyte suspension was thawed and centrifuged at 30,000×g for 20 min at 4° C. to pellet *Anaplasma marginale* initial bodies and erythrocyte membranes. The pellet was washed a further three times in phosphate-buffered saline at 30,000×g to remove hemoglobin from the lysed erythrocytes. DNA was then extracted from initial bodies (11) and further purified by deproteinization with phenolchloroform, digestion with RNase A and proteinase K, and precipitation with ethanol.

Preparation of Recombinant DNA Libraries

*Anaplasma marginale* DNA was partially digested with Sau3A to an average size of 5 kilobases (kb). Digested DNA was ligated with BamHi-cleaved and dephosphorylated pBR322, using T4 DNA ligase (25). *E. coli* HB101 cells were transformed to ampicillin resistance by the high-efficiency transformation protocol and Hanahan (8). Plasmids pAM22 and pAM25 were identified by expression screening of a library containing 8,000 recombinants with R873 serum (rabbit anti-[Am105U plus Am105L] complex). Other colonies in this library, such as that containing pAM14, also reacted with R873 and contained the pAM22 sequence plus various lengths of additional DNA that extended beyond the BglII sites.

A second library of 3,000 recombinants was prepared by digesting *Anaplasma marginale* DNA to completion with BglII and ligating into the BamHI site of pBR322. Clones containing pAM97 and pAM113 were identified in this library by expression screening with R873.

Southern blotting—The protocol used was a modification of that described by Wahl et al. (24). Portions (0.5 g) of *Anaplasma marginale* genomic DNA or plasmid DNA (0.36 g) were digested with the appropriate restriction enzymes. For comparison of plasmid and genomic sequences on the same gel, 0.5 g of digested genomic DNA or 1.8 ng of plasmid DNA was subjected to agarose gel electrophoresis and blotted onto nitrocellulose filters. Hybridization was at 65° C. in 5× SSPE (0.18M NaCl, 0.01M NaH$_2$PO$_4$, 0.001M EDTA [pH 7.4])-0.25% Sarkosyl (Sigma) containing 10% dextran sulfate, 100 g of denatured calf thymus DNA per ml, and a $^{32}$P-labeled nick-translated probe. Filters were washed a total of five times, finally in 0.1× SSPE-0.0033% Sarkosyl at 65° C. The probe was the 1.4-kb SstI fragment of pAM97, isolated from agarose gels.

Genomic libraries and AM105 expression by *E. coli*—Initial experiments investigated the specificity and sensitivity of immunoblot assays in detecting *Anaplasma marginale* proteins immobilized on nitrocellulose filters (26). In previous studies we prepared monoclonal and polyvalent antisera against *Anaplasma marginale* which has specificity for different surface proteins (17–19). The reactions of these antisera with positive and negative control antigens are shown in FIG. 1A. All antibodies detected *Anaplasma marginale* erythrocytes and did not react with noninfected erythrocytes. The sensitivity of detection was greatest with R873, a rabbit antiserum against immunoaffinity-isolated Am105. R873 detected as few as 1,200 parasitized erythrocytes in the 1 microliter spot applied to the filter. The specificity of each antibody in immunoblots was the same as that observed previously in immunoprecipitation experiments. Polyvalent or monoclonal antibodies against Am105 or another surface protein, Am36, reacted with the appropriate protein; there were not cross-reactions or reactions with the negative control, ovalbumin. R873 detected a minimum of 1 ng of purified AM105. R781 was an antiserum prepared against isolated *Anaplasma marginale* initial bodies; it immunoprecipitated both Am105 (Am105U and Am105L) and Am36 (data not shown), and recognized Am105 and Am36 in immunoblots (FIG. 1A). We considered this assay sufficiently sensitive and specific to detect expression of *Anaplasma marginale* proteins in recombinant *E. coli*.

Previous data have suggested that gene regulatory sequences of rickettsiae may function in *E. coli* (10, 13, 25). Accordingly, parasite DNA was extracted from bovine erythrocytes containing a Florida isolate of *Anaplasma marginale*. The DNA was partially digested with Sau3A, inserted into the BamHI site of phosphatase-treated pBR322, and used to transform *E. coli* HB101 to ampicillin resistance. This genomic library was screened with R873 in the immunoblot assay for expression of Am105 antigenic determinants.

Figure 1B:
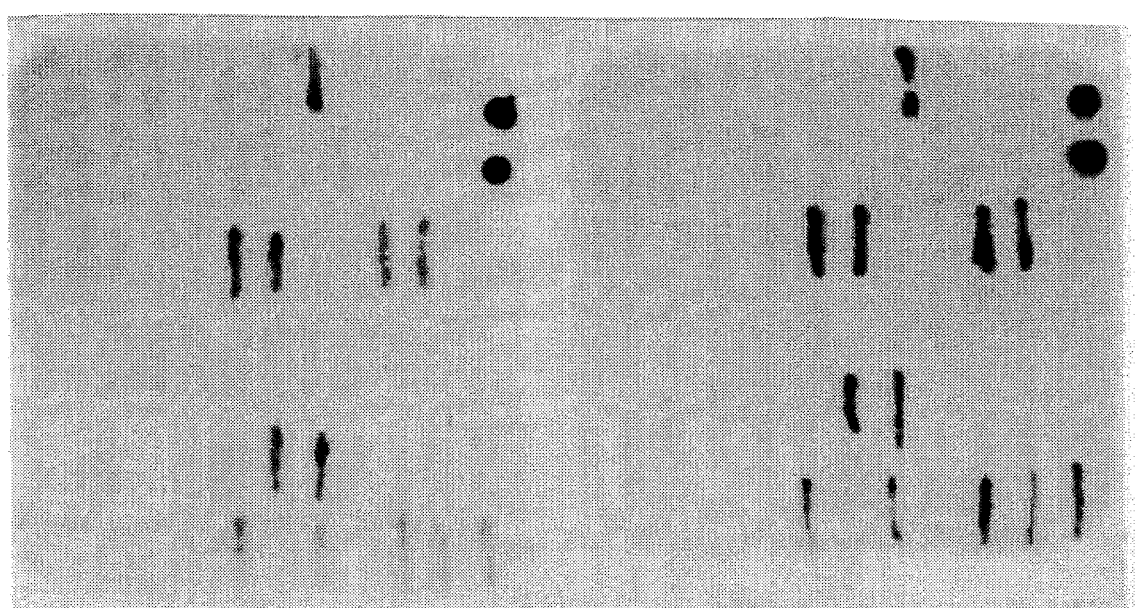
FIG. 1B is a reproduction of a radiograph showing the detection of proteins from recombinant-plasmid-containing *E. coli* on nitrocellulose. The proteins where screened for reaction with rabbit antiserum R873, which is reactive to the native *Anaplasma marginale* surface protein complex alternatively referred to as MSP-1 or Am105.
Figure 2:
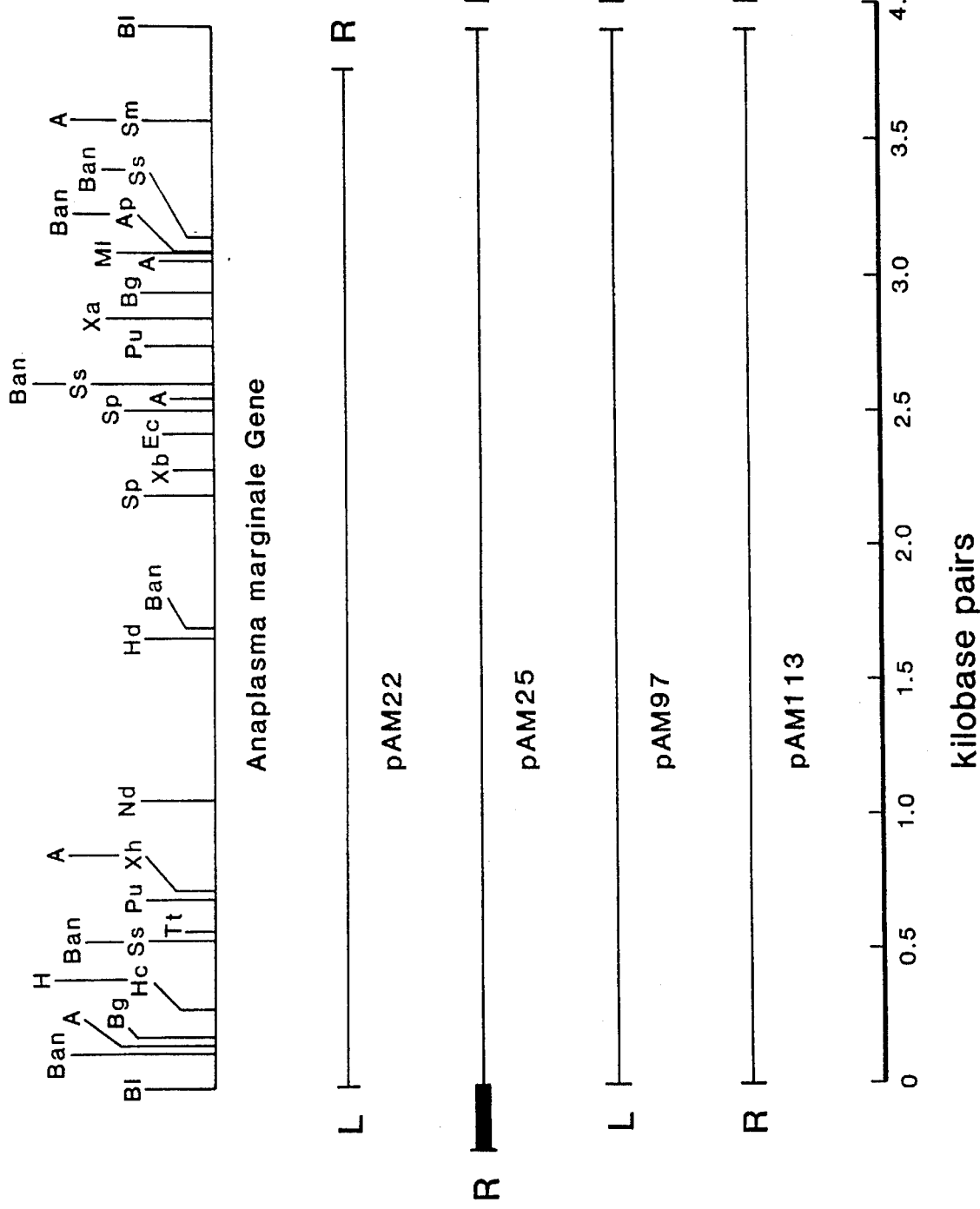
FIG. 2 is a restriction enzyme map showing relevant portions of the *Anaplasma marginale* gene coding for the expression of the protein recombinant Am105. The relative orientation and relationship of the gene as incorporated into the recombinant plasmids pAM22, pAM25, pAM97, and pAM113 are also shown.

*E. coli* colonies containing recombinant plasmids of various sizes reacted stably with the antiserum (FIG. 1B). The restriction enzyme maps of insert DNAs from pAM22 and pAM25, the smallest plasmids of expressing colonies (3.75 and 4.15 kb, respectively), are shown in FIG. 2. All plasmids from expressing bacteria contained the inserted sequence present in pAM22; there were various lengths of additional insert DNA in the larger plasmids which expended beyond the BglII sites. Restriction enzyme mapping and Southern blotting suggested that the shaded sequence of 240 base pairs in pAM25 was not contiguous with the remainder of pAM25 DNA in the *Anaplasma marginale* genome and that two Sau3A fragments were ligated in this plasmid during cloning. Both possible insert orientations with respect pBR322 DNA were found in plasmids from expressing colonies (FIG. 2).

Analysis of each expressed plasmid DNA, and of genomic DNA by Southern blotting, suggested that the inserted sequence in pAM22 should be contained within a single BglII fragment of *Anaplasma marginale* genomic DNA. To confirm this, we prepared a second library. *Anaplasma marginale* DNA was digested to completion with BglII and inserted into the BamHI site of pBR322. Plasmids pAM97 and pAM113 were identified in this library by expression screening with R873; they contained the expected BglII fragment in both orientations (FIG. 2).

Proteins Expressed by Recombinant *E. coli*

Figure 3:
FIG. 3 is a reproduction of a radiograph showing electrophoretically separated *Anaplasma marginale* proteins, proteins from recombinant *E. coli* having plasmid pAM25, proteins from *E. coli* with plasmid pBR322, and molecular weight standard proteins.

To characterize novel proteins synthesized by recombinant *E. coli*, bacteria containing either pAM25 or pBR322 were radiolabeled by metabolic incorporation of [$^{35}$S]methionine. The radiolabeled proteins were analyzed by immunoprecipitation and SDS gel electrophoresis. The protein profile of recombinant *E. coli* is shown in FIG. 3, lane 7, and may be compared with the analogous profile of control bacteria containing only pBR322 (lane 8). All protein bands were present in both lanes, except for a major radiolabeled polypeptide of 105,000 molecular weight in recombinant bacteria. When labeled proteins were immunoprecipitated by R873, one normal *E. coli* protein was recognized. However, in recombinant bacteria, the additional 105,000-molecular-weight protein was also precipitated (compare lanes 5 and 10). A similar result was obtained with a different antiserum to Am105, R874 lanes 3 and 12). These results demonstrated that a novel protein, coded for by pAM25 DNA, was expressed as a major component of the recombinant bacteria. This protein had a similar molecular weight and shared antigenic determinants with immunoaffinity-isolated Am105 from *Anaplasma marginale*.

R873 and R874 reacted with one or two normal *E. coli* proteins when used undiluted in immunoprecipitation, presumably because of prior exposure of rabbits to the bacterium. The possibility of a cross-reaction between AM105 and *E. coli* proteins is considered less likely, because antisera to lysed nonrecombinant *E. coli* did not recognize Am105 (see FIGS. 5 and 6). The reaction of R873 with *E. coli* was not observed in immunoblot assays because the dilution of antiserum used 1:4,000) effectively removed anti-*E. coli* activity while retaining activity against Am105.

The molecular weight of the recombinant protein was identical in bacteria containing pAM25, pAM22, pAM97, or pAM113 plasmids. The level of expression in each of these recombinants was comparable, as judged by relative band intensity on SDS gels. The orientation of insert DNA with respect to pBR322 had no apparent effect on expression (both orientations were equally represented in the four plasmids. These data suggest the following: (i) that the *Anaplasma marginale* gene is functional in *E. coli*; (ii) that the gene is contained within the cloned BglII fragment; and (iii) that the expressed molecule is not a fusion protein composed of both pBR322- and *Anaplasma marginale*-encoded amino acids.

Recombinant Am105 is structurally homologous to nonrecombinant Am105L. Recombinant Am105 was recognized by R873 and hence was antigenically homologous with Am105U and/or Am105L polypeptides. However, recombinant Am105, expressed by any of the recombinants, was not recognized by monoclonal antibodies $22B_1$ or $15D_2$ in immunoprecipitation or immunoblot assays (data not shown), or by R781 (FIG. 3, lanes 2 and 13). There were, therefore, important antigenic differences between recombinant and native Am105. We compared recombinant Am105 for structural homology with each component of the Am105 doublet, Am105L and Am105U. *Anaplasma marginale* was radiolabeled with [$^{35}$S]methionine, solubilized, and immunoprecipitated with the neutralizing monoclonal antibody $22B_1$, and the precipitated proteins were separated by electrophoresis in a 7.5% polyacrylamide-SDS gel containing 4M urea (FIG. 4A, lane 3). The Am105 doublet was clearly resolved. No bands were visible in the control lane (*Anaplasma marginale* plus $24A_1$ monoclonal antibody, lane 4). Recombinant Am105, immunoprecipitated by R873, was analyzed on the same gel. The recombinant Am105 migrated as a single band in an identical position to Am105L (FIG. 4A, lane 1).

The Am105 doublet in this gel system was resolved sufficiently to allow cutting out of the Am105L and Am105U components of the immunoprecipitate from a dried gel. Gel fragments containing each polypeptide were then rehydrated and analyzed by peptide mapping (5). Recombinant Am105, immunoprecipitated by R873, was also cut out and analyzed.

Figure 4B:
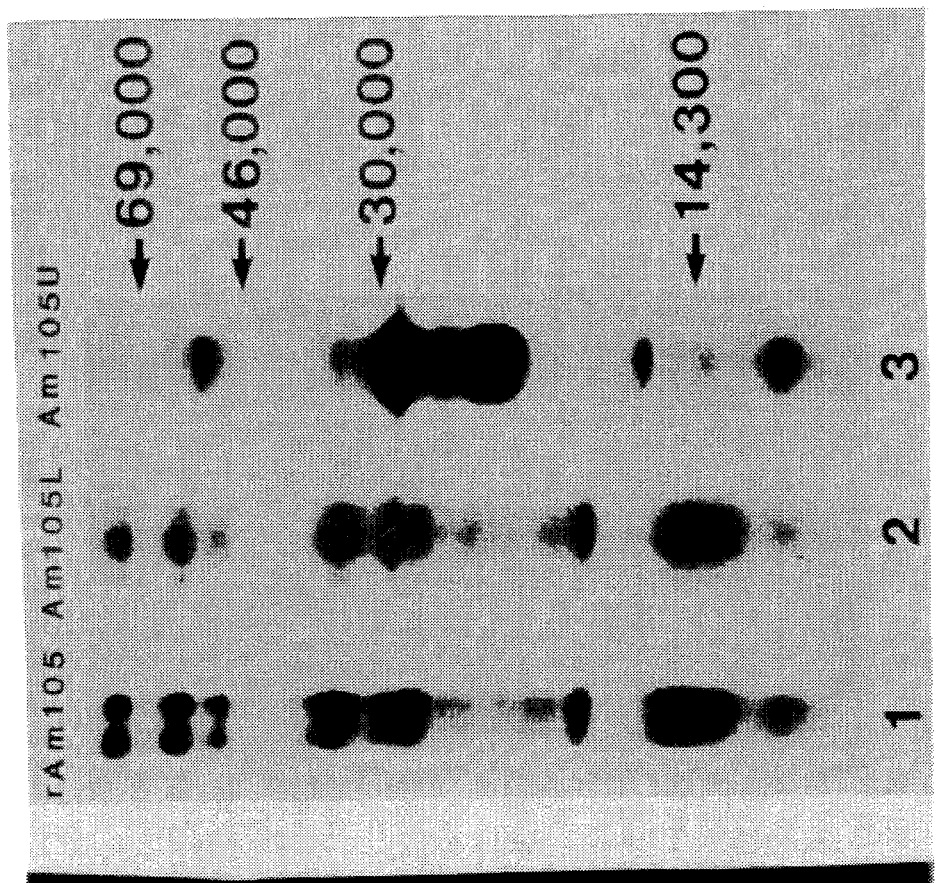
FIG. 4B is a reproduction of a radiograph showing electrophoretically separated polypeptide fragments resulting from treatment of recombinant Am105, and purified native proteins Am105L and Am105U after treatment with a protease.
Figure 4A:
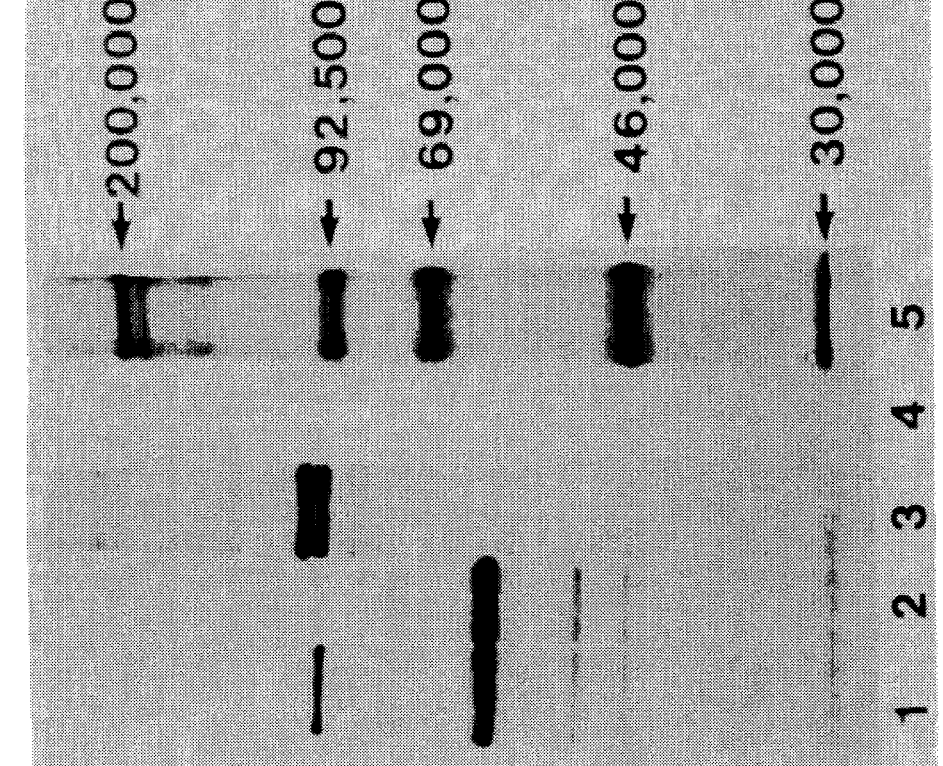
FIG. 4A is a reproduction of a radiograph showing electrophoretically separated proteins including recombinant Am105, native Am105 (including Am105L and Am105U), E. coli cells containing recombinant plasmid pAM25, and E. coli cells containing plasmid pBR322.

FIG. 4B shows a peptide map obtained by partial digestion of the eluted polypeptides with S. aureus V8 protease. Cleavage peptides of recombinant Am105 closely resembled those of Am105L. Initial proteolysis products of both recombinant Am105 and AM105L were polypeptides of 75,000, 59,000, and 51,500 molecular weight. Identical low-molecular-weight components (34,300, 18,600, and 13,000 to 16,000) were also generated. Therefore, the recombinant Am105 and AM105L molecules were homologous and possibly identical.

In contrast, cleavage peptides produced from Am105U were largely dissimilar to both Am105L and recombinant Am105. Predominant digestion products of Am105U in the 22,000- to 27,000-molecular-weight range had no counterpart in Am105L or recombinant Am105. Another peptide of 16,000 molecular weight was also absent from Am105L and recombinant Am105. Although different peptides were generated from Am105L and AM105U by proteolysis, the sensitivity of this procedure did not permit a determination of total nonhomology between Am105L and Am105U. For example, cleavage peptides of 29,500 were produced from both Am105L and Am105U. Whether these two low-molecular-weight peptides share homology will require further structural analysis.

Antigenic relationships among recombinant Am105, Am105L, and Am105U polypeptides. The antigenic relationships among Am105L, Am105U, and recombinant Am105 were investigated by preparing antisera against bacteria expressing recombinant Am105 in four rabbits; another four rabbits were immunized with *E. coli* containing pBR322 as a control. Sera were tested for recognition of nonrecombinant Am105 by an ELISA. All rabbits immunized with recombinant bacteria developed antibodies to Am105, ranging in titer from 1:100 to 1:1,000. No rabbits immunized with control *E. coli* developed antibodies to Am105. The anti-recombinant-Am105 sera immunoprecipitated both Am105L and Am105U from [$^{35}$S]methionine-labeled *Anaplasma marginale* (data not shown), and therefore reacted similarly to R873 and 22B$_1$ antibodies.

Figure 5:
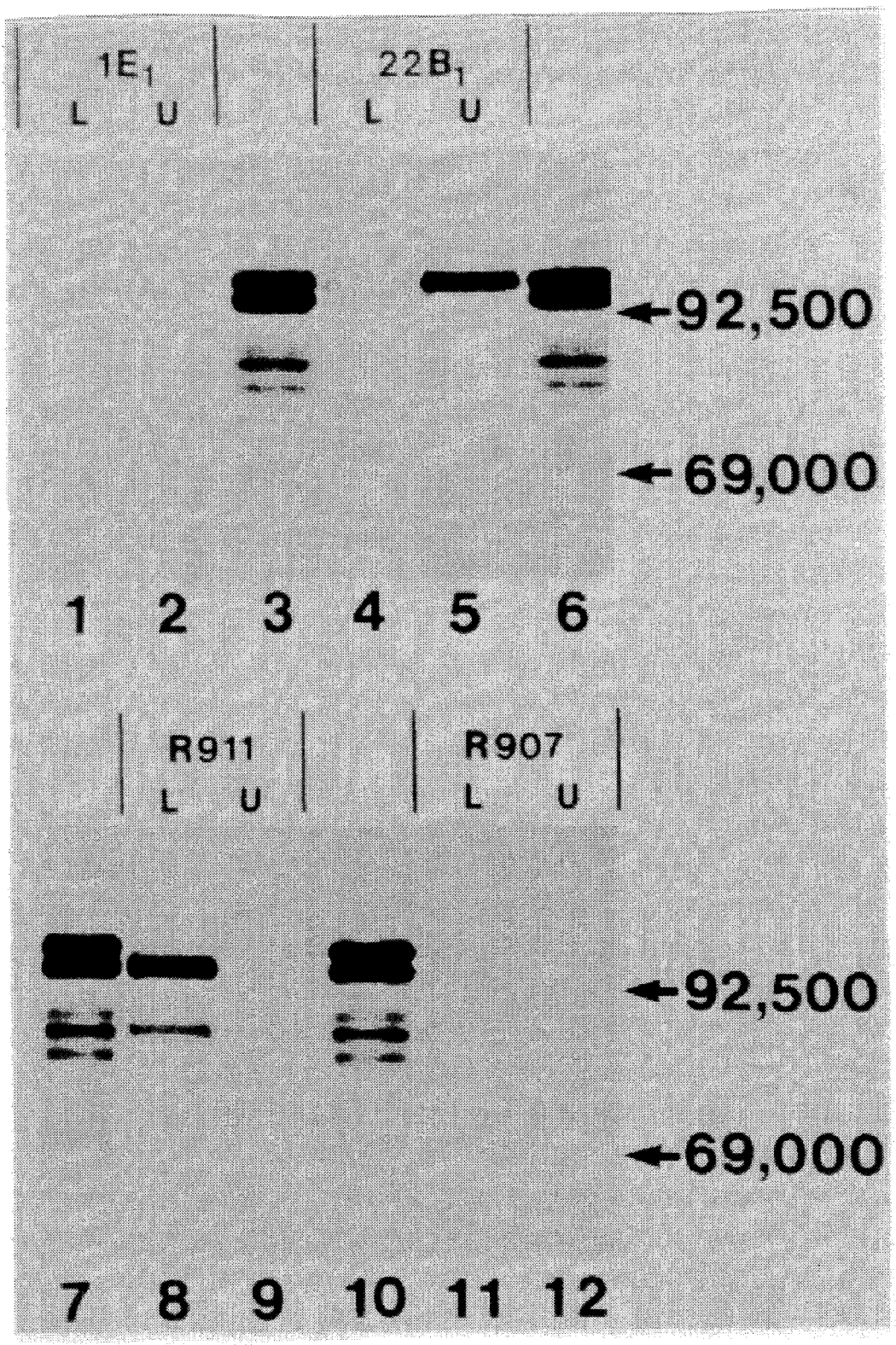
FIG. 5 is a reproduction of a radiograph showing electrophoretically separated proteins including recombinant Am105, native Am105L, and native Am105U after immunoprecipitation with monoclonal antibodies $1E_1$ and $22B_1$, and rabbit antisera R911 and R907.

There are two possible explanations for these results. First, Am105L and Am105U may share antigenic determinants and therefore be immunoprecipitated together. Second, Am105L and Am105U may be antigenically unrelated but complexed. To discriminate between these possibilities, Am105L and Am105U were separately purified and immunoprecipitated. A detergent extract of [$^{35}$S]methionine-labeled *Anaplasma marginale* was first immunoprecipitated with monoclonal antibody 22B$_1$, and the Am105L and Am105U components of the precipitate were separated by SDS gel electrophoresis. The Am105L and Am105U bands were cut out, electroeluted, and then separately immunoprecipitated again with monoclonal antibody 22B$_1$ or with rabbit anti-recombinant-Am105 serum (FIG. 5). Only Am105U was reimmunoprecipitated by 22B$_1$; Am105L was not recognized (lanes 4 and 5). In contrast, anti-recombinant-Am105 serum immunoprecipitated Am105L but not Am105U (lanes 8 and 9) when the two components were separated before immunoprecipitation. Therefore, recombinant Am105 was antigenically homologous only to Am105L.

Thus, Am105 exists as a complex of two polypeptides, Am105L and Am105U. Monoclonal antibody 22B$_1$ recognizes an epitope present on Am105U, and binding to that epitope causes precipitation of both components of the complex. The complex is stable in 1% Nonidet P-40 and 0.1% SDS, which are present in the immunoprecipitation reaction, but is dissociated by boiling in SDS gel sample buffer. Am105L and Am105U are apparently not linked by disulfide bonds, because the molecular weight is unchanged when electrophoresis is performed under reducing or non-reducing conditions. Recombinant Am105 is structurally and antigenically homologous to Am105L. No evidence was obtained for structural or antigenic homology between recombinant Am105 and Am105U polypeptides or between Am105L and Am105U. These data explain the positive reaction of recombinant Am105 with rabbit anti-Am105 sera and a negative reaction with monoclonal antibody 22B$_1$.

Figure 6:
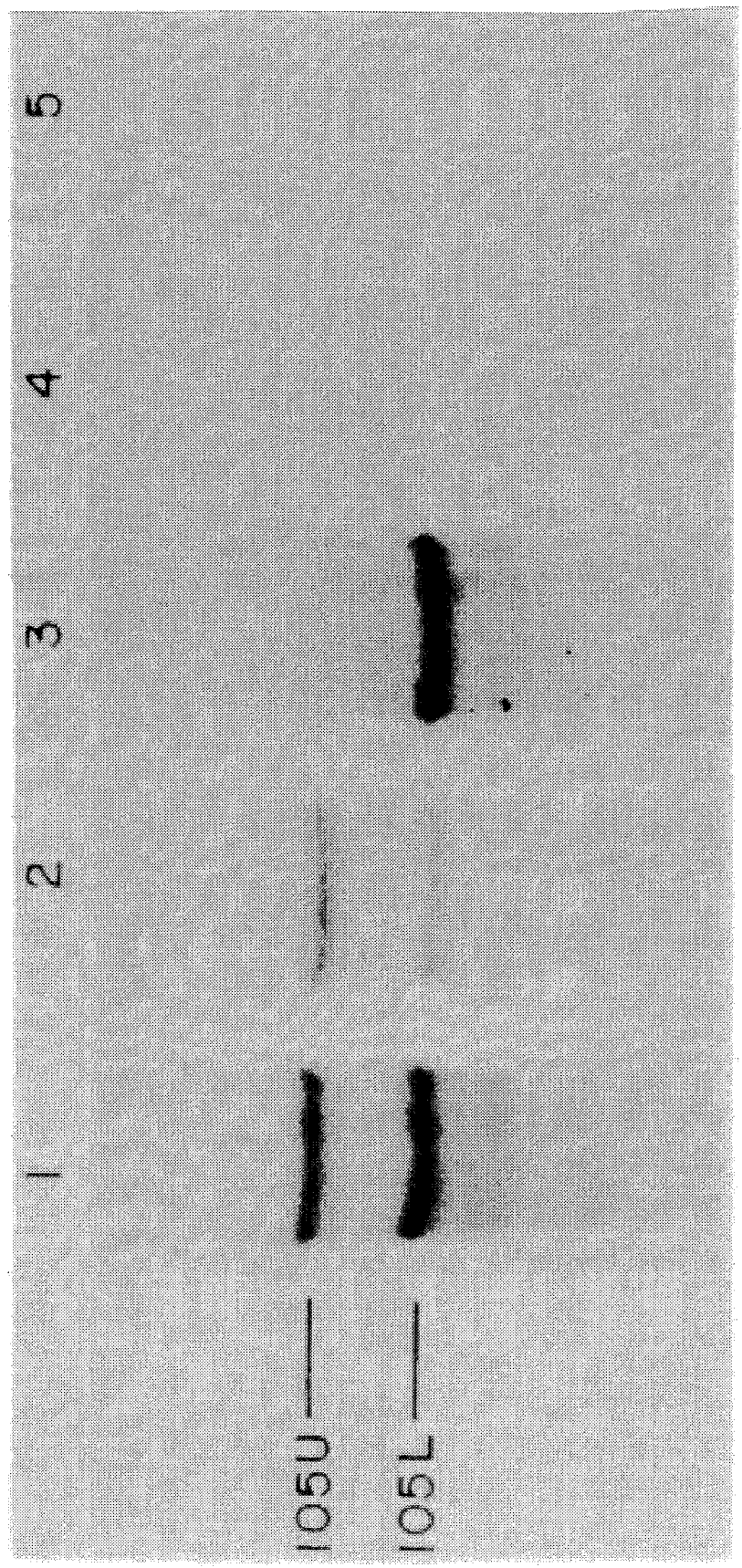
FIG. 6 is a reproduction of a radiograph showing electrophoretically separated proteins resulting from the surface radiolabeling and immunoprecipitation of *Anaplasma marginale* initial bodies using monoclonal antibodies $1E_1$ and $22B_1$, and rabbit antisera R911 and R907.

Surface radiolabeling of *Anaplasma marginale* initial bodies labels both Am105L and Am105U. Viable initial bodies were radiolabeled with $^{125}$I, using lactoperoxidase as described before (19). Labeled extracts were then immunoprecipitated with R911 (anti-recombinant Am105), R873 (anti-Am105), monoclonal antibody 22B$_1$, or the appropriate control antibody. The precipitates were analyzed on polyacrylamide gels containing 4M urea (FIG. 6). The results showed that both Am105L and Am105U polypeptides contained the radiolabel and were precipitated by R911, R873, and 22B$_1$. The increased band intensity of Am105U when precipitated by 22B$_1$ and of Am105L when precipitated by R911 suggests some dissociation of the Am105L-AM105U complex during this immunoprecipitation.

Figure 7A:
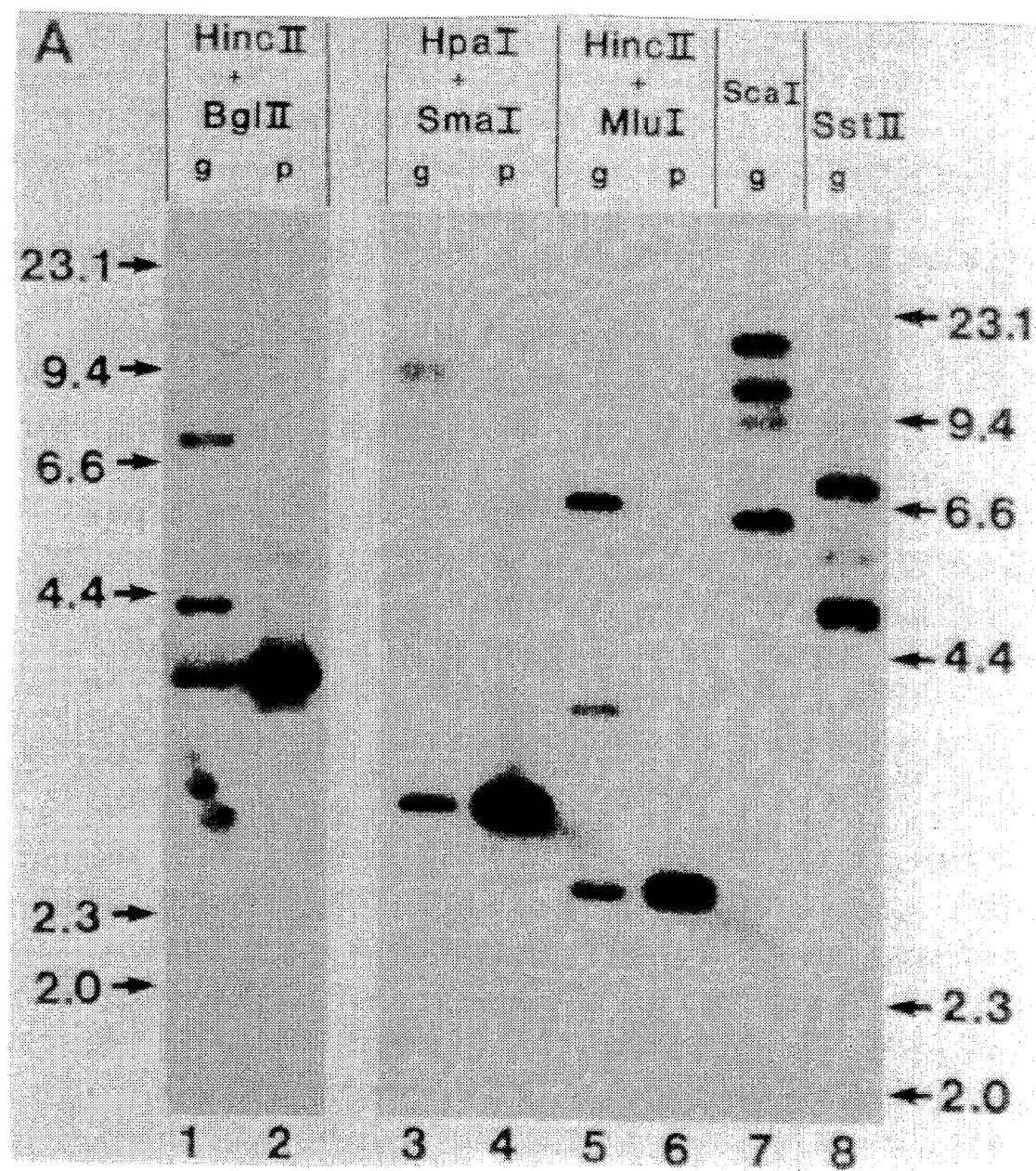
FIG. 7A is a reproduction of a radiograph showing electrophoretically separated DNA comparing *Anaplasma marginale* genomic DNA versus recombinant plasmid DNA using Southern blotting.
Figure 7B:
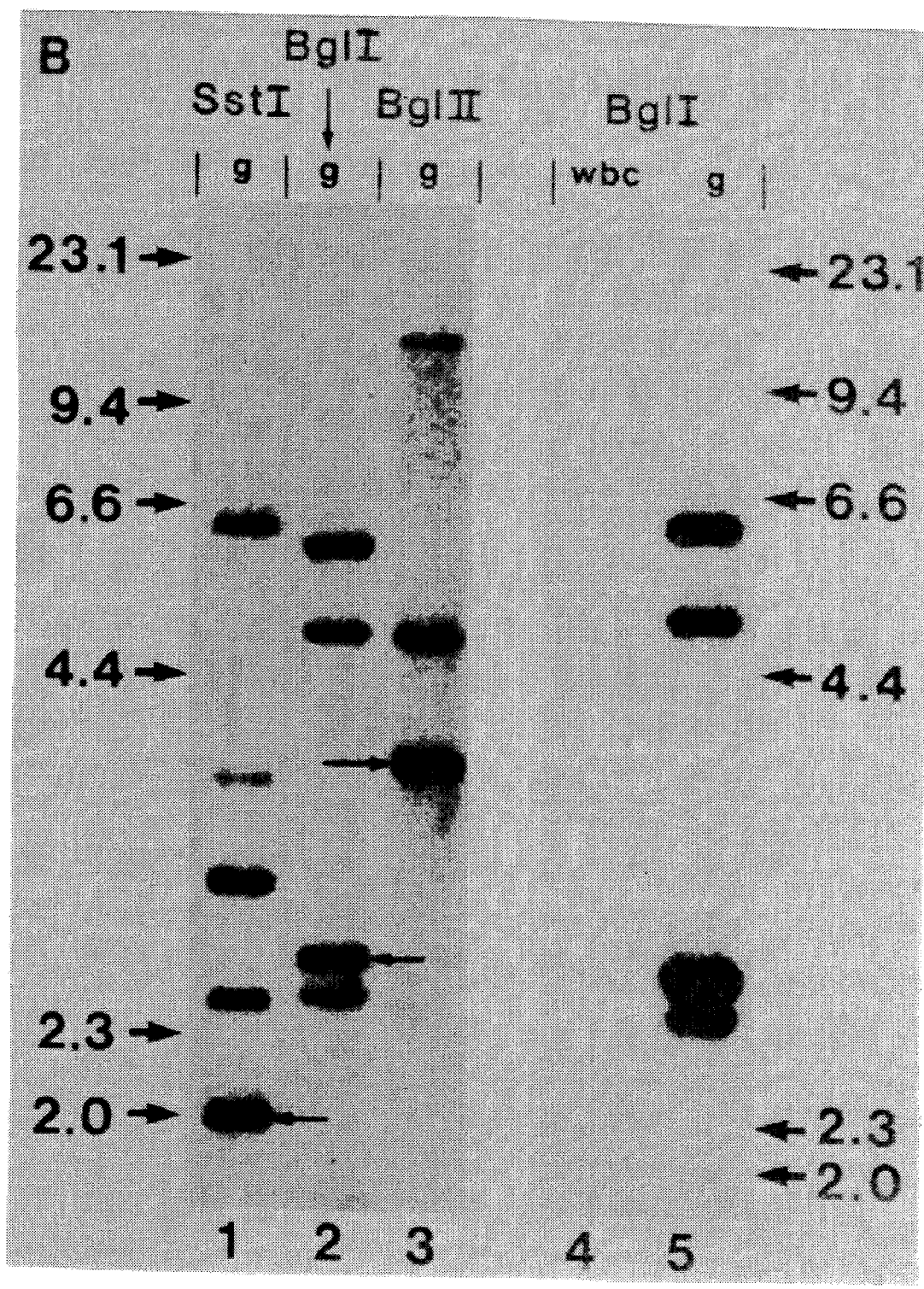
FIG. 7B is a reproduction of a radiograph showing electrophoretically separated DNA comparing *Anaplasma marginale* genomic DNA versus bovine leukocyte DNA after treatment by restriction enzymes.

*Anaplasma marginale* genome contains multiple copies of the cloned BglII fragment. *Anaplasma marginale* genomic DNA was cut with restriction enzymes; the DNA fragments were separated by gel electrophoresis, blotted to nitrocellulose, and probed with $^{32}$P-labeled plasmid insert DNA from bacteria expressing recombinant Am105. By using enzymes which did not cut within the probe sequence, we observed multiple hybridizing bands (FIG. 7A, lanes 7 and 8). To discover whether these represented partially homologous copies of the cloned sequence or polymorphism in flanking regions, we cleaved genomic DNA with restriction enzymes that would generate a predictable fragment. HincII plus MluI digestion should yield a 2.8-kb fragment hybridizing to the HincII-HindIII probe. For comparison, plasmid DNA containing the entire 3.9-kb BglII fragment was also digested with HincII plus MluI and analyzed in the adjacent gel lane (FIG. 7A, lanes 5 and 6). The expected 2.8-kb fragment was found in both digests, but hybridizing bands of 4.0 and 67.7 kb were also observed in the genomic DNA. The 4.0- and 6.7-kb bands must represent partially homologous copies of the 3.9-kb cloned BglII fragment that do not have the HincII or MluI site or both. Similar digests with HincII plus BglIII or SstI, BglI, or BglII alone always produced the DNA fragment expected from the map in FIG. 2, but with between two and four additional hybridizing bands (FIG. 7A and B). Multiple hybridizing bands were detected whether the HincII-HindIII or SstI probes were used in detection (FIG. 7B, lanes 2 and 5). There was no hybridization between cloned probe and bovine leukocyte DNAs (FIG. 7B, lane 4), further demonstrating the parasite origin of the cloned sequence.

Thus, the cloned DNA faithfully represents an *Anaplasma marginale* genomic sequence. However, additional partially homologous copies of the clones 3.9-kb BglII fragment are also present in the genome.

The data presented describe the expression of an *Anaplasma marginale* protein of approximately 105,000 molecular weight in recombinant *E. coli*. The antisera prepared in rabbits against immunoaffinity-isolated, nonrecombinant Am105 recognize recombinant Am105 and vice versa, showing shared epitopes. Also, antisera against recombinant Am105 react with *Anaplasma marginale* in immunofluorescence and agglutinate purified initial bodies, demonstrating the presence of recombinant Am105 epitopes on the parasites themselves. Recombinant Am105 is structurally and antigenically homologous to Am105L; no evidence was obtained for homology to Am105U.

Nonrecombinant Am105, containing both Am105L and Am105U, confers protection on cattle against challenge with *Anaplasma marginale* (17). It is not known whether Am105L or Am105U, used separated as an immunogen, would confer protection. Am105L and Am105U are both accessible on viable initial bodies to surface radiolabeling, one important criterion for an immunoprotective protein (1). Am105U may be more likely to induce protection because this polypeptide contains the epitope recognized by neutralizing monoclonal antibody 22B$_1$ (FIG. 5). However, other neutralization-sensitive epitopes may also be present in Am105L. The epitope recognized in Am105U by antibody 22B$_1$ is conserved in eight geographically distinct isolates (17), an important practical concern for potential immunization. Rabbit anti-recombinant-Am105 sera also reacted with all isolates tested in immunofluorescence, but variation in surface-exposed epitopes might not be revealed by such polyvalent sera. Examination of the *Anaplasma marginale* genome by Southern blotting suggests the presence of a family of Am105L genes and the possibility of antigen variation.

A single Am105L gene copy was detected in recombinant libraries by expression screening. Other copies of the gene may not be complete and functional, similar to pilin genes of Neisseria gonorrhoeae (15, 16, 22). Alternatively, other Am105L genes may (i) contain promoter sequences that do not function in *E. coli* or *Anaplasma marginale* or (ii) code for antigenically variant forms of the protein not detected in the expression assay. An Am105L-related gene could code for Am105U, as peptide maps do not exclude the possibility of limited homology between Am105L and Am105U. However, later testing has indicated that the proteins Am105L and Am105U are the products of separate *Anaplasma marginale* genes as explained more fully below.

Experiments in progress examine whether recombinant Am105 will induce protection in cattle against disease and whether Am105U may be expressed in *E. coli* so that both components of the Am105 complex may be tested for protection. Immunoblot experiments and that shown in FIG. 5 demonstrate that the epitope on Am105U recognized by neutralizing monoclonal antibody 22B$_1$ is not denatured by solvents such as 2% SDS, 2.5% mercaptoethanol, 10% acetic acid, and 25% isopropanol. Hence, this epitope is relatively resistant to conformational changes compared with, for example, surface-exposed epitopes of Trypanosoma brucei (4a). Other data suggest that immunoaffinity-isolated Am105 is not glycosylated and show that the epitope recognized by antibody 22B$_1$ is protease sensitive (G. H. Palmer, S. D Waghela, W. C. Davis, A. F. Barbet, and T. C. McGuire, Int. J. Parasitol., in press). Expression of the Am105U neutralization-sensitive epitope should, therefore, be readily obtained by direct monoclonal antibody screening of a fusion protein expression library, e.g., in bacteriophage lambda-gt11 (26). In those libraries, expression of Am105U epitopes would not depend on recognition of rickettsial regulatory DNA sequences by *E. coli* (21).

The most effective vaccine against *Anaplasma marginale* may be a combination of surface proteins. These include Am86, Am61, Am36, and Am31 as well as Am105, Am105L or Am105U. We described here the cloning and expression of an *Anaplasma marginale* gene in structural and antigenic homology between the cloned and native surface proteins. Since cattle are protected against *Anaplasma marginale* by immunization with Am105 purified from infected erythrocytes (19), these results suggest that a recombinant vaccine is feasible and provide a rational basis for its development.

PART IV—CLONING OF MSP-1 GENES FOR DIFFERENT

GEOGRAPHICAL ISOLATES, DNA AND AMINO ACID

SEQUENCES THEREFOR

To characterize the MSP-1a gene associated with the expression of Am105U from widely different isolates we chose the approaches and procedures for cloning and sequence analysis which are described below. Such procedures should also be interpreted in light of other procedures referenced or described herein. For analysis and sequencing the following geographical isolates of *Anaplasma marginale* were selected: Florida (FL) and Virginia (VA) isolates because they express the largest and the smallest polypeptide of the available isolates, respectively, and because our prior immunologic and molecular data on MSP-1 were obtained with FL as generally described hereinabove. Idaho (ID) isolate was chosen because it appeared the most variable by restriction analysis. Washington (WA) isolate because it was used in successful cross-challenge experiments of animals immunized with FL MSP-1 complexes.

For sake of convenience in discriminating the particular geographical isolates being referred to, the antigens may hereinafter be referred to by the "Am" designation as used above, with an additional abbreviation such as "F" for Florida, to designate the geographical isolate. For example, the Am105 generally referred to above in this application is also referred to as AmF105 to indicate the association with the Florida isolate.

To begin analysis we first created a pseudo-random genomic library from *Anaplasma marginale* Florida isolate DNA by partial digestion with the restriction enzyme Sau3A. The resulting genomic DNA fragments were modified by adding additional C-tails thereto. The resulting modified DNA fragments were inserted into plasmids pUC9 which had been previously cleaved using the restriction enzyme PstI and G-tailed. The resulting recombinant plasmids which were then used to transform *E. coli* (strain TB1). The resulting transformant bacteria were screened with $^{125}$I protein A, and monoclonal antibody 22B1 for expression of AmF105 epitopes. A portion of the MSP-1a gene for the Florida isolate which codes for a subunit of AmF105U was obtained in a 2.7 kilobase pair (kbp) insert cloned into the plasmid pUC9 to produce a plasmid herein termed pAMT1. When plasmid pAMT1 was inserted into *E. coli* it caused the synthesis of an antigen containing a subunit of AmF105U having an approximately 56,000 dalton molecular weight. The portion of the AmF105U antigen expressed by this recombinant bacterial cell is indicated in the amino acid sequence information given in FIG. 12 for the Florida isolate starting with amino acid 1 through approximately 220–230 in repeat 8.

To determine the number of MSP-1a gene copies in the chromosome of the Florida isolate of *Anaplasma marginale*, Southern blot analyses of restriction endonuclease-digested *Anaplasma marginale* genomic DNAs were performed using the 2.7 kbp insert of pAMT1 as a DNA hybridization probe. In most instances, only a single band hybridized with the probe, suggesting a single gene copy. Thus, the size polymorphisms which exist between the different *Anaplasma marginale* geographical isolates with respect to the corresponding MSP-1 protein complexes produced by each are probably due to allelic variations at one locus of the chromosome rather than, for example, by expression of different gene copies.

Figure 8:
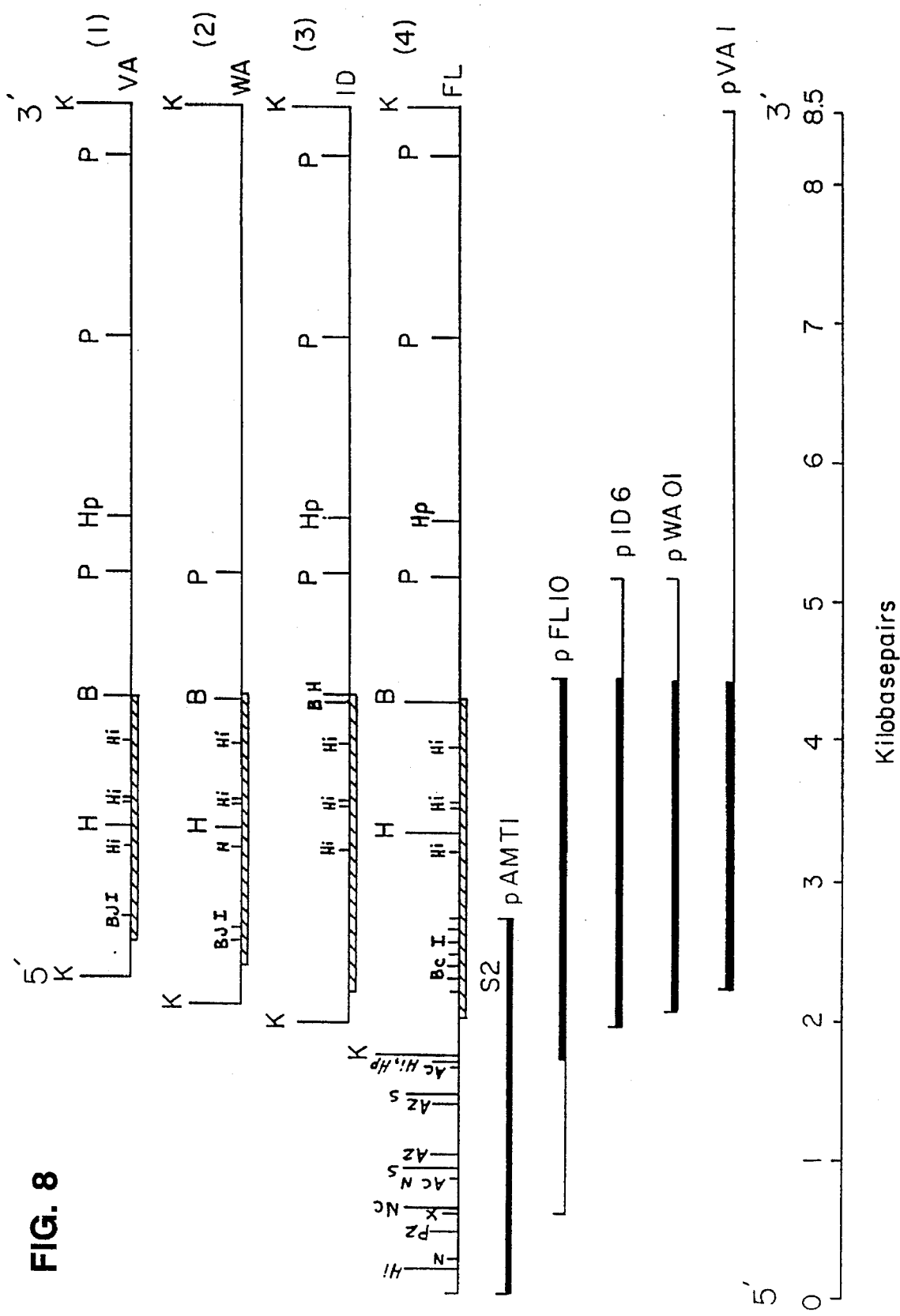
FIG. 8 shows four restriction enzyme maps (1)–(4) for four different geographical isolates of *Anaplasma marginale* indicating relevant portions of the genome containing the gene which codes for the expression of the proteins corresponding to Am105U in the Florida isolate. The identified gene areas in each map are indicated with the cross-hatched bars. Below the restriction maps are five plasmid diagrams indicating in heavy line the portion of the plasmids which incorporated part or all of the indicated genes. The portion of the plasmid not incorporating the recombinant gene DNA is shown in a light line.

Three other isolates of *Anaplasma marginale* were compared with FL by Southern blot restriction mapping, using the same probe. The restriction maps of all four isolates were virtually identical as shown in FIG. 8, with the exception of a variable length region between the internal KpnI and HindIII restriction enzyme cutting sites. This similarity in the restriction enzyme maps, as most easily seen with respect to the 3' regions relative to the hatched regions indicating the gene, which confirms the position of each MSP-1a allele at the same chromosome locus in each isolate.

The region of the plasmid pAMT1 insert containing the partial MSP-1a gene was analyzed to determine its location which was found to be in the region "right" of the KpnI site (as seen in FIG. 8). This analysis was performed by making progressive deletions in the "left" half of the DNA insert of plasmid pAMT1 using restriction enzymes and monitoring the effects of those deletions on the in vitro synthesis and size of the 56 kDa product encoded by pAMT1.

To isolate the intact MSP-1a gene from the FL isolate, we created a random-sheared genomic library of *Anaplasma marginale* DNA using sonication of the isolated DNA. The sonicated DNA fragments were blunt-ended using Klenow fragment of DNA polymerase I. NcoI linkers were thereafter added to the modified DNA fragments. The resulting DNA fragments were ligated into the expression vector plasmid pKK233-2. The resulting recombinant plasmids were implanted into *E. coli* and the resulting bacterial cultures screened with monoclonal antibody 22B1 for expression of the antigen AmF105 or antigens bearing immunologically similar epitopes. The plasmid pKAna420 was identified in the screening and further analysis of the expressed product by electrophoresis and immunoprecipitation indicated that a fully-sized immunoreactive product was being expressed.

For performing the DNA sequencing, we subcloned the *Anaplasma marginale* DNA insert contained in pKAna420 into the SmaI site of plasmid pGEM4 to create plasmid pFL10 and transformed the *E. coli* strain DH5a using pFL10. Size-selected genomic libraries were then constructed from the DNA of the Virginia, Washington and Idaho *Anaplasma marginale* isolates by ligation of DNA fragments cut by the restriction enzyme KpnI (for the VA isolate) or restriction enzymes KpnI and PstI (for the WA and ID isolates). The DNA fragment were then cloned into plasmid pGEM4 which had been linearized using enzymes KpnI or KpnI and PstI, and used to transform *E. coli* strain DH5a. The bacterial transformants were screened by colony hybridization according to the procedures of Grunstein and Hodgess, *Proceedings of National Academy of Sciences*, (U.S.A.) 72, 3961 (1975). The procedure was accomplished using a 1 Kbp DNA fragment of plasmid pAMT1 radiolabeled with 32P as a hybridization probe, which was extracted from the KpnI site (see corresponding point on Florida isolate restriction map) to the right end of plasmid pAMT1 as shown in FIG. 8. The blocked-in or bolded linear regions of the plasmid diagrams shown in FIG. 8 correspond to the regions of the four geographical isolates of *Anaplasma marginale* which were DNA sequenced (see FIG. 10 for DNA sequences). The abbreviations used in FIG. 8 are as follows: Ac=AccI; A2=AvaII; B=BamHI; BclI=BclI (multiple restriction sites are shown for this enzyme for WA and FL isolates); H=HindIII; Hi=HincII; Hp=HpaI; K=KpnI; N=NsiI; Nc=NcoI; P=PstI; Sm=SmaI; Ss=SstI; and X=XmaIII.

Figure 9:
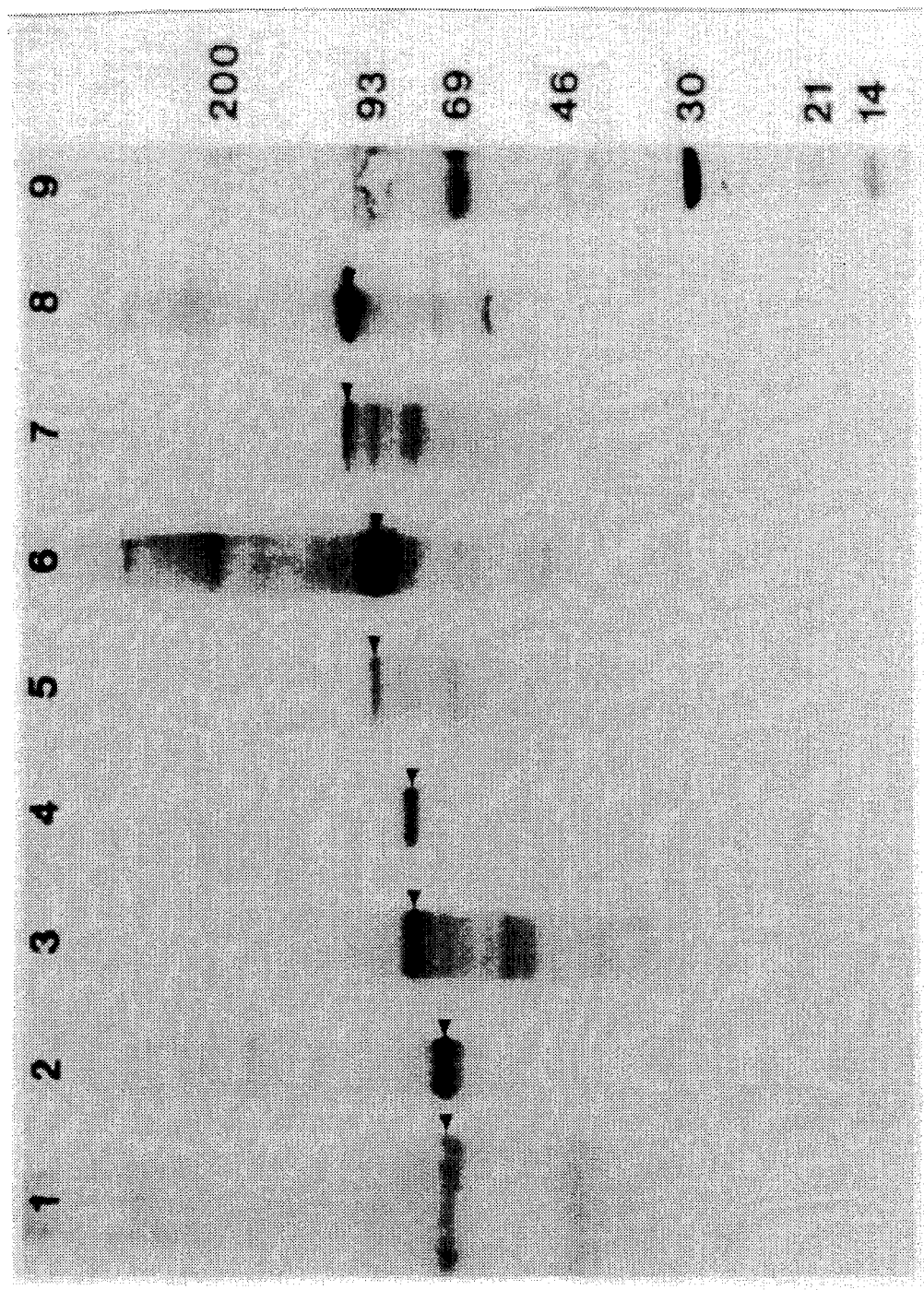
FIG. 9 is a reproduction of a radiograph showing electrophoretically separated proteins expressed by the recombinant E. coli cell lines which incorporated the recombinant plasmids pVA1, pWAO1, pID6, and pFL10. Also shown are native proteins from the corresponding *Anaplasma marginale* isolates.

The fidelity of all four cloned fragments with the associated isolate *Anaplasma marginale* chromosome was confirmed by Southern blot comparisons of restriction fragments with genomic DNA (not shown) and by the expression of full-sized immunoreactive products by each transformant as shown by the Western blots of FIG. 9. The electrophoretic mobility tests indicated by FIG. 9 were produced from the recombinant *E. coli* which were grown to an Asso of 0.5–0.6 in L-broth containing 50 micrograms/milliliter ampicillin. They were collected by centrifugation and disrupted by boiling for 3 minutes in SDS-PAGE sample buffer, such as described by Laemmli, *Nature* (London), 227, 680 (1970). The polypeptides were fractionated on 7.5–17.5% gradient polyacrylamide gels, and transferred electrophoretically to nitrocellulose, and probed with monoclonal antibody 22B1 and $^{125}$I-protein A. The bands containing the products of the MSP-1a gene recognized by monoclonal antibody 22B1 are indicated by arrowheads. Molecular weight standards shown at the right of that Fig. are given in kilodaltons. Lanes 1,3,5, and 7 are recombinants pVA1, pWAO1, pID6 and pFL10, respectively. Lanes 2, 4, 6, and 8 are polypeptides produced by VA, WA, ID and FL *Anaplasma marginale* initial bodies.

DNA sequences for the four different geographical isolates of *Anaplasma marginale* were obtained as shown in FIG. 10. The DNA inserts in the recombinant plasmids pGEM4 were sequenced using the dideoxynucleotide method of Sanger et al., *Proceedings of National Academy of Sciences* (U.S.A.) 82, 648 (1985). The SP6 and t7 promoter primers of pGEM4 were used to prime the initial sequencing reactions. Once into each insert, new primers were synthesized based on the sequences just obtained and used to extend the region sequenced. The sequences are given from the 5' KpnI site of each to clone to the same point representing the 3' end of the Florida isolate it cloned insert. Annotations above the sequences indicate the KpnI site, features of the promoter region, the start of transcription, the start and stop codons of the coding sequence, and the repeat units. Variant bases are indicated by asterisks beneath the sequence, whereas insertion or deletions are indicated by dashes. A region of homology near the 3' end which is contained in repeat regions is double underlined there and in the repeat regions. Further discussion of notable points about the DNA sequences will be given below.

The above descriptions of suitable methods for gene identification, isolation, cloning and expression are also applicable to remaining antigens according to this invention. More specifically, these techniques, with suitable modification for the particular antigen being sought, may also be used to create recombinant plasmids or other recombinant vectors containing recombinant nucleic acids, DNA or RNA, coding for the expression of purified antigenic proteins similar to or the same as the native antigens indicated above for *Anaplasma marginale*. More particularly, indicated antigens, such as Am220, Am105 (complex), Am105U, Am105L, Am86, Am61, Am56, Am42, Am36, Am31 and Am25; even more preferably Am105 (complex), Am105U, Am105L, Am86, Am61, Am36, Am31, and Am15; from the Florida isolate as used in the research indicated above, or the antigenically similar proteins and polypeptides from other isolates of *Anaplasma marginale* might be produced by such recombinant techniques. Similarly, such recombinant techniques may be applied to determine the DNA and/or polypeptide sequences of the desired antigenic, and in applicable uses immunogenic, proteins or polypeptides. The amino acid sequence information can then be used to produce the antigenic polypeptides according to well-known polypeptide synthesis techniques which are commercially available given knowledge of the desired polypeptide sequence to be constructed. tI should also be appreciated that the antigens, vaccines, recombinant vectors and recombinant cells, methods and other aspects of this invention are in there broader concepts applicable to the broader classes of Rickettsiae since at least one member thereof is immunologically treatable and detectible using the antigens and vaccines of this invention. This in particular applies to the more specific nucleic acid and amino acid sequences, described above and in more detail below, which are known effective for inducing an immune response against such parasitic organisms.

Description of the MSP-1a Gene Structure

Portions of each of the four DNA inserts of the recombinant plasmids pFL10, pID6, pWAO1, pVA1, and plasmid pAMT1 were sequenced with the sequenced portions of the four isolate derived plasmids indicated by the bold lining in FIG. 8 and by the DNA sequences shown in FIG. 10, except pAMT1 which is not shown in FIG. 10 because it is redundant with portions shown for pFL10.

To define the gene we first located the transcription start site. To do this, total cellular RNA from the Florida isolate *Anaplasma marginale* initial bodies was sequenced using a primer specific to a region near the 5' end of the only significant open reading frame (ORF), according to a procedure indicated by Vander Ploeg et al., *Nucleic Acids Research* 10, 3591 (1982). The RNA was sequenced directly with Avian Myeloblastosis Virus reverse transcriptase by a modification explained in Hollingshead et al, *Molecular Cell*

Figure 11A:
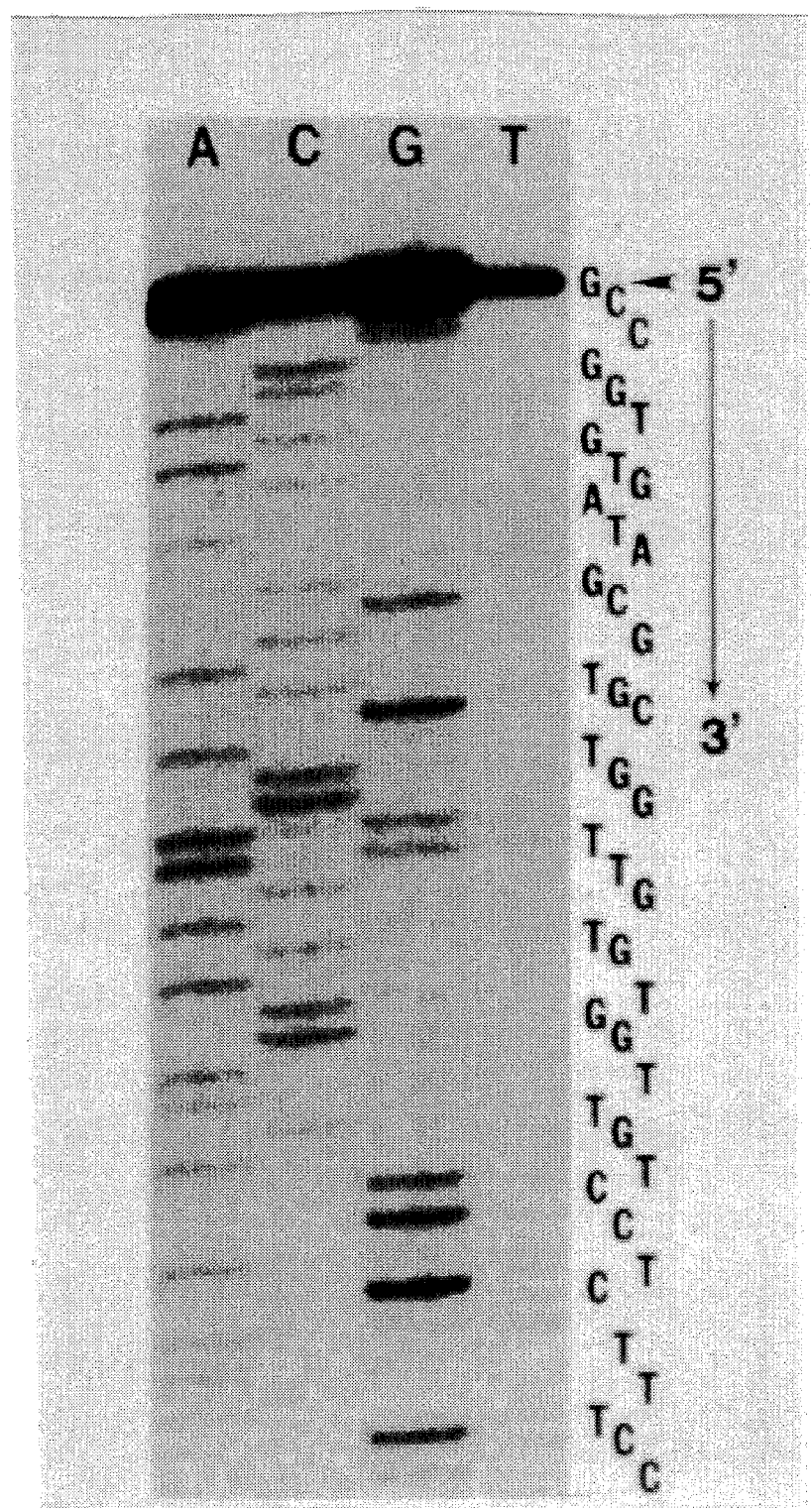
FIG. 11A is a reproduction of a radiograph showing DNA fragment electrophoretic separations indicating the start of transcription in the Florida isolate MSP-1a gene.

Genetiics 207, 196 (1987), of the method of Inoue and Cech, National Academy of Sciences (U.S.A.) 82, 648 (1985). Synthesis of a runoff transcript ending at base 1FL (for base number 1 of the FL isolate sequence) identified this as the start of transcription (see FIG. 11A). The primer was the reverse complement of bases 147FL to 166FL (see FIG. 10).

The presumptive promoter for the MSP-1a gene was identified by its location relative to the transcription start site and by its striking homology with *E. coli* promoter consensus sequences. The promoter region structures of the different geographical isolate alleles and *E. coli* vary slightly as shown in FIG. 11B. The −35 and −10 region, and the start of transcription are indicated by a double underline in that Fig. Homologous bases between the *E. coli* consensus promoter and the *Anaplasma marginale* promoter sequences are indicated by bolding. Lower case letters indicate bases not shared between the two organisms. The two bases different between ID and the other three MSP-1a alleles are indicated by a single underline. In FIG. 11B "n" represents any deoxynucleotide.

The FL, VA and WA alleles are identical from the transcription start site to the 5' end of the −35 region. The ID allele has a 1 base deletion within the −35 region, at position −30FL. The spacing between the −35 and −10 regions is maintained, however, by insertion of a T at position −22FL (see FIGS. 10 and 11B) and all four alleles match that of the *E. coli* consensus sequence. Immediately 5' to the −35 region is an extremely A+T-rich stretch in which A or T occupy 23 of the 25 bases in that sequence.

In the four alleles there is an apparently untranslated leader of 127 nucleotides for the FL, WA and VA isolates, or 71 nucleotides for the ID, as defined by the start of transcription at base 1FL and the start methionine codon at bases 128FL–130FL. Relative to FL, the VA and WA alleles are identical in this region except for an A to G transition at position 10FL. The ID allele, on the other hand, has a T to G transversion at position 8FL and deletions of 1, 51 and 4 bases in this region. Despite these differences in the 5' untranslated region the FL, WA and ID alleles are expressed at comparable levels in *E. coli* (DH5a). Although VA is not comparably expressed, this may be because of differences in plasmid copy number or products encoded by sequences 3' to the end of the MSP-1a gene which are absent from the other recombinants. We have not pursued this question.

We think that translation begins at the methionine codon of bases 128FL–130FL, for the following reasons: 1) The only long open reading frame in this gene begins just 5' to this codon coding; 2) although there is another methionine codon coding sequence upstream at bases 45FL–47FL, it is not in the same open reading frame as the long open reading frame and is absent altogether in the ID isolate; 3) monoclonal antibody 22B1 binds to a synthetic oligopeptide encoded by this reading frame (see FIG. 14); and 4) there are no other methionine codons in the open reading frame until a point beyond that contained in plasmid pAMT1, which expresses a fragment of the polypeptide. In each of the alleles one long open reading frame is present which extends to the same apparent stop codon sequence at bases 2429FL–2431FL (see FIG. 10).

Between alleles there is an extremely high degree of overall homology throughout the coding region, including a 639 bp region from bases 1686FL–2324FL that is completely conserved. However, there are three regions in the coding sequence with a high degree of variability. The first 30 bases of the DNA coding sequence comprises a hypervariable region wherein FL, VA and WA each have 4 substitutions, whereas ID has only 27 bases in the same region, of which 7 vary from the other isolates. The result is an associated N-terminal amino acid region shortened from 10 to 9 amino acids, with 4 substitutions between isolates, three of which are non-conservative. A similar clustering of substitutions at the 3' end results in 5 amino acid differences in the final 35 residues. Finally, the 120 bp stretch from bases 1184FL to 1202FL is a highly variable region, with 11 base substitutions resulting in the substitution of 11 out of 40 amino acids (see FIGS. 10 and 12). Eight of these substitutions are non-conservative, and 7 of the 11 are in regions predicted to be short coil-turn structures. This may be important to host responses to this antigen.

A notable feature of the MSP-1a gene for all four isolates is the presence of a DNA tandem repeat region containing a series of similar tandemly repeated DNA sequences which each contain 84 or 87 bp. These DNA tandem repeat sequences code for the expression of polypeptide sequences having 28 or 29 amino acids, respectively. The tandemly repeated sequences are repeated two times in the VA isolate, four times in the WA isolate, six times in the ID isolate, and eight times in the FL isolate. It is interesting that each of the alleles varies by a multiplicative factor of two in the number of repeats but we cannot at this time ascribe any particular significance to this observation. The tandem repeats of 28 or 29 amino acid units immediately follow the N-terminal 10 (or 9) amino acids.

FIG. 13 shows that the repeated amino acid sequences are present in only five forms, herein termed repeat forms A–E, for all repeat sequences contained in the tandem repeat regions of the four *Anaplasma marginale* isolates. Each geographical isolate allele contains two repeat forms. The primary structures of the various repeat forms are highly conserved with 25 amino acids of the 28 or 29 mer sequences being completely conserved in all five repeat forms defining all tandemly repeated sequences of these isolates. In each allele, the tandem repeat domain begins or ends with a single copy of one repeat form whereas the second repeat form is present in one to seven copies. Variations in the number of tandem repeats present in each allele can completely explain the size polymorphisms of the Am105U protein for these four geographical isolates of *Anaplasma marginale* without any need to invoke other mechanisms to explain the differences.

The 28 and 29 mer amino acid sequences shown in FIG. 13 include conserved amino acid sequences DSSSA, GQQQESSVSSQS, EASTSS or QASTSS, and QLG. One or more of these sequences or their subunits can be significant in defining antigens in accordance with this invention. Antibody 22B1 selectively binds to sequences EASTSS and QASTSS as explained more fully below. Antibody titers have been developed in cattle against the Florida isolate 29 mer polypeptide shown in FIG. 13 as repeat form B. Coupling of one or more of these repeat sequences to additional polypeptide sequences may also be significant in stimulating an immune response which is characterized by the 28 or 29 mer amino acids sequences, or subunits thereof, such as the conserved subunits indicated in this document. These highly conserved tandem repeat units or homologous regions may also be conserved in other rickettsial organisms, thereby allowing additional rickettsial infections to be detected, treated or vaccinated against using the antigens and immunogens including these amino acid sequences, there subunits or combinations thereof.

Analysis of the amino acid sequence information clearly indicates that the actual molecular weights of all antigenic proteins coded by the MSP-1a genes of the different isolates is anomalous to the molecular weights predicted by sodium dodecylsulfate-polyacrylamide gel electrophoretic mobility comparisons with standards used in the testing. Each of the antigens migrates in electrophoresis in a manner appearing significantly larger than the encoded size. This variance between electrophoretic mobility and actual molecular weight is a recognized property of proteins containing domains of tandemly repeated amino acids.

In addition to the various tandem repeat units, there are five other known sequence regions in the FL allele sharing significant homology with the tandem repeats. Four of these homologous regions form a series overlapping the same region within the repeat structure (exemplified by bases 236FL to 277FL). The first homologous region, bases 2240FL–2254FL, contains the DNA sequence GGTGGc-CAGCAGCAg-(mismatches are in lower case, see FIG. 10). This sequence shares 13 of 15 bases with the homologous region of the tandem repeats. This region is within the long open reading frame, is in frame synchronization, and the base differences are silent (coding for the same amino acid), thus encoding the amino acid sequence GGQQQ in each region. The second homologous region (not shown in FIG. 10) is coded by bases −1188FL to −1208FL which include the DNA sequence TTAtGcGCaGATgcCaCcTCA. This region shares 14 of 21 bases. The third homologous region, bases −1292FL to −1308FL (also not shown) (TCA-GOGGGTcGTCAGCA), shares 16 of 17. The fourth homologous region, bases −1450FL to −1461FL (CgGCAG-gAAGcG), shares 9 of 12 bases. The four homologous regions overlap an area of the repeat sequence exemplified by bases 260FL–274FL, 236FL–256FL, 254–270FL and 266FL–277FL, respectively. The fifth homologous region, bases −496FL to −516FL (CAGGaCcGcAaATGgGcCT-CAA), shares 15 of 21 bases with a stretch exemplified by bases 302FL to 322FL. These homologous regions may reflect the origin of the repeats as discussed below.

Mapping the Neutralization-Sensitive Epitope

In particular we wished to map the epitope recognized by monoclonal 22B1 because of the demonstrated neutralization ability in vitro and effectiveness of the antigen Am105 (complex) and the binding of monoclonal antibody 22B1 to this immunogen, thus indicating the potential importance of this epitope in immune recognition. Plasmid pAMT1 encodes a subunit polypeptide of AmF105U which is recognized by monoclonal antibody 22B1 yet contains only the N-terminal 10 amino acid stretch and seven complete and one partial repeats. Because of this we targeted our search to the repeat structure. Our approach was to assay the binding ability of monoclonal 22B1 to various synthetic oligopeptides containing overlapping stretches of the B repeat. The minimum structure necessary to bind this antibody was found to be the six amino acid sequence QASTSS. This sequence is present in one of two isoforms in each of the repeats, the alternative sequence being EASTSS. Both synthetic peptides bound equivalents amounts to monoclonal 22B1, whereas the 5 mer polypeptide. ASTSS and QASTS, did not bind antibody. The results of these experiments are summarized in FIG. 14.

Oligopeptides of varying lengths and containing different regions of the A and B repeats of the antigen AmF105U polypeptide were assayed for monoclonal antibody 22B1 binding affinity. A (+) reaction indicates monoclonal 22B1 binding in these assays. An (−) reaction indicates no detectable monoclonal 22B1 binding. Results were obtained by solution-phase phase inhibition radioimmunoassay using $^{125}$I-labeled AmF105, which were confirmed by an enzyme-linked immunosorbent assay and by immunoblot assays. The enzyme-linked assay was performed as described previously by Palmer et al., International Journal for Parasitology, 17, 1279 (1987), with the following modifications. The microtiter plates were first coated with bovine serum albumin to which was added the oligopeptides in 0.25% (w/v) glutaraldehyde, 10 mM sodium phosphate, 94 mM ethylenediamine tetraacetic acid, pH 6.8. Blocking and washing steps were done using a veronal buffer of the following composition: 145 mM sodium chloride, 1.8 mM sodium 5,5'-diethylbarbiturate, 4.5 mM barbituric acid, 0.5 mM $MgCl_2$. The visualizing system was horseradish peroxidase coupled to recombinant Protein G. For the immunoblot assays, serial dilutions of the oligopeptides were spotted onto nitrocellulose previously coated with bovine serum albumin in water. The blots were fixed in 2.5% (v/v) glutaraldehyde. After extensive washings with tris-buffered saline, the blots were incubated with monoclonal 22B1, then with rabbit anti-mouse IgG, and finally with $^{125}$I-protein A, as described in Palmer it al., Science 231, 1299 (1986).

Synthetic 29 mer oligopeptides containing the sequence shown in FIG. 13 as Form B were tested in calves to determine the antigenic capability of this sequence. Two calves were given 400 microgram doses at four times. The first injection was given in approximately 1–2 milliliters of Freund's complete adjuvant. Three boosters containing similar amounts of the antigenic oligopeptide were given thereafter at approximately 2 week intervals. Three additional calves were similarly inoculated with another vaccine incorporating similar amounts of an antigen containing the synthetic 29 mer oligopeptides which had been polymerized with the cross-linking agent carbodiimide to produce antigens having approximate electrophoretic mobilities corresponding to molecular weights of 20,000 to 200,000 daltons, Science 144, 1344 (1964). All five of the calves were checked for serum antibody titers approximately months after the initial inoculation and shortly after the last booster injection. Titers were analyzed against both immunoaffinity purified AmF105 and the 29 mer synthetic oligopeptide which were coated in the wells of the titer plates. The results of these test are shown below in Table 6. All calves were tested for titers prior to inoculation and found to have negligible reaction.

TABLE 6

| | Titers AmF105 | Titers 29 mer Oligo. |
|---|---|---|
| 29 mer Oligopeptide Vaccine | | |
| Calves 1 and 2 | 1:100 | 1:1000 |
| 29 mer Oligo. and Polymerized Carboiimide Vaccine | | |
| Calf 3 | 1:10,000 | 1:10,000 |
| Calves 4 and 5 | 1:1,000 | 1:10,000 |
| Immunoaffinity Purified AmF105 Vaccine | | |
| Calf 6 | 1:10,000 | 1:1,000 |

The entire repeat domain is predicted by structural algorithms to be comprised of coil/turn segments, consistent with a short, linear epitope. However, the binding affinity of monoclonal 22B1 for the entire 29 mer repeat B was approximately two orders of magnitude greater than for either minimal epitope, suggesting some structural influence.

Our results have revealed several interesting features of the MSP-1a gene and its encoded polypeptide products including recombinant Am105U, for the various isolates, and subunit antigens derivable therefrom. The presence of a tandem-repeat domain has not been reported before in a rickettsial surface protein, although they are found in the taxonomically distant streptococcal M proteins and in several eukaryotic parasite surface antigens. The variable numbers of repeats in this domain explains the extreme size polymorphisms of this polypeptide. The epitope bound by monoclonal antibody 22B1 was strictly conserved in each repeat of each isolate, even though it can function in neutralization of parasite infectivity.

In addition to the variable numbers of repeats there are three highly variable regions in the polypeptide, including the N-terminal end. The gene uses promoter structures and spacings very similar to the *E. coli* promoter consensus sequences. Despite the similarities between the MSP-1a promoter and *E. coli* promoter consensus sequences, one significant difference emerged: No obvious ribosome binding site was detected in the untranslated leader region, even though this gene is expressed in *E. coli* in appreciable amounts. The sequence GTGTGTG, found in the −11 to −5 (relative to the ATG codon) position may still base pair with the ribosomal RNA but with a lowered affinity.

An unusual structural feature of the AmF105 polypeptide is that although it is a surface protein and accessible to antibody, no obvious signal sequence to promote its translocation to the outer membrane bilayer was detected. A hydropathy plot of the predicted polypeptide reveals five major hydrophobic stretches from amino acids 255FL–270FL, 541FL–557FL, 567FL–585FL, 631FL–650FL, and 662FL–678FL, the last four of which are sufficient in length and hydrophobicity to serve as transmembrane domains. One of these hydrophobic domains may serve as an uncleaved, internal signal sequence.

The hypervariable nature of the N-terminal end of AmF105 suggests that this domain may not serve a structural or targeting function. On the other hand, this sequence and that of the highly variable region of amino acids 353FL to 392FL could serve immunologic functions, providing epitope(s) necessary for T-cell recognition. If so, T-cell and host subpopulations capable of responding to AmF105 could be modulated by these regions. Mutations in these regions therefore may provide a level of antigen variation enabling survival of the parasite in host populations immune to heterologous isolates.

The tandem repeat structures have been hypothesized to develop by multiple events of unequal homologous recombination and/or slipped-strand mispairing. The origin of the tandem repeats in AmF105 is unknown. Sequences sharing significant homology with the repeats are also seen at other sites within and outside the MSP-1a gene coding sequence. Given the lengths of the tandem repeats (84 or 87 bp), unequal homologous recombination is the more likely mechanism as longer sequences reduce the probability of slipped-strand mispairing.

Our characterization of multiple MSP-1a gene alleles has clarified one molecular basis for rickettsial surface antigen size polymorphisms. Having defined several features of the MSP-1a gene will enable us to map T-cell epitopes of AmF105 and to assess the potential for T-cell epitope-based antigen variation in *Anaplasma marginale*. The applicability to other rickettsial organisms can also be further investigated. Definition of a conserved neutralization-sensitive epitope allows us to further assess the immunoprotective of synthetic, including recombinantly produced, peptide-based vaccines.

In addition to the four alleles of the MSP-1a gene, we have cloned the Florida isolate MSP-1b gene using procedures the same as or very similar to those described herein. The MSP-1b gene for the Florida isolate codes for the production of recombinant AmF105L, the second surface protein subunit of the MSP-1 complex in the Florida isolate of *Anaplasma marginale*. FIG. 15 is a restriction enzyme map for the MSP-1b Florida gene showing the cutting sites for a variety of enzymes. FIG. 16 shows the DNA and associated amino acid sequences coded for by the AmF105L gene. The last part of FIG. 16 also shows the amino acid composition of the expressed recombinant antigen and the calculated molecular weight of 80,359.85 daltons which compares to the electrophoretic mobility measurements of approximately 100–105 kilodaltons. Thus the production of recombinant MSP-1 complexes can be developed by co-expression of the MSP-1a and MSP-1b genes in a heterologous system.

The amino acid sequence abbreviations used in this document are shown in the Appendix A filed herewith.

FIG. 1. Detection of *A. marginale* proteins on nitrocellulose with antibody and $^{125}$I-labeled protein A. (A) Known positive and negative control antigens were applied to all filters in sequential 10-fold dilutions and in duplicate: *A. marginale*-infected erythrocytes ($2\times10^5$ to $2\times10^3$ total cells at 60% parasitemia) and noninfected erythrocytes (same concentration. Am105 protein (10 to 0.1 ng). Am36 protein (10 to 0.1 ng), and ovalbumin (10 to 0.1 ng). A different antibody was tested on each filter: R873 (1:4,000 dilution), R781 (1:400 dilution), $F34C_1$ (2 μg/ml), and $F19E_1$ (2 μg/ml). (B) Recombinant *E. coli*, selected as potentially positive colonies in a previous screen, were rescreened on duplicate filters for reaction with R873. The two spots at the top right of each filter are duplicate signals from a positive control antigen: 1 μl containing $2\times10^4$ total erythrocytes at 60% parasitemia. Uninfected erythrocytes (1 μl) were also applied in duplicate to each filter and gave no signal.

FIG. 2. Restriction enzyme maps of plasmid insert DNA from *E. coli* colonies expressing Am105 determinants. L (left) and R (right) refer to the orientation of insert DNA with respect to pBR322 sequences. L is proximal to the pBR322 EcoRV site, and R is proximal to the SphI site. A, AvaI; Ap, ApaI; Ban, BanII; Bg, BglI; B1, BglII; Ec, EcoRV; H, HpaI; Hc, HincII; Hd, HindIII; M1, MluI; Nd, NdeI; Pu, PvuII; Sm, SmaI; Sp, SphI; Ss, SstI; Tt, Tth111I; Xa, SmaIII; Xb, XbaI; Xh, XhoI.

FIG. 3. *A. marginale* proteins synthesized by recombinant *E. coli*. *E. coli* organisms containing pBR322 or pAM25 plasmid DNA were radiolabeled with [$^{35}$S]-methionine during in vitro culture, and a detergent extract was immunoprecipitated with different antisera. Immunoprecipitates were analyzed by 7.5 to 17.5% polyacrylamide-SDS gel electrophoresis and fluorography. Lanes: 1, $^{14}$C-labeled molecular weight standard proteins; 2 to 7, *E. coli* plus pAM25; 8 to 13, *E. coli* plus pBR322; 7 and 8, total $^{35}$S-protein profiles. Immunoprecipitating antibodies were normal rabbit serum (lanes 6 and 9), R873 (lanes 5 and 10), R612 (lanes 4 and 11), R874 (lanes 3 and 12), and R781 (lanes 2 and 13).

FIG. 4. Comparison of recombinant Am105 (rAm105) with Am105L and Am105U. *E. coli* cells containing pAM25 (lane 1) or pBR322 (lane 2) were radiolabeled with [$^{35}$S]-methionine during in vitro culture, and a detergent extract was immunoprecipitated with R873. *A. marginale* was also labeled with [$^{35}$S]-methionine and immunoprecipitated with neutralizing monoclonal antibody 22B$_1$ (lane 3) or with control monoclonal antibody 24A$_1$ (lane 4). Immunoprecipitates were analyzed on a 7.5% polyacrylamide-SDS gel containing 3M urea; lane 5, $^{14}$C-labeled molecular weight standard proteins. (B) Partial proteolysis products of recombinant Am105, Am105L, and Am105U, produced by digestion in the stacking gel with 0.025 μg of S. aureus V8 protease, were compared on a 15% polyacrylamide-SDS gel.

FIG. 5. Antigenic comparison of recombinant Am105, Am105U, and Am105L. $^{35}$S-labeled Am105U and Am105L were immunoprecipitated, separately or together, with different antibodies as indicated. All precipitates were analyzed on 7.5% polyacrylamide-SDS gels containing 4M urea: Am105L, lanes 1, 4, 8, and 11; Am105U, lanes 2, 5, 9, and 12; and both Am105U and Am105L (22B$_1$ precipitates of $^{35}$S-labeled A. marginale), lanes 3, 6, 7, and 10.

FIG. 6. Surface radiolabeling and immunoprecipitation of A. marginale initial bodies. Initial bodies were radiolabeled with $^{125}$I, using lactoperoxidase, and a detergent extract was immunoprecipitated with R873 (lane 1), monoclonal antibody 22B$_1$ (lane 2), R911 (lane 3), monoclonal antibody 1E$_1$ (lane 4), and R907 (lane 5). Immunoprecipitates were analyzed on a 5% polyacrylamide-SDS gel containing 4M urea.

FIG. 7. Comparison of A. marginale genomic DNA with recombinant plasmid DNA by Southern blotting. (A) Either pAM14 (p) or A. marginale genomic DNA (g) was digested with restriction enzymes, subjected to electrophoresis, and probed with nick-translated 1.4-kb HincII-HindIII insert DNA from pAM14. (B) A. marginale genomic DNA (g) or bovine leukocyte DNA (wbc) was digested with restriction enzymes, subjected to electrophoresis, and probed with the 1.4-kb HincII-HindIII fragment of pAM14 (lanes 1 to 3) or 2.0-kb SstI fragment of pAM97 (lanes 4 and 5). The genomic bands corresponding to those produced from the cloned 3.9-kb BglII fragment are indicated by thin arrows on the gels.

FIG. 10. DNA sequence of the FL, VA, WA, and ID alleles of msp1a gene.

FIG. 11B. Structures of the promoter regions of the FL, VA, WA, and ID alleles of the msp1a gene.

FIG. 12. Variant AMF105 polypeptide sequences encoded by the FL, VA, WA, and ID alleles of the msp1a gene.

FIG. 13. Sequences of the repeat forms encoded by the FL, VA, WA, and ID alleles of the msp1a gene FIG. 14. Mapping of the neutralization-sensitive mAb 22B1-binding epitope.

FIG. 15. Restriction sites of AMF105L_SYN from base no. 1 to base no. 2746. All enzymes listed are commercially available. ^ appears below base just preceding restriction cut. If cut site is unknown, mark is placed in center of cite. First letter of enzyme name is below ^. Note that the cut for many enzymes with asymmetric recognition sequences will be distant from that sequence.

FIG. 16. Translated sequence of AMF105L_SYN.

APPENDIX A

THE TWENTY AMINO ACIDS

| Type of Amino Acid | 3-Letter Symbol | 1-Letter Symbol |
|---|---|---|
| Hydrophobic (Aliphatic Side Chain) | | |
| Glycine | Gly | G |
| Alanine | Ala | A |
| Valine | Val | V |
| Leucine | Leu | L |
| Isoleucine | Ile | I |
| Basic (Diamino) | | |
| Arginine | Arg | R |
| Lysine | Lys | K |
| Acidic (Dicarboxylic) | | |
| Glutamic acid | Glu | E |
| Aspartic acid | Asp | D |
| Amide-Containing | | |
| Glutamine | Gln | Q |
| Asparagine | Asn | N |
| Hydroxyl-Containing | | |
| Threonine | Thr | T |
| Serine | Ser | S |
| Sulfur-Containing | | |
| Cysteine | Cys | C |
| Methionine | Met | M |
| Aromatic | | |
| Phenylalanine | Phe | F |
| Tyrosine | Tyr | Y |
| Heterocyclic | | |
| Tryptophan | Trp | W |
| Proline | Pro | P |
| Histidine | His | H |

We claim:

1. A vaccine composition for inducing an immune response in a ruminant, said vaccine composition comprising a purified surface protein antigen of *Anaplasma marginale*, wherein said antigen has a molecular weight of approximately 105 kilodaltons, said vaccine composition further comprising a pharmaceutically acceptable carrier or diluent.

2. A method for inducing an immune response in a ruminant to provide immune protection which reduces the severity of or prevents infection by *Anaplasma marginale*, said method comprising administering to said ruminant an effective amount of a vaccine composition comprising a purified 105 kilodalton surface protein antigen of *Anaplasma marginale* capable of inducing an immune response in a ruminant, said composition further comprising a pharmaceutically acceptable carder or diluent.

* * * * *

UNITED STATES PATENT AND TRADEMARK OFFICE
CERTIFICATE OF CORRECTION

PATENT NO. : 5,549,898
DATED : August 27, 1996
INVENTOR(S) : McGuire et al.

It is certified that error appears in the above-identified patent and that said Letters Patent is hereby corrected as shown below:

Column 6: Line 41: "Budaoesr" should read --Budapest--.
Column 9: Line 54: "minutes" should read --30 minutes--.
Column 10: Line 17: "Immunol123" should read --Immunol 123:--.
Column 12: Line 35: "NAN$_3$" should read --NaN$_3$--.
Column 14: Line 41: "monocional" should read --monoclonal--; Line 54: "1331010" should read --1331010--; Lines 61&62: "(1000 is erythrocytes"should read --(1000 erythrocytes--.
Column 15: Line 1: "Ttypanosoma" should read --Trypanosoma--.
Column 16: line 59: "NAN$_3$" should read --NaN$_3$--.
Column 19: Line 63: "Clarkson" should read --Clarkston--.
Column 22: Line 6: "BglII" should read --BglII--.
Column 23: Line 4: "BglII" should read --BglII--; Line 15: "BglII" should read --BglII--; Line 18: "BglII" should read --BglII--; Line 21: "BglII" should read --BglII--.
Column 24: Line 11: "antigenie" should read --antigenic--.
Column 25: Line 16: "antigenie" should read --antigenic--; Line 11: "[$^{33}$S]" should read --[$^{35}$S]--; Line 59: "BglII" should read --BglII--.
Column 26: Line 11: "BglII" should read --BglII--; Line 12: "BgIII" should read --BglII--; Line 16: "HindIII" should read --HindIII--; Line 32: "immunofiuorescence" should read --immunofluorescence--.

UNITED STATES PATENT AND TRADEMARK OFFICE
CERTIFICATE OF CORRECTION

PATENT NO. : 5,549,898

DATED : August 27, 1996

INVENTOR(S) : McGuire et al.

It is certified that error appears in the above-identified patent and that said Letters Patent is hereby corrected as shown below:

Column 29: Line 19: "Hodgess" should read --Hogness--; Line 22: "32P" should read --$^{32}P$--; Line 44: "Asso" should read --$A_{550}$--; Line 55: "p1D6" should read --pID6--.

Column 31: Line 4: "1 of the FL" should read --$\underline{1}$ of the $\underline{FL}$--.

Column 34: Line 37: "approximately months" should read --approximately 2 months--.

Column 36: Line 49: "SrnaIII" should read --SmaIII--.

Signed and Sealed this

Twenty-fifth Day of March, 1997

*Attest:*

BRUCE LEHMAN

*Attesting Officer*     *Commissioner of Patents and Trademarks*